United States Patent
Sciascia et al.

(10) Patent No.: US 12,274,696 B2
(45) Date of Patent: Apr. 15, 2025

(54) METHODS OF ADMINISTERING NALBUPHINE

(71) Applicant: Trevi Therapeutics, Inc., New Haven, CT (US)

(72) Inventors: Thomas Sciascia, Belmont, MA (US); Shashank Rohatagi, New Haven, MA (US)

(73) Assignee: Trevi Therapeutics, Inc., New Haven, CT (US)

(*) Notice: Subject to any disclaimer, the term of this patent is extended or adjusted under 35 U.S.C. 154(b) by 0 days.

(21) Appl. No.: 17/739,848

(22) Filed: May 9, 2022

(65) Prior Publication Data

US 2022/0265640 A1    Aug. 25, 2022

Related U.S. Application Data

(63) Continuation of application No. PCT/US2021/012734, filed on Jan. 8, 2021.

(60) Provisional application No. 63/014,306, filed on Apr. 23, 2020, provisional application No. 62/959,701, filed on Jan. 10, 2020.

(51) Int. Cl.
*A61K 31/485* (2006.01)
*A61P 11/00* (2006.01)

(52) U.S. Cl.
CPC .............. *A61K 31/485* (2013.01); *A61P 11/00* (2018.01)

(58) Field of Classification Search
CPC ........ A61K 31/485; A61P 11/00; A61P 11/16; A61P 25/04
USPC ........................................................ 514/282
See application file for complete search history.

(56) References Cited

U.S. PATENT DOCUMENTS

| | | | |
|---|---|---|---|
| 4,443,442 A | 4/1984 | Skillern | |
| 4,720,384 A | 1/1988 | Di Luccio et al. | |
| 5,750,534 A | 5/1998 | Yoa-Pu et al. | |
| 5,760,023 A | 6/1998 | Farrar et al. | |
| 5,855,913 A | 1/1999 | Hanes et al. | |
| 5,874,064 A | 2/1999 | Edwards et al. | |
| 6,156,769 A | 12/2000 | Farrar et al. | |
| 6,174,891 B1 | 1/2001 | Nagase et al. | |
| 6,316,461 B1 | 11/2001 | Nagase et al. | |
| 6,451,806 B2 | 9/2002 | Farrar | |
| 6,565,885 B1 | 5/2003 | Tarara et al. | |
| 6,569,449 B1 | 5/2003 | Stinchomb et al. | |
| 6,703,398 B2 | 3/2004 | Hu et al. | |
| 6,787,149 B1 | 9/2004 | El Khoury et al. | |
| 6,946,117 B1 | 9/2005 | Schutt et al. | |
| 6,984,493 B1 | 1/2006 | Kumagai et al. | |
| 7,056,500 B2 | 6/2006 | Bentley et al. | |
| 7,563,899 B2 | 7/2009 | Boyd et al. | |
| 7,884,102 B2 | 2/2011 | Dolle et al. | |
| 8,105,590 B2 | 1/2012 | Yao et al. | |
| 8,309,596 B2 | 11/2012 | Flohr et al. | |
| 8,394,812 B2 | 3/2013 | Baichwal et al. | |
| 8,476,318 B2 | 7/2013 | Schmaus et al. | |
| 8,637,538 B1 | 1/2014 | Sciascia | |
| 8,765,175 B2 | 7/2014 | Baichwal et al. | |
| 8,771,732 B2 | 7/2014 | Baichwal et al. | |
| 8,940,753 B1 | 1/2015 | Sciascia | |
| 8,987,289 B2 | 3/2015 | Sciascia | |
| 9,186,330 B2 | 11/2015 | Baichwal et al. | |
| 9,289,423 B2 | 3/2016 | Mouradian et al. | |
| 9,351,938 B2 | 5/2016 | Baichwal et al. | |
| 9,918,980 B2 | 3/2018 | Mouradian et al. | |
| 10,238,646 B2 | 3/2019 | Sciascia | |
| 10,736,889 B2 | 8/2020 | Mouradian et al. | |
| 11,660,296 B2 | 5/2023 | Sciascia | |
| 2001/0006967 A1 | 7/2001 | Crain et al. | |
| 2001/0047005 A1 | 11/2001 | Farrar | |
| 2002/0013296 A1 | 1/2002 | Zhang et al. | |
| 2002/0068692 A1 | 6/2002 | Willis | |
| 2003/0054030 A1 | 3/2003 | Gordon | |
| 2003/0105120 A1 | 6/2003 | Hu et al. | |
| 2003/0149066 A1 | 8/2003 | Levine | |
| 2003/0191147 A1 | 10/2003 | Sherman et al. | |
| 2004/0024003 A1 | 2/2004 | Asmussen et al. | |
| 2004/0157913 A1 | 8/2004 | Jacob et al. | |
| 2004/0171631 A1 | 9/2004 | Hu et al. | |
| 2004/0186111 A1 | 9/2004 | Sun et al. | |
| 2004/0241101 A1 | 12/2004 | Baran, Jr. et al. | |
| 2004/0266806 A1 | 12/2004 | Sanghvi et al. | |
| 2005/0137141 A1 | 6/2005 | Hilfinger | |
| 2005/0182258 A1 | 8/2005 | Schmidhammer et al. | |
| 2006/0063792 A1 | 3/2006 | Dolle et al. | |
| 2006/0194826 A1 | 8/2006 | Oshlack et al. | |
| 2007/0048376 A1 | 3/2007 | Baichwal et al. | |
| 2007/0060501 A1 | 3/2007 | Jhamandas et al. | |
| 2007/0099946 A1 | 5/2007 | Doshan et al. | |

(Continued)

FOREIGN PATENT DOCUMENTS

| | | |
|---|---|---|
| CA | 2822528 A1 | 7/2012 |
| CN | 1107333 A | 8/1995 |

(Continued)

OTHER PUBLICATIONS

International Search Report and Written Opinion in International Application No. PCT/US2013/075096, mailed Apr. 14, 2014, 7 pages.
International Preliminary Report on Patentability in International Application No. PCT/US2013/075096, dated Jun. 16, 2015, 6 pages.
International Search Report and Written Opinion in International Application No. PCT/US2015/035650, mailed Sep. 4, 2015, 9 pages.
International Preliminary Report on Patentability for International Application No. PCT/US2015/035650, dated Dec. 15, 2016, 6 pages.
International Search Report and Written Opinion in International Application No. PCT/US2017/012530, mailed Mar. 20, 2017, 19 pages.

(Continued)

*Primary Examiner* — Charanjit Aulakh
(74) *Attorney, Agent, or Firm* — COOLEY LLP

(57) ABSTRACT

Provided herein are methods of treating nalbuphine-treatable disorders in a hepatically impaired patient.

30 Claims, 8 Drawing Sheets

(56) References Cited

U.S. PATENT DOCUMENTS

| | | |
|---|---|---|
| 2008/0160092 A1 | 7/2008 | Batycky et al. |
| 2008/0176884 A1 | 7/2008 | Perez et al. |
| 2008/0207667 A1 | 8/2008 | Rhame |
| 2008/0207669 A1 | 8/2008 | Perez et al. |
| 2008/0234306 A1 | 9/2008 | Perez et al. |
| 2008/0242720 A1 | 10/2008 | Mangel et al. |
| 2008/0275074 A1 | 11/2008 | Zumimoto et al. |
| 2009/0030026 A1 | 1/2009 | Baichwal et al. |
| 2009/0060871 A1 | 3/2009 | Voronkov et al. |
| 2009/0093509 A1 | 4/2009 | Nazir et al. |
| 2009/0131466 A1 | 5/2009 | Liang et al. |
| 2009/0209569 A1 | 8/2009 | Arnelle et al. |
| 2009/0220583 A1 | 9/2009 | Pereswetoff-Morath et al. |
| 2009/0247635 A1 | 10/2009 | Ehrenpreis |
| 2009/0312359 A1 | 12/2009 | Foss et al. |
| 2010/0150854 A1 | 6/2010 | Schmaus et al. |
| 2010/0227876 A1 | 9/2010 | Rech |
| 2010/0261746 A1 | 10/2010 | Sanghvi et al. |
| 2010/0329984 A1 | 12/2010 | Weers et al. |
| 2011/0067697 A1 | 3/2011 | Lellouche et al. |
| 2011/0190331 A1 | 8/2011 | Avey et al. |
| 2011/0262446 A1 | 10/2011 | Cohen |
| 2012/0040009 A1 | 2/2012 | Hermann |
| 2012/0077803 A1 | 3/2012 | Stuetz et al. |
| 2012/0289470 A1 | 11/2012 | Heit et al. |
| 2013/0203797 A1 | 8/2013 | Kobayashi et al. |
| 2014/0171459 A1 | 6/2014 | Sciascia |
| 2014/0179727 A1 | 6/2014 | Sciascia |
| 2014/0186437 A1 | 7/2014 | Schoenhard |
| 2014/0221415 A1 | 8/2014 | Mouradian et al. |
| 2014/0350042 A1 | 11/2014 | Sciascia |
| 2015/0197545 A1 | 7/2015 | Schteingart et al. |
| 2015/0359789 A1 | 12/2015 | Sciascia |
| 2016/0151359 A1 | 6/2016 | Mouradian et al. |
| 2016/0346273 A1 | 12/2016 | Sciascia |
| 2017/0000782 A1 | 1/2017 | Sciascia |
| 2017/0216277 A1 | 8/2017 | Sciascia |
| 2017/0326142 A1 | 11/2017 | Ford et al. |
| 2018/0008592 A1 | 1/2018 | Sciascia et al. |
| 2018/0125840 A1 | 5/2018 | Sciascia et al. |
| 2018/0185355 A1 | 7/2018 | Mouradian et al. |
| 2018/0193259 A1 | 7/2018 | Gerhart et al. |
| 2019/0099416 A1 | 4/2019 | Sciascia |
| 2019/0117576 A1 | 4/2019 | Baichwal et al. |
| 2020/0016150 A1 | 1/2020 | Sciascia et al. |
| 2020/0022974 A1* | 1/2020 | Jegga et al. ......... A61K 31/485 514/282 |
| 2022/0218697 A1 | 7/2022 | Sciascia |
| 2022/0257590 A1 | 8/2022 | Mouradian |
| 2022/0347171 A1 | 11/2022 | Sciascia et al. |
| 2022/0409613 A1 | 12/2022 | Sciascia |
| 2023/0338367 A1 | 10/2023 | Sciascia et al. |

FOREIGN PATENT DOCUMENTS

| | | |
|---|---|---|
| CN | 1214634 A | 4/1999 |
| CN | 1370082 A | 9/2002 |
| CN | 1835768 A | 9/2006 |
| CN | 104981246 A | 10/2015 |
| CN | 105560202 A | 5/2016 |
| EP | 0615756 A1 | 9/1994 |
| EP | 1149836 A1 | 10/2001 |
| EP | 2402005 A1 | 1/2012 |
| JP | 2001-163784 | 6/2001 |
| JP | 2002-520362 A | 7/2002 |
| JP | 2003-506385 A | 2/2003 |
| JP | 2004-535419 A | 11/2004 |
| JP | 2005162736 A | 6/2005 |
| JP | 2008-502603 | 1/2008 |
| JP | 2008-109898 | 5/2008 |
| JP | 2009-167198 A | 7/2009 |
| JP | 2016-506398 A | 3/2016 |
| JP | 2017-517553 A | 6/2017 |
| JP | 2019532112 A | 11/2019 |
| KR | 10-2015-0093702 A | 8/2015 |
| WO | WO 1984/000889 A1 | 3/1984 |
| WO | WO 98/23290 A1 | 6/1998 |
| WO | WO-0003715 A1 | 1/2000 |
| WO | WO-0143728 A1 | 6/2001 |
| WO | WO 2002/009768 A2 | 2/2002 |
| WO | WO 2002/087582 A1 | 11/2002 |
| WO | WO-03084504 A2 | 10/2003 |
| WO | WO-2004008099 A2 | 1/2004 |
| WO | WO-2004012715 A1 | 2/2004 |
| WO | WO 2004/091623 A1 | 10/2004 |
| WO | WO-2004099249 A2 | 11/2004 |
| WO | WO 2005/009377 A2 | 2/2005 |
| WO | WO-2005058286 A1 | 6/2005 |
| WO | WO 2005/117871 A2 | 12/2005 |
| WO | WO 2007/022535 A2 | 2/2007 |
| WO | WO 2007/025005 A2 | 3/2007 |
| WO | WO 2007/127683 A2 | 11/2007 |
| WO | WO 2008/024490 A2 | 2/2008 |
| WO | WO 2008/129000 A1 | 10/2008 |
| WO | WO 2009/047562 A1 | 4/2009 |
| WO | WO 2009/070733 A1 | 6/2009 |
| WO | WO 2009/092071 A2 | 7/2009 |
| WO | WO 2009/132313 A2 | 10/2009 |
| WO | WO 2010/107457 A1 | 9/2010 |
| WO | WO 2010/112942 A1 | 10/2010 |
| WO | WO 2011/007247 A1 | 1/2011 |
| WO | WO 2011/083304 A1 | 7/2011 |
| WO | WO 2011/117306 A1 | 9/2011 |
| WO | WO 2012/022919 A2 | 2/2012 |
| WO | WO 2012/052169 A2 | 4/2012 |
| WO | WO 2012/089738 A1 | 7/2012 |
| WO | WO 2012/149113 A1 | 11/2012 |
| WO | WO-2013004999 A1 | 1/2013 |
| WO | WO 2014/093871 A1 | 6/2014 |
| WO | WO 2015/191686 A1 | 12/2015 |
| WO | WO 2015/192071 A1 | 12/2015 |
| WO | WO 2017/108041 A1 | 6/2017 |
| WO | WO 2017/108917 A1 | 6/2017 |
| WO | WO 2017/120468 A1 | 7/2017 |
| WO | WO-2017118584 A1 | 7/2017 |
| WO | WO 2017/165409 A1 | 9/2017 |
| WO | WO 2018/005695 A1 | 1/2018 |
| WO | WO-2018013788 A1 | 1/2018 |
| WO | WO-2018044942 A1 | 3/2018 |
| WO | WO 2018/081273 A1 | 5/2018 |
| WO | WO 2020/014342 A1 | 1/2020 |
| WO | WO 2020/023486 A1 * | 1/2020 ........... A61K 31/485 |
| WO | WO 2021/142288 A1 | 7/2021 |
| WO | WO-2024020598 A1 | 1/2024 |

OTHER PUBLICATIONS

International Search Report and Written Opinion in International Application No. PCT/US2017/023398, mailed May 25, 2017, 12 pages.

International Search Report and Written Opinion in International Application No. PCT/US2017/058294, mailed Dec. 18, 2017, 11 pages.

International Search Report and Written Opinion in International Application No. PCT/US2019/041177, mailed Nov. 19, 2019, 5 pages.

International Search Report and Written Opinion in International Application No. PCT/US2019/042994, mailed Nov. 15, 2019, 24 pages.

International Search Report and Written Opinion in International Application No. PCT/US2021/012734, mailed Apr. 1, 2021, 18 pages.

European Application No. 13863494.4, Extended European Search Report dated Apr. 12, 2016, 7 pages.

Extended European Search Report for European Application No. 17770981.3, dated Oct. 1, 2019, 10 pages.

Supplementary European Search Report for European Application No. 17863420.0, dated Jun. 8, 2020, 6 pages.

Extended European Search Report for European Application No. 19840931.0, dated Mar. 29, 2022, 9 pages.

(56) References Cited

OTHER PUBLICATIONS

Extended European Search Report for European U.S. Appl. No. 12/777,826, dated Oct. 20, 2014.
"A Study of Nalbuphine (Extended Release) ER in Idiopathic Pulmonary Fibrosis (IPF) for Treatment of Cough (CANAL)," ClinicalTrials.gov, Jul. 23, 2019, retrieved from URL <https://www.clinicaltrials.gov/ct2/show/NCT04030026>, 8 pages.
Aubert I. et al., "Enhanced preproenkephalin-B-derived opioid transmission in striatum and subthalamic nucleus converges upon globus pallidus internalis in L-dopa-induced dyskinesia" Biol Psychiatry, Apr. 2007, vol. 61, No. 7, pp. 836-844 {Abstract}.
Aungst, B. et al., "Prodrugs for improved oral nalbuphine bioavailability: inter-species differences in the disposition of nalbuphine and its acetylsalicylate and anthranilate esters," International Journal of Pharmaceutics, Aug. 1987, vol. 38, issues 1-3, pp. 199-209 (Abstract).
Bacci et al., "Evaluation of a respiratory symptom diary for clinical studies of idiopathic pulmonary fibrosis," Respiratory Medicine (2018) 134: 130-138.
Bakker, et al., "Bullous pemphigoid as pruritus in the elderly: a common presentation." JAMA Dermatology, Aug. 2013 vol. 149, No. 8, pp. 950-953 (abstract), 2 pages.
Benyamin R. et al., "Opioid Complications and Side Effects," Pain Physician 2008, Opioid Special Issue: vol. 11, pp. S105-S120.
Berg D. et al., "Reduction of Dyskinesia and Induction of Akinesia Induced by Morphine in Two Parkinsonian Patients With Severe Sciatica," J Neural Transm, 1999, vol. 106, No. 7-8, pp. 725-728 {Abstract}.
Bergasa, N., "An approach to the management of the pruritus of cholestasis," Clin Liver Dis 8 (2004) 55-66.
Bergasa, N., "Medical Palliation of the Jaundiced Patient with Pruritus," Gastroenterol Clin N Am 35 (2006) 113-123.
Bernstein, J. et al., "Butorphanol-induced pruritus antagonized by naloxone," J Am Acad Dermatol, 5[2]:227-228 (1981).
Bigliardi et al., "Peripheral Opiate Receptor System in Human Epidermis and Itch", Itch Basic Mechanism and Therapy, 10:97-106 (2004).
Bodnar, RJ, et al., "Endogenous Opiates and Behavior: 2001," Peptides, Dec. 2002, vol. 23, No. 12, pp. 2307-2365 (Abstract).
Borgeat, A. et al., "The effect of nalbuphine and droperidol on spontaneous movements during induction of anesthesia , with propofol in children" J_ of Clinical Anesthesia, Butterworth Publishers, Stoneham, GB, vol. 5, No. 1, 1993, pp. 12-15.
Brotchie, JM, "Nondopaminergic Mechanisms in Levodopa-Induced Dyskinesia," Mov Disord, 2005, vol. 20, No. 8, pp. 919-931 (Abstract).
Bruni, E. et al., "Phototherapy of generalized prurigo nodularis", Journal compilation, British Association of Dermatologists, Clinical and Experimental Dermatology, 35, 549-550 (2009).
Butelman et al., "Kappa-Opioid Receptor Binding Populations in Rhesus Monkey Brain: Relationship to an Assay of Thermal Antinociception," J. Pharmacol. Exp. Ther. 285(2):595-601 (1998).
Calon F., et al., "Increase of Preproenkephalin mRNA Levels in the Putamen of Parkinson Disease Patients With Levodopa-Induced Dyskinesias," J Neuropathol Exp Neurol, 2002, vol. 61, No. 2, pp. 186-196 (Abstract).
Cao X., et al., "Striatal Overexpression of Delta FosB Reproduces Chronic Levodopa-Induced Involuntary Movements," J Neuroscience, May 2010, vol. 30, No. 21, pp. 7335-7343.
Cao X., et al., "Blockade of Cannabinoid Type 1 Receptors Augments the Antiparkinsonian Action of Levodopa Without Affecting Dyskinesias in MPTP-Treated Rhesus Monkeys," J Pharmacol Exp Ther, 2007, vol. 323, No. 1, pp. 318-326.
Carstens et al., "Animal Models of Itch: Scratching Away at the Problem", Itch: Basic Mechanisms and Therapy, Yosipovitch et al., Eds., Marcel Dekker Inc, New York, pp. 35-50 (2004).
Cenci, M.A. et al., "Maladaptive Striatal Plasticity in L-DOPA-Induced Dyskinesia," Prog Brain Res, 2010, vol. 183, pp. 209-233.
Cohen et al., "Nalbuphine is better than naloxone for treatment of side effects after epidural morphine," Anesth Analg. 75(5):747-52 (1992).
Cox H., et al., "The Selective Kappa-Opioid Receptor Agonist U50,488 Reduces L-Dopa-Induced Dyskinesias But Worsens Parkinsonism in MPTP-Treated Primates," Exp Neurol, 2007, vol. 205, No. 1, pp. 101-107.
Davies et al., "A Blinded Study Using Nalbuphine for Prevention of Pruritus Induced by Epidural Fentanyl," Anesthesiology 69(5): 763-765 (1998).
Dawn et al., "Butorphanol for treatment of intractable pruritus," J Am Acad Dermatol 54(3):527-531 (2006).
De Souza et al., "Nalbuphine: An Autoradiographic Opioid Receptor Binding Proofile in the Central Nervous System of an Agonist/Antagonist Analgesic, " The Journal of Pharmacology and Experimental Therapeutics, 1988, vol. 244, No. 1, pp. 391-402.
Dworkin et al., "Phamacologic management of neuropathic pain: Evidence-based recommendations", International Assoc for the Study of Pain, pp. 237-251 (2007).
Encarnacion, E. V., et al., "Levodopa-Induced Dyskinesias in Parkinson's Disease: Etiology, Impact on Quality of Life, and Treatments," European Neurology, vol. 60, No. 2, May 15, 2008, pp. 57-66.
Engber, TM, et al., "Levodopa Replacement Therapy Alters Enzyme Activities in Striatum and Neuropeptide Content in Striatal Output Regions of 6-Hydroxydopamine Lesioned Rats," Brain Res, Jun. 1991, vol. 552. No. 1, pp. 113-118 (Abstract).
Errick, JK and Heel, RC, "Nalbuphine. A Preliminary Review of its Pharmacological Properties and Therapeutic Efficacy," Drugs, Sep. 1983, vol. 26, No. 3, pp. 191-211 (Abstract).
European Association for the Study of the Liver, "EASL Clinical Practice Guidelines: Management of cholestatic liver diseases," Journal of Hepatology 51 (2009) 237-267.
European Association for the Study of the Liver, "EASL Clinical Practice Guidelines: The diagnosis and management of patients with primary biliary cholangitis," Journal of Hepatology, 2017, vol. 67, pp. 145-172.
European Medicines Agency (2010) "Public summary of opinion on orphan designation (−)-17-(cyclopropylmethyl)-3,14 β-dihydroxy-4,5 α-epoxy-6β-[N-methyl-trans-3-(3-furyl) acrylamido] morphinan hydrochloride (intravenous use) for the treatment of uremic pruritus," http://www.ema.europa.eu/docs/en_GB/document_library/Orphan_designation/2009/10/WC500005585.pdf.
European Patent Application No. 15807379.1, Supplementary European Search Report dated Dec. 7, 2017, 10 pages.
Fabbrini, G, et al., "Levodopa-Induced Dyskinesias," Mov Disord, Jul. 2007, vol. 22, No. 10, pp. 1379-1389 (Abstract).
Filho, J. W. et al., Prurigo Nodularis of Hyde—An Update—Journal of the European Academy of Dermatology and Venereology, 14(2):75-82 (2000).
Fox S, et al. "Non-Subtype-Selective Opioid Receptor Antagonism in Treatment of Levodopa-Induced Motor Complications in Parkinson's Disease," Mov Disord, May 2004, vol. 19, No. 5, pp. 554-560 (Abstract).
Fujii et al., "Essential structure of opioid κ receptor agonist nalfurafine for binding to the κ receptor 3: Synthesis of decahydro(iminoethano)phenanthrene derivatives with an oxygen functionality at the 3-position and their pharmacologies," Bioorg. Med. Chem. Lett., 22:7711-7714 (2012).
Gerak et al., "Antinociceptive and Respiratory Effects of Nalbuphine in Rhesus Monkeys," J. Pharmacol. Exp. Ther., 271(2):993-999 (1994).
Gharagozlou, P. et al., "Activation profiles of opioid ligands in HEK cells expressing delta opioid receptors," BMC Neurosci., 2002, 3:19.
Gharagozlou et al., "Activity of opioid ligands in cells expressing cloned u opioid receptors," BMC Pharmacol. 3:1, (2003).
Gharagozlou et al., "Pharmacological profiles of opioid ligands at Kappa opioid receptors," BMC Pharmacol. 6:3, (2006).
Giuffra M., et al., "Dynorphin Agonist Therapy of Parkinson's Disease," Clin Neuropharmacol, Oct. 1993, vol. 16, No. 5, pp. 444-447 (Abstract).
Grunblatt E., et al., "Transcriptional Alterations Under Continuous or Pulsatile Dopaminergic Treatment in Dyskinetic Rats," J Neural Transm, Dec. 2011, vol. 118, No. 12, pp. 1717-1725, epub Dec. 25, 2010.

(56) References Cited

OTHER PUBLICATIONS

Gunion et al., "Use of the Mixed Agonist-Antagonist Nalbuphine in Opioid Based Analgesia," Elsevier, 2004, vol. 6, pp. 29-39.
Gutstein et al., "Chapter 23: Opioid Analgesics" in: Goodman & Gilman's The Pharmacologic Basis of Therapeutics. 10th Ed., Hardman et al., Eds., McGraw Hill, pp. 569-619 (2001).
Han, RY, et al., "Mucoadhesive Buccal Disks for Novel Nalbuphine Prodrug Controlled Delivery: Effect of Formulation Variables on Drug Release and Mucoadhesive Performance," Int J Pharm, Jan. 1999, vol. 177, No. 2, pp. 201-209 (Abstract).
Hawi, A., et al., "A proof-of-concept study with pharmacokinetics demonstrating anti-pruritic activity of oral nalbuphine in hemodialysis patients with uremic pruritus." Trevi Therapeutics Exhibits Poster at 2014 Annual Meeting of the Society for Investigative Dermatology. Biotech Week, May 28, 2014 (May 28, 2014), p. 1522, XP55429305, Retrieved from the Internet: URL:http://www.trevitherapeutics.com/ckfinder/userfiles/files/SIDposter Trevi Therapeutics 567.pdf [retrieved on Nov. 27, 2017], 1 page.
Hawi, A., et al., "Pharmacokinetics of nalbuphine hydrochloride extended release tablets in hemodialysis patients with exploratory effect on pruritus." BMC Nephrology (2015); 16: 47.
Henry B. et al., "Increased Strialal Pre-Proenkephalin B Expression is Associated with Dyskinesia in Parkinson's Disease," Exp Neurol, Oct. 2003, vol. 183, No. 2, pp. 458-468 (Abstract).
Henry B. et al., "Mu- and Delta-Opioid Receptor Antagonists Reduce Levodopa-Induced Dyskinesia in the MPTP-Lesioned Primate Model of Parkinson's Disease," Exp Neurol, Sep. 2001, vol. 171, No. 1, pp. 139-146 (Abstract).
Herrero MT, et al. "Effects of L-DOPA on Preproenkephalin and Preprotachykinin Gene Expression in the MPTP-Trealed Monkey Striatum," Neuroscience, Oct. 1995, vol. 68, No. 4, pp. 1189-1198 (Abstract).
History of Changes for Study: NCT02143973, ClinicalTrials.gov archive [online], Mar. 18, 2016, [Retrieved on Jan. 20, 2021], Internet, URL, https://www.clinicaltrials.gov/ct2/history/NCT02143973?V_8=View#StudyPageTop.
History of Changes for Study: NCT02143648, ClinicalTrials.gov archive [online], Feb. 22, 2016, [Retrieved on Jan. 20, 2021], Internet, URL, https://www.clinicaltrials.gov/ct2/history/NCT02143648?V_12=View#StudyPageTop.
Houde Br. J. Clin. Pharmac. (1979), 7, 297S-308S (Year: 1979).
Huang, et al., "The Effects of Electrically Assisted Methods on Transdermal Delivery of Nalbuphine Benzoate and Sebacoyl Dinalbuphine Esler From Solutions and Hydrogels, " Int J Pharm, Jun. 2005, vol. 297, No. 1 -2, pp. 162-171 (Abstract).
Ikeda K, et al. "TRK-820, a Selective Kappa Opioid Receptor Agonist, Could Effectively Ameliorate L-DOPA-Induced Dyskinesia Symptoms in a Rat Model of Parkinson's Disease," Eur J Pharmacol, Oct. 2009, vol. 620, No. 1-3, pp. 42-48 (Abstract).
Iking, et al., "Prurigo as a symptom of atopic and non-atopic diseases: aetiological survey in a consecutive cohort of 108 patients." Journal of the European Academy of Dermatology and Venereology (2013); 27(5):550-557.
Jenner P., "Molecular Mechanisms of L-DOPA-Induced Dyskinesia," Nat Rev Neurosci, Sep. 2008, vol. 9, No. 9, pp. 665-677 (Abstract).
Johansson PA, et al., "Alterations in Cortical and Basal Ganglia Levels of Opioid Receptor Binding in a Rat Model of I-DOPA-Induced Dyskinesia," Neurobiol Dis, Apr. 2001, vol. 8, No. 2, pp. 220-239 (Abstract).
Jung, S., II et al., "Efficacy of Naltrexone in the Treatment of Chronic Refractory Itching in Burn Patients: Preliminary Report of an Open Trial," J. of Burn Care & Research, 30[2]:257-260 (2009).
Kamimura et al., "Long-term efficacy and safety of nalfurafine hydrochloride on pruritus in chronic liver disease patients: Patient-reported outcome based analyses," PLoS ONE (2017) 12(6): e0178991, 11 pages.
Kanavy, H. et al., "Treatment of Refractory Prurigo Nodularis With Lenalidomide", The Cutting Edge: Challenges in Medical and Surgical Therapies, Archives of Dermatology, 148(7):794-796 (2012).

Keithi-Reddy et al., "Uremic Pruritus," Kidney International, 72:373-377 (2007).
Kendrick et al., "Naloxone versus nalbuphine infusion for prophylaxis of epidural morphine-induced pruritus", Anesth. Analg., 82(3):641-7 (1996).
Kfoury et al., "Uremic pruritus," J. Nephrol,. 25(5):644-652 (2011).
King, Jr., et al., "Idiopathic Pulmonary Fibrosis: Relationship between Histopathologic Features and Mortality," Am. J. Respir. Crit. Care Med., 2001, 164, pp. 1025-1032.
Kjellberg et al., "Pharmacological control of opioid-induced pruritus: a quantitative systematic review of randomized trials", European J. of Anaesthesiology, 18(6): 46-357 (2001).
Klintenberg R., et al., "Naloxone Reduces Levodopa-Induced Dyskinesias and Apomorphine-Induced Rotations in Primate Models of Parkinsonism," J Neural Transm, Oct. 2002, vol. 109, No. 10, pp. 1295-1307 (Abstract).
Koprich JB, et al., "The Selective Mu-Opioid Receptor Antagonist ADL5510 Reduces Levodopa-Induced Dyskinesia Without Affecting Antiparkinsonian Action in MPTP-Lesioned Macaque Model of Parkinson's Disease," Mov Disord, Jun. 2011, vol. 26, No. 7, pp. 1225-1233, EPub Apr. 4, 2011 (Abstract).
Kremer et al., "Pathogenesis and Treatment of Pruritus in Cholestasis," Drugs 2008; 68(15): 2163-2182.
Kumada et al., "Efficacy of nalfurafine hydrochloride in patients with chronic liver disease with refractory pruritus: A randomized, doubleblind trial," Hepatology Research 2017; 47: 972-982.
Kumagai et al., "Prospects for a novel kappa-opioid receptor agonist, TRK-820 in uremic pruritus," in: Itch, Basic Mechanisms and Therapy, Yosipovitch et al., Eds., Marcel Dekker Inc, New York, pp. 279-286 (2004).
Kumar et al., "Long-Term Effects of Nalbuphine ER Tablets in Hemodialysis Patients With Uremic Pruritus: A Multicenter Open-Label Trial," American Journal of Kidney Diseases, 2016, vol. 67, No. 5, Abstrat 184, p. A64.
Kumar et al., "Nalbuphine ER Tablets in Hemodialysis Patients With Severe Uremic Pruritus: Multicenter, Randomized, Double-Blind, Placebo-Controlled Trial," American Journal of Kidney Diseases, 2016, vol. 67, No. 5, Abtract 185, p. A65.
Lalley, P., "Opioidergic And Dopaminergic Modulation of Respiration," Respir Physiol Neurobiol., 2008, 164(1-2): 160-167.
Lawnhorn et al., "Epidural Morphine With Butorphanol for Postoperative Analgesia After Cesarean Delivery," Anesth. Analg. 72:53-57 (1991).
Lee et al., "Effects of Butorphanol on Morphine-induced Itch and Analgesia in Primates," Anesthesiology 107(3): 478-485 (2007).
Lee, M. R. et al., "Prurigo nodularis: A review", Australasian J. of Dermatology, 46:211-220 (2005).
Leidy et al., "Measuring respiratory symptoms of COPD: performance of the EXACT—Respiratory Symptoms Tool (E-RS) in three clinical trials," Respiratory Research 2014, 15:124, 10 pages.
Levy, C., "Management of Pruritus in Patients with Cholestatic Liver Disease," Gastroenterology & Hepatology, Sep. 2011, vol. 7, Issue 9, pp. 615-617.
Liao, Chia-Chih, et al. "Efficacy of intramuscular nalbuphine versus diphenhydramine for the prevention of epidural morphine-induced pruritus after cesarean delivery." Chang Gung Med J (2011); 34.2: 172-178.
Lindor et al., "Primary Biliary Cirrhosis," Hepatology, Jul. 2009, vol. 50, No. 1, pp. 291-308.
Liu, Fl, et al. "Biodegradable Polymeric Microspheres for Nalbuphine Prodrug Controlled Delivery: In Nitro Characterization and in Vivo Pharmacokinelic Studies," Int J Pharm, May 2003, vol. 257, No. 1-2, pp. 23-31 (Abstract).
Mahler and O'Donnell, "Recent Advances in Dyspnea," Chest. 2015; 147(1):232-241.
Malgorzata et al., "Understanding Pruritus in Systemic Disease," Journal of Pain and Symptom Management, 21(2):151-168 (2001).
Mansour A, et al. "Mu, Delta, and Kappa Opioid Receptor mRNA Expression in the Rat CNS: an In Situ Hybridization Study," J Comp Neurol, Dec. 1994, vol. 350, No. 3, pp. 412-438 (Abstract).
Mazzone et al., "Mapping supramedullary pathways involved in cough using functional brain imaging: Comparison with pain," Pulm Pharmacol Ther., 2009; 22(2): 90-96.

(56) References Cited

OTHER PUBLICATIONS

Mela et al., "Review article: pruritus in cholestatic and other liver diseases," Aliment Pharmacol Ther 2003; 17: 857-870.
Metze, D. et al., "Efficacy and safety of naltrexone, an oral opiate receptor antagonist, in the treatment of pruritus in internal and dermatological diseases", J .Am Acad Dermatol, 41 [4]:533-539 (1999).
Montgomery, Clinical Trial: "Nalbuphine for the Treatment of Opioid Induced Pruritus in Children," Dec. 20, 2013, 3 pages, http://clinicaltrials.gov/show/NCT00323154.
Morice et al., "Expert opinion on the cough hypersensitivity syndrome in respiratory medicine," Eur Respir J 2014; 44:1132-1148.
Mouradian MM, et al., "Pathogenesis of Dyskinesias in Parkinson's Disease," Ann Neurol, May 1989, vol. 25, No. 5, pp. 523-526 (Abstract).
Mouradian MM, et al., "Modification of Central Dopaminergic Mechanisms by Continuous Levodopa Therapy for Advanced Parkinson's Disease," Ann Neurol, Jan. 1990, vol. 27, No. 1, pp. 18-23 (Abstract).
Nagase et al., "Essential structure of opioid κ receptor agonist nalfurafine for binding to the κ receptor 2: Synthesis of decahydro(iminoethano)phenanthrene derivatives and their pharmacologies," Bioorg. Med. Chem. Lett. 22:5071-5074 (2012).
Naini et al., G., "A Promising Drug for the Treatment of Uremic Pruritus", Saudi J. Kidney Dis. Transpl., 18:378-381(2007).
Nisbet AP, et al., "Preproenkephalin and Preprotachykinin Messenger RNA Expression in Normal Human Basal Ganglia and in Parkinson's Disease," Neuroscience, May 1995, vol. 66, No. 2, pp. 361-376 (Abstract).
Oeda et al., "Prevalence of pruritus in patients with chronic liver disease: A multicenter study," Hepatology Research 2018; 48: E252-E262.
Pallasch et al., "Butorphanol and nalbuphine: A pharmacologic comparison," Oral Surgery, Oral Medicine, Oral Pathology, Jan. 1985, 59(1):15-20.
Pan, "μ-Opposing actions of the k-opioid receptor," Trends in Pharmacological Sciences 19:94-98 (1998).
Pao, LH, et al., "High-Performance Liquid Chromatographic Method for the Simultaneous Determination of Nalbuphine and Its Prodrug, Sebacoyl Dinalbuphine Ester, in Dog Plasma and Application to Pharmacokinetic Studies in Dogs," J Chromatogr B Biomed Sci Appl, Sep. 2000, vol. 746, No. 2, pp. 241-247 (Abstract).
Papa SM, et al., "Motor Fluctuations in Levodopa Treated Parkinsonian Rats: Relation to Lesion Extent and Treatment Duration," Brain Res, Oct. 1994, vol. 662, No. 1-2, pp. 69-74 (Abstract).
Papa SM and Chase TN, "Levodopa-Induced Dyskinesias Improved by a Glutamate Antagonist in Parkinsonian Monkeys," Ann Neurol, May 1996, vol. 39, No. 5, pp. 574-578 (Abstract).
Patel et al., "An update on pruritus associated with CKD," Am J Kidney Dis 50: 11-20 (2007).
Pauli-Magnus et al., "Naltrexone Does Not Relieve Uremic Pruritus: Results of a Randomized, Double-Blind, Placebo-Controlled Crossover Study," J. Am. Soc. Nephrol. 11:514-519 (2000).
Peer et al., "Randomised crossover trial of naltrexone in uraemic pruritus", The Lancet, 348[9041]:1552-1554 (1996).
Peng et al., "Pharmacological Properties of Bivalent Ligands Containing Butorphan Linked to Nalbuphine, Naltrexone and Naloxone at μ, δ and κ Opioid Receptors," J. Med. Chem. 50(9):2254-2258 (2007).
Penning et al., "Reversal of epidural morphine-induced respiratory depression and pruritus with nalbuphine," Canadian Journal of Anesthesia 35(6): 599-604 (1988).
Phan et al., "Antipruritic treatment with systemic μ-opioid receptor antagonists: A review," Journal of the American Academy of Dermatology 63(4): 680-688 (2010).
Phan et al., "Systemic Kappa Opioid Receptor Agonists in the Treatment of Chronic Pruritus: A Literature Review," Acta Dermato-Venereologica 92: 555-560 (2012).

Phillips, B., "Movement Disorders: A Sleep Specialist's Perspective," Neurology, Mar. 9, 2004, vol. 62, issue 5, supplement 2, pp. S9-S16 (Abstract).
Piccini P., et al., "Alterations in Opioid Receptor Binding in Parkinson's Disease Patients With Levodopa-Induced Dyskinesias," Ann Neurol, Nov. 1997, vol. 42, No. 5, pp. 720-726 (Abstract).
Potts, L.F, et al., "The Synthetic opioid nalbuphine reduces L-dopa-induced dyskinesia in non-human primates," The Movement Disorder Society MOS 17th International congress of Parkinson's Disease and Movement Disorders, Sydney, Australia, vol. 28, Jun. 2013, pp. 1-2.
Potts et al., "Dual k-Agonist/u-Antagonist Opioid Receptor Modulation Reduces Levodopa-Induced Dyksinesia and Corrects Dysregulated Striatal Changes in the Nonhuman Primate Model of Parkinson Disease," Ann Neurol, vol. 77, 2015, pp. 930-941.
Rascol O, et al., "Naltrexone, An Opiate Antagonist, Fails to Modify Motor Symptoms in Patients With Parkinson's Disease," Mov Disord, Jul. 1994, vol. 9, No. 4, pp. 437-440 (Abstract).
Raghu et al., "Diagnosis of Idiopathic Pulmonary Fibrosis. An Official ATS/ERS/JRS/ALAT Clinical Practice Guideline," Am J Respir Crit Care Med, Sep. 1, 2018, vol. 198, Issue 5, pp. e44-e68.
Reddy et al., "Transdermal Buprenorphine May Be Effective in the Treatment of Pruritus in Primary Biliary Cirrhosis," Journal of Pain and Symptom Management, Nov. 2007, vol. 34, No. 5, pp. 455 and 456.
Rose et al, "Gabapentin: pharmacology and its use in pain management", Anaesthesia, 57(5): 451-462 (2002).
Romagnoli et al., "Ceiling effect for respiratory depression by nalbuphine," Clin. Pharmacol. Ther., vol. 27, No. 4, Apr. 1980, pp. 478-485.
Ryerson et al., "Cough predicts prognosis in idiopathic pulmonary fibrosis," Respirology, (2011) 16:969-975.
Ryerson et al., "Dyspnea in Idiopathic Pulmonary Fibrosis: A Systematic Review," Journal of Pain and Symptom Management, Apr. 2012, 43(4):771-782.
Samadi P, et al., "Opioid Antagonists Increase the Dyskinetic Response to Dopaminergic Agents in Parkinsonian Monkeys: Interaction Between Dopamine and Opioid Systems," Neuropharmacology, Dec. 2003, vol. 45, No. 7, pp. 954-963 (Abstract).
Samadi P, et al., "The Opioid Agonist Morphine Decreases the Dyskinetic Response to Dopaminergic Agents in Parkinsonian Monkeys," Neurobiol Dis, Jun. 2004, vol. 16, No. 1, pp. 246-253 (Abstract).
Sandyk, R., et al., "Attenuation of reserpine-induced catalepsy by melatonin and the role of the opioid system," International J. of Neuroscience, Gordon and Breach, US, vol. 48, No. 3-4, Oct. 1989, pp. 297-301.
Sawada et al., "Amantadine for Dyskinesias in Parkinson's Disease: A Randomized Controlled Trial," PLoS ONE 2010, 5(12); e15298 (Year: 2010).
Schmelz, "Itch-mediators and mechanisms", J. of Dermatological Science, 28:91-96, (2002).
Schmidt et al., "Nalbuphine," Drugs and Alcohol Dependence 14:339-362 (1985).
Schwacha, M. G., "Opiates and the Development of Post-Injury Complications: a Review", Int. J. Clin. Exp. Med., 1:42-49 (2008).
Simons, "Advances in $H_1$-Antihistamines." N Engl J Med (2004); 351(21): 2203-2217.
Somrat, C., et al. "Optimal Dose of Nalbuphine for Treatment of Intrathecal-Morphine Induced Pruritus after Caesarean Section." Journal of Obstetrics and Gynaecology Research (1999); 25.3: 209-213.
Spring, P. et al., "Prurigo nodularis: retrospective study of 13 cases managed with methotrexate", Clinical and Experimental Dermatology, 39:468-473 (2014).
Stander, S. et al. "Treatment of Pruritus in Internal and Dermatological Diseases with Opioid Receptor Antagonists", Itch, Basic Mechanisms and Therapy, Michael Dekker, Inc., New York, pp. 259-277 (2004).
Stander, S. et al. "Targeting the Neurokinin Receptor 1 with Aprepitant: A Novel Antipruritic Strategy", PLoS ONE 5(6):1-5 (2010).

(56) References Cited

OTHER PUBLICATIONS

Steinhoff, M. et al. "Modern Aspects of Cutaneous Neurogenic Inflammation", Archives of Dermatology (2003); 139.11: 1479-1488.
Sung, KC, et al. "Transdermal Delivery of Nalbuphine and Its Prodrugs by Electroporation," Eur J Pharm Sci, Jan. 2003, vol. 18, No. 1, pp. 63-70 (Abstract).
Sung, KC, et al., "Controlled Release of Nalbuphine Prodrugs From Biodegradable Polymeric Matrices: Influence of Prodrug Hydrophilicity and Polymer Composition," International Journal of Pharmaceutics, Apr. 1998, vol. 172, No. 1-2, pp. 17-25 (Abstract).
Tajiri et al., "Recent advances in the management of pruritus in chronic liver diseases," World J Gastroenterol, May 2, 20171; 23(19): 3418-3426.
Trawinska et al., "Patient considerations and drug selection in the treatment of idiopathic pulmonary fibrosis," Therapeutics and Clinical Risk Management 2016:12 563-574.
Trevi Therapeutics Announces Positive Results from Phase 2 Trial in Prurigo Nodularis. Trevi Therapeutics. Oct. 13, 2016. [retrieved on Nov. 22, 2017]. Retrieved from the Internet. <URL: http://www.trevitherapeutics.com/news/view/39>. 3 pages.
Umechi et al., "Involvement of central mu-opioid system in the scratching behavior in mice, and the suppression of it by the activation of kappa-opioid system," Eur. J. Pharmacol. 477(1): 29-35 (2003).
Van Manen et al., "Cough in idiopathic pulmonary fibrosis," Eur Respir Rev 2016; 25:278-286.
Verhagen ML, et al., "Amantadine as Treatment for Dyskinesias and Motor Fluctuations in Parkinson's Disease," Neurology, May 1998, vol. 50, No. 5, pp. 1323-1326 (Abstract).
Vigeland et al., "Etiology and treatment of cough in idiopathic pulmonary fibrosis," Respiratory Medicine (2017) 123:98-104.
Volkow et al., "Opioid Abuse in Chronic Pain—Misconceptions and Mitigation Strategies," N Engl J Med, 2016, 374(13), 1253-1263.
Wang J. J., et al., "A Comparison Among Nalbuphine, Meperidine, and Placebo for Treating Postanesthetic Shivering," Anesthesia & Analgesia, Mar. 1999, vol. 88, No. 3, pp. 686-689 (Abstract).
Wang et al., "Comparison of intravenous nalbuphine infusion versus saline as an adjuvant for epidural morphine," Reg. Anesth. 21(3):214-218 (1996).
Wang et al., "Comparison of Intravenous Nalbuphine Infusion Versus Naloxone in the Prevention of Epidural Morphine-Related Side Effects," Reg. Anesth. Pain Med. 23(5):479-484 (1998).
Wang et al., "Comparison of Pharmacological Activities of Three Distinct κ Ligands (Salvinorin A, TRK-820 and 3FLB) on κ Opioid Receptors in Vitro and Their Antipruritic and Antinociceptive Activities in Vivo," J. Pharmacol. Exp. Ther. 312(1):220-230 (2005).
Wang, JJ, et al. "Submicron Lipid Emulsion as a Drug Delivery System for Nalbuphine and Its Prodrugs," J Control Release, Oct. 2006, vol. 115, No. 2, pp. 140-149 (Abstract).
Westin JE, et al. "Spatiotemporal Pattern of Striatal ERK1/2 Phosphorylation in a Rat Model of L-DOPA-Induced Dyskinesia and the Role of Dopamine D1 Receptors," Biol Psychiatry, Oct. 2007, vol. 62, No. 7, pp. 800-810.
Wittels et al., "Opioid Antagonist Adjuncts to Epidural Morphine for Postcesarean Analgesia: Maternal Outcomes," Anesth. Analg 77:925-32 (1993).
Wikström et al., "κ-Opioid System in Uremic Pruritus: Multicenter, Randomized, Double-Blind, Placebo-Controlled Clinical Studies," Journal of the American Society of Nephrology, 2005, vol. 16, No. 12, pp. 3742-3747.
Yeh et al. "Combination of opioid agonist and agonist-antagonist: patient-controlled analgesia requirement and adverse events among different-ratio morphine and nalbuphine admixtures for postoperative pain," British Journal of Anaesthesia 101 (4): 542-548 (2008).
Yokoyama et al. "Treatment of epidural morphine induced pruritus with butorphanol," English Abstract, Masui, 8(2):178-82 (2009).
Yosipovitch, "Chronic Pruritus: a Paraneoplastic Sign," Dermatol. Ther. 23(6): 590-596 (2010).

Yosipovitch, G. et al., "Chronic Pruritus", N. Eng. J. Med., 368[17]:1625-1634 (2013).
Zylicz et al., "Severe Pruritus of Cholestasis in Disseminated Cancer: Developing a Rational Treatment Strategy. A Case Report," Journal of Pain and Symptom Management, Jan. 2005, vol. 29 No. 1, pp. 100-103.
Extended European Search Report for European Application No. 19834225.5, dated Mar. 16, 2022, 9 pages.
"Oxycontin—oxycodone hydrochloride tablet, film coated, extended release," Purdue Pharma LP, retrieved from <URL:app.purduepharma.com/xmlpublishing/pi.aspx?id=o>, retrieved Mar. 30, 2020, 31 pages.
"Morphine Sulfate extended-release tablets, for oral use, Prescribing Information," US Food and Drug Administration Medication Guide, Oct. 2019, 28 pages.
"Hysingla ER—hydrocodone bitartrate tablet, extended release," Purdue Pharma LP, retrieved from <URL:app.purduepharma.com/xmlpublishing/pi.aspx?id=h>, retrieved Mar. 30, 2020, 21 pages.
Clinical Trial: Open Label Extension Study of Nalbuphine HCl ER in Patients With Prurigo Nodularis, v8 [retrieved from internet on Apr. 5, 2022]. Retrieved from https://www.clinicaltrials.gov/ct2/history/NCT02174432?V_8=View#StudyPageTop.
Clinical Trial: Study of Nalbuphine HCl ER Tablets in Patients With Prurigo Nodularis, v13 [retrieved from internet on Apr. 5, 2022]. Retrieved from https://www.clinicaltrials.gov/ct2/history/NCT02174419?V_13=View#StudyPageTop.
Delcò et al., "Dose Adjustment in Patients with Liver Disease," Drug Safety, 2005, vol. 28, No. 6, p. 529-545.
Gelot et al., "Opioid Dosing in Renal and Hepatic Impairment," Nephrology, Aug. 20, 2014, vol. 39, No. 8, pp. 34-38.
Kotb et al., "Pharmacokinetics of controlled release morphine (MST) in patients with liver cirrhosis, " British Journal of Anaesthesia, 1997, vol. 79, pp. 804-806.
Manen et al., "Cough in idiopathic pulmonary fibrosis," Eur. Respir. Rev., 2016, vol. 25, pp. 278-286.
Canadian Guideline for Safe and Effective Use of Opioids for Chronic Non-Cancer Pain, National Opioid Use Guideline Group (NOUGG), Apr. 30, 2010, 126 pages.
Clinical Trial: "Phase 1 Study of Nalbuphine HCl ER Tablets in Hemodialysis Patients With Uremic Pruritus", ClinicalTrials.gov ID NCT02373215, Sponsor: Trevi Therapeutics, first submitted Feb. 13, 2015, 9 pages.
"Common Terminology Criteria for Adverse Events (CTCAE), Version 4.0", U.S. Department of Health and Human Services, National Institutes of Health, National Cancer Institute, Published: May 28, 2009 (v4.03: Jun. 14, 2010), 196 pages.
International Search Report and Written Opinion for PCT Application No. PCT/US2023/070849 dated Nov. 22, 2023, 11 pages.
Jaillon et al., "Pharmacokinetics of nalbuphine in infants, young healthy volunteers, and elderly patients", Clin Pharmacol Ther. (Aug. 1989) vol. 46, No. 2, p. 226-233.
Petrone, D., et al., "Slowing the titration rate of tramadol HCl reduces the incidence of discontinuation due to nausea and/or vomiting: a double-blind randomized trial", J Clin Pharm Ther. Apr. 1999; 24(2): 115-23.
Ruoff, G. E., "Slowing the initial titration rate of tramadol improves tolerability", Pharmacotherapy. Jan. 1999; 19(1): 88-93.
Weisshaar et al., "Efficacy and safety of oral nalbuphine extended release in prurigo nodularis: results of a phase 2 randomized controlled trial with an open-label extension phase", J Eur Acad Dermatol Venereol. (Nov. 15, 2021) vol. 36, No. 3, p. 453-461.
Allen, S, et al., "Low dose diamorphine reduces breathlessness without causing a fall in oxygen saturation in elderly patients with end-stage idiopathic pulmonary fibrosis", Palliat Med. Mar. 2005; 19(2): 128-30.
Collard et al., "Acute exacerbation of idiopathic pulmonary fibrosis. An international working group report", Am J Respir Crit Care Med, Aug. 1, 2016; 194(3): 265-75.
Combivent® Respimat® (ipratropium bromide and albuterol inhalation spray), for oral inhalation use brochure Initial U.S. Approval: 1996, 17 pages.
"COPD and Asthma: Differential Diagnosis", American Academy of Family Physicians, 2006, 12 pages.

(56) References Cited

OTHER PUBLICATIONS

Co-pending U.S. Appl. No. 17/085,098, inventor Sciascia; Thomas, filed on Oct. 30, 2020.
Co-pending U.S. Appl. No. 17/341,936, inventor Sciascia; Thomas, filed on Jun. 8, 2021.
"Coughing: Controlled Coughing", Cleveland Clinic, Sep. 14, 2018, 9 pages.
Fang et al., "Transdermal Delivery of Nalbuphine and Nalbuphine Pivalate From Hydrogels by Passive Diffusions and Iontophoresis", Arzneimittelforschung, 2001; 51(5): 408-13.
Franklin et al., "Insights into ErbB signaling from the structure of the ErbB2-pertuzumab complex", Cancer Cell, vol. 5, Apr. 2004, pp. 317-328.
Horton M.R et al., "Thalidomide for the treatment of cough in idiopathic pulmonary fibrosis: a randomized trial", Annals of Internal Medicine. (Sep. 18, 2012); 157(6): 398-406.
International Preliminary Report on Patentability for International Application No. PCT/US2021/012734, mailed Jul. 21, 2022, 16 pages.
Invitation to Pay additional fees for International Application No. PCT/US2019/041177, mailed Sep. 10, 2019, 2 pages.
Liu H. et al., "Effects of first and second generation antihistamines on muscarinic induced mucus gland cell ion transport", BMC Pharmacology, Dec. 2005; 5(1): 1-10, Epub Mar. 24, 2005.
Martinez, F.J. et al., "Phase 2B study of inhaled RVT-1601 for chronic cough in idiopathic pulmonary fibrosis: a multicenter, randomized, placebo-controlled study (SCENIC trial)", American Journal of Respiratory and Critical Care Medicine, (May 1, 2022); 205(9): pp. 1084-1092.
Martinez, F.J. et al., "Treatment of persistent cough in subjects with idiopathic pulmonary fibrosis (IPF) with gefapixant, a P2X3 antagonist, in a randomized, placebo-controlled clinical trial", Pulmonary therapy. (Dec. 2021); 7(2): 471-86 E pub date Jun. 21, 2021.
McGarvey L.P., et al., "Efficacy and safety of gefapixant, a P2X3 receptor antagonist, in refractory chronic cough and unexplained chronic cough (COUGH-1 and COUGH-2): results from two double-blind, randomised, parallel-group, placebo-controlled, phase 3 trials", The Lancet. (Mar. 5, 2022); 399(10328): 909-23.
Meltzer, E.B., et al., "Idiopathic pulmonary fibrosis", Orphanet Journal of Rare Diseases, (Mar. 26, 2008); 3(1): 1-5.
Montuschi, P. "Pharmacological treatment of chronic obstructive pulmonary disease", International Journal of Chronic Obstructive Pulmonary Disease. (Dec. 2006); 1(4): 409-424.
Morice A.H., et al., "Opiate therapy in chronic cough", American Journal of Respiratory and Critical Care Medicin., (Feb. 15, 2007); 175(4): 312-315.
Moroni M., et al. "Inhaled sodium cromoglycate to treat cough in advanced lung cancer patients," British Journal of Cancer. (Jul. 1, 1996); 74(2): 309-311.
NUBAIN® label at p. 5 (Warnings, Life-Threatening Respiratory Depression in Patients with Chronic Pulmonary Disease or in Elderly, Cachectic, or Debilitated Patients), 2016, available at: https://www.accessdata.fda.gov/drugsatfda_docs/label/2016/018024s041lbl.pdf, 17 pages.
Patel M. "A review of standard pharmacological therapy for adult asthma—Steps 1 to 5", Chronic Respiratory Disease. May 2015; 12(2): 165-176.
Plantier L. et al., "Physiology of the lung in idiopathic pulmonary fibrosis", European Respiratory Review. (Mar. 31, 2018); 27(147): 1-14.
Prous Science Integrity, "Nalbuphine hydrochloride", Prous Science, 2009, Entry No. 91357, CAS Registry No. 23277-43-2, 1 page.
Ramirez, J.M. et al., "Neuronal mechanisms underlying opioid-induced respiratory depression: our current understanding", Journal of Neurophysiology. (May 1, 2021); 125(5): 1899-1919. Epub Apr. 7, 2021.
"The Voice of the Patient: A series of reports from the U.S. Food and Drug Administration's (FDA's) Patient-Focused Drug Development Initiative, Idiopathic Pulmonary Fibrosis", Center for Drug Evaluation and Research (CDER) U.S. Food and Drug Administration (FDA) Public Meeting Sep. 26, 2014, Report Date: Mar. 2015, 22 pages.
Troy L.K., et al., "Sleep disordered breathing in interstitial lung disease: A review". World Journal of Clinical Cases: WJCC. (Dec. 12, 2014); 2(12): 828-834.
Vajdos et al., "Comprehensive Functional Maps of the Antigen-binding Site of an Anti-ErbB2 Antibody Obtained with Shotgun Scanning Mutagenesis", J Mol Biol, Jul. 5, 2002; 320(2): 415-28.
Valle et al., "287 A phase Ib study of pertuzumab (P), a recombinant humanized anitbody to HER2, and capecitabine (C) in patient with advanced solid tumors", European Journal of Cancer Supplements, vol. 2, No. 8, Sep. 30, 2004, 1 page.
Van Manen M. J.G., et al., "Optimizing quality of life in patients with idiopathic pulmonary fibrosis", Ther Adv Respir Dis. Mar. 2017;11(3): 157-169. Epub Jan. 1, 2017.
Anonymous, "NCT04020016," Aug. 2019, pp. 1-9, Retrieved from the Internet: https://classic.clinicaltrials.govlct2/historyINCT04020016?V3=View#StudyPageTop. 9 pages.
Extended European Search Report for European Application No. 21738479.1 dated Dec. 21, 2023, 10 pages.
Li, Huan, "[Comparison of the post-operative analgesic effect of Dezocine, morphine, nalbuphine for Outpatients Postoperatively]" [translated from Chinese], Chinese Journal of Hospital Pharmacy, vol. 12., 2013, machine translation of abstract only. 2 pages.
Kokubun H., "Opioids are metabolized in the liver, so the dosage should be reduced if liver function is impaired."[translated from Japanese], Nikkei Business Publications, Inc., Jan. 2017, document in Japanese with English abstract, 3 pages.

* cited by examiner

METHODS OF ADMINISTERING NALBUPHINE

This application is a continuation of International Application No. PCT/US2021/012734, filed Jan. 8, 2021, which claims the benefit of priority to U.S. Application Ser. No. 63/014,306, filed Apr. 23, 2020, and U.S. Application Ser. No. 62/959,701, filed Jan. 10, 2020, the contents of each of which are hereby incorporated by reference in their entireties for all purposes.

BACKGROUND

Nalbuphine is a synthetic opioid that acts as a competitive antagonist of the µ-opioid receptor while producing agonist effects at the κ-opioid receptor. Nalbuphine is currently available as a generic medication in an injectable form approved for use in the relief of moderate to severe pain, a supplement to balanced anesthesia, for pre-operative and post-operative analgesia and obstetrical analgesia during labor and delivery. Nalbuphine is hepatically cleared and extensively metabolized in the liver.

Nalbuphine can be used to treat a variety of conditions, including chronic pruritic conditions (such as, prurigo nodularis, uremic pruritus, and chronic liver disease) and neurologically mediated conditions (such as chronic cough and levodopa-induced dyskinesia). Hepatic impairment is a common co-morbidity in many of these nalbuphine-treatable conditions.

Thus, there is a need for safe and effective methods for treating hepatically impaired patients with nalbuphine.

SUMMARY OF THE DISCLOSURE

The present disclosure, among other things, provides methods of treating a nalbuphine-treatable disorder in a hepatically impaired patient, comprising
  (a) determining the patient's Child-Pugh score;
  (b) administering a daily dose of about 15 mg to about 360 mg of nalbuphine, or a pharmaceutically acceptable salt thereof, to a patient with a Child-Pugh score of A; and
  (c) administering a daily dose of about 4 mg to about 120 mg of nalbuphine, or a pharmaceutically acceptable salt thereof, to a patient with a Child-Pugh score of B or C.

In some embodiments, the present disclosure provides methods of treating a nalbuphine-treatable disorder in a hepatically impaired patient, comprising
  (a) determining the patient's Child-Pugh score;
  (b) administering a daily dose of about 15 mg to about 360 mg of nalbuphine, or a pharmaceutically acceptable salt thereof, to a patient with a Child-Pugh score of A;
  (c) administering a daily dose of about 4 mg to about 120 mg of nalbuphine, or a pharmaceutically acceptable salt thereof, to a patient with a Child-Pugh score of B; and
  (d) administering a daily dose of about 2 mg to about 45 mg C of nalbuphine, or a pharmaceutically acceptable salt thereof, to a patient with a Child-Pugh score of C.

In some embodiments, the nalbuphine-treatable disorder is selected from the group consisting of chronic cough, pruritus, prurigo nodularis, uremic pruritus, pruritus associated with liver disease, tardive dyskinesia, Huntington's disease and levodopa-induced dyskinesia (LID).

In some embodiments, the methods of treating a patient with a Child-Pugh score of A comprise administering a daily dose from about 14 mg to about 324 mg of an Equivalent Amount of Nalbuphine Free Base.

In some embodiments, the methods of treating a patient with a Child-Pugh score of B comprise administering a daily dose from about 6 mg to about 108 mg of an Equivalent Amount of Nalbuphine Free Base. In some embodiments, the methods of treating a patient with a Child-Pugh score of B comprise administering a daily dose of no more than about 108 mg of an Equivalent Amount of Nalbuphine Free Base. In some embodiments, the methods of treating a patient with a Child-Pugh score of B comprise administering a dose of about 27 mg, 54 mg, or about 108 mg of an Equivalent Amount of Nalbuphine Free Base. In some embodiments, a patient with a Child-Pugh score of B is administered about 27 mg of an Equivalent Amount of Nalbuphine Free Base once or twice daily. In some embodiments, a patient with a Child-Pugh score of B is administered about 54 mg of an Equivalent Amount of Nalbuphine Free Base once or twice daily.

In some embodiments, the methods of treating a patient with a Child-Pugh score of C comprise administering a daily dose from about 3 mg to about 108 mg of an Equivalent Amount of Nalbuphine Free Base.

In some embodiments, the methods of treating a patient with a Child-Pugh score of C comprise administering a daily dose from about 2 mg to about 108 mg (e.g., about 2 mg to about 54 mg) of an Equivalent Amount of Nalbuphine Free Base.

In some embodiments, the methods of treating a patient with a Child-Pugh score of C comprise administering a daily dose of no more than about 54 mg of an Equivalent Amount of Nalbuphine Free Base. In some embodiments, a patient with a Child-Pugh score of C is administered about 27 mg of an Equivalent Amount of Nalbuphine Free Base twice daily. In some embodiments, the daily dose administered to a patient with a Child-Pugh score of C is no more than about 27 mg of an Equivalent Amount of Nalbuphine Free Base. In some embodiments, a patient with a Child-Pugh score of C is administered about 27 mg of an Equivalent Amount of Nalbuphine Free Base administered once daily.

In some embodiments, the methods of treating a patient with a Child-Pugh score of C comprise administering a daily dose from about 2 mg to about 45 mg of nalbuphine or a pharmaceutically acceptable salt thereof.

In some embodiments, the methods described herein further include a step of titrating the dose of nalbuphine, or a pharmaceutically acceptable salt thereof, for at least about one week until a steady state is achieved in a patient with a Child-Pugh Score of A, B, or C. In some embodiments, the titration is conducted for about 2 weeks until a steady state is achieved in the patient. In some embodiments, the titration is conducted for about 7 days to about 30 days until a steady state is achieved in the patient. In some embodiments, the titration is conducted for about 12 days to about 20 days until a steady state is achieved in the patient.

In some embodiments, ascending doses of nalbuphine, or a pharmaceutically acceptable salt thereof, are administered to a patient with a Child-Pugh score of A during a titration until a steady state is achieved in the patient. In some embodiments, ascending doses of nalbuphine, or a pharmaceutically acceptable salt thereof, are administered during the titration until a tolerable and therapeutically effective dose of 30 mg, 60 mg, 90 mg, 120 mg, or 180 mg is achieved in the patient. In some embodiments, the titration is initiated with a dose of about 30 mg once or twice a day. In some embodiments, the titration comprises administering nalbuphine, or a pharmaceutically acceptable salt thereof in increments ranging from about 30 mg to about 60 mg. In some embodiments, titration twice a day is with an AM dosage and a PM dosage, wherein the PM dosage is higher than or the same as the AM dosage.

In some embodiments, ascending doses of nalbuphine, or a pharmaceutically acceptable salt thereof, are administered to a patient with a Child-Pugh score of B or C during titration until a steady state is achieved in the patient. In some embodiments, ascending doses of nalbuphine, or a pharmaceutically acceptable salt thereof, are administered during the titration until a tolerable and therapeutically effective dose of 10-15 mg, 20-31 mg, 18-45 mg, 41-54 mg, 40-60 mg or 60 mg is achieved in the patient. In some embodiments, the titration is initiated with a dose of about 1-10 mg once or twice a day, including from about 1 mg, 2 mg, about 3 mg, about 4 mg, about 5 mg, about 6 mg, about 7 mg, about 8 mg, about 9 mg, to about 10 mg once or twice a day, including all ranges and values therebetween. In some embodiments, the titration is initiated with a dose of about 10-15 mg once or twice a day, including from about 10 mg, about 11 mg, about 12 mg, about 13 mg, about 14 mg, to about 15 mg including all ranges and values therebetween. In some embodiments, the titration is initiated with a dose of about 27 mg of the Equivalent Amount of Nalbuphine Free Base. For example, In some embodiments, an initial dose of about 27 mg of the Equivalent Amount of Nalbuphine Free Base is administered to a patient with a Child-Pugh Score of B, and then titrated to a tolerable and therapeutically effective dose, for example about, 54 mg (as a single dose or an equally or unequally divided dose) or about 108 mg (as a single dose or an equally or unequally divided dose). In some embodiments, the total daily dose is no more than about 108 mg of the Equivalent Amount of Nalbuphine Free Base. In some embodiments, titration twice a day is with an AM dosage and a PM dosage, wherein the PM dosage is higher than or the same as the AM dosage.

In some embodiments, the present disclosure provides methods for treating a nalbuphine-treatable disorder in a patient with a Child-Pugh score of A, B or C. In some embodiments, the nalbuphine-treatable disorder is selected from the group consisting of chronic cough, pruritus, prurigo nodularis, uremic pruritus, tardive dyskinesia, Huntington's disease and levodopa-induced dyskinesia (LID). In some embodiments, the present disclosure provides methods of treating pruritus associated with liver disease in a patient with a Child-Pugh score of A, B or C. In some embodiments, the present disclosure provides methods of treating prurigo nodularis in a patient with a Child-Pugh score of A, B or C. In some embodiments, the present disclosure provides methods of treating uremic pruritus in a patient with a Child-Pugh score of A, B or C. In some embodiments, the present disclosure provides methods of treating idiopathic pulmonary fibrosis (IPF) cough, breathlessness or dyspnea in a patient with a Child-Pugh score of A, B or C. In some embodiments, the present disclosure provides methods of treating or mitigating levodopa-induced dyskinesia in a subject diagnosed with Parkinson's disease.

In some embodiments, the present disclosure provides methods of treating pruritus in hepatically impaired patients comprising:
  (a) determining the patient's Child-Pugh score;
  (b) administering a daily dose of about 15 mg to about 360 mg of nalbuphine, or a pharmaceutically acceptable salt thereof, to a patient with a Child-Pugh score of A In some embodiments, the present disclosure provides methods of treating pruritus in hepatically impaired patients comprising:
  (a) determining the patient's Child-Pugh score;
  (b) administering a daily dose of about 4 mg to about 120 mg of nalbuphine, or a pharmaceutically acceptable salt thereof, to a patient with a Child-Pugh score of B or C.

In some embodiments, the present disclosure provides methods of treating pruritus in hepatically impaired patients comprising:
  (a) determining the patient's Child-Pugh score;
  (b) administering a daily dose of about 4 mg to about 120 mg of nalbuphine, or a pharmaceutically acceptable salt thereof, to a patient with a Child-Pugh score of B.

In some embodiments, the present disclosure provides methods of treating pruritus in hepatically impaired patients comprising:
  (a) determining the patient's Child-Pugh score;
  (b) administering a daily dose of about 2 mg to about 45 mg of nalbuphine, or a pharmaceutically acceptable salt thereof to a patient with a Child-Pugh score of C.

In some embodiments, the present disclosure provides methods of safely administering nalbuphine, or a pharmaceutically acceptable salt there, in a hepatically impaired patient comprising:
  (a) determining the patient's Child-Pugh score;
  (b) administering a daily dose of about 15 mg to about 360 mg of nalbuphine, or a pharmaceutically acceptable salt thereof, to a patient with a Child-Pugh score of A; and
  (c) administering a daily dose of about 4 mg to about 120 mg of nalbuphine, or a pharmaceutically acceptable salt thereof, to a patient with a Child-Pugh score of B; and or C.

In some embodiments, the present disclosure provides methods of safely administering nalbuphine, or a pharmaceutically acceptable salt there, in a hepatically impaired patient comprising:
  (a) determining the patient's Child-Pugh score;
  (b) administering a daily dose of about 15 mg to about 360 mg of nalbuphine, or a pharmaceutically acceptable salt thereof, to a patient with a Child-Pugh score of A;
  (c) administering a daily dose of about 4 mg to about 120 mg of nalbuphine, or a pharmaceutically acceptable salt thereof, to a patient with a Child-Pugh score of B; and
  (d) administering a daily dose of about 2 mg to about 45 mg of nalbuphine, or a pharmaceutically acceptable salt thereof to a patient with a Child-Pugh score of C.

In some embodiments, the nalbuphine is in the form of an extended release oral dosage form.

In some embodiments, the nalbuphine is administered in a formulation comprising nalbuphine hydrochloride, mannitol, hydroxypropyl cellulose, locust bean gum, xanthan gum, calcium sulfate dihydrate, and magnesium stearate.

The present methods, and advantages thereof, are further illustrated by the following non-limiting detailed description, including the Examples.

DEFINITIONS

Figure 1:
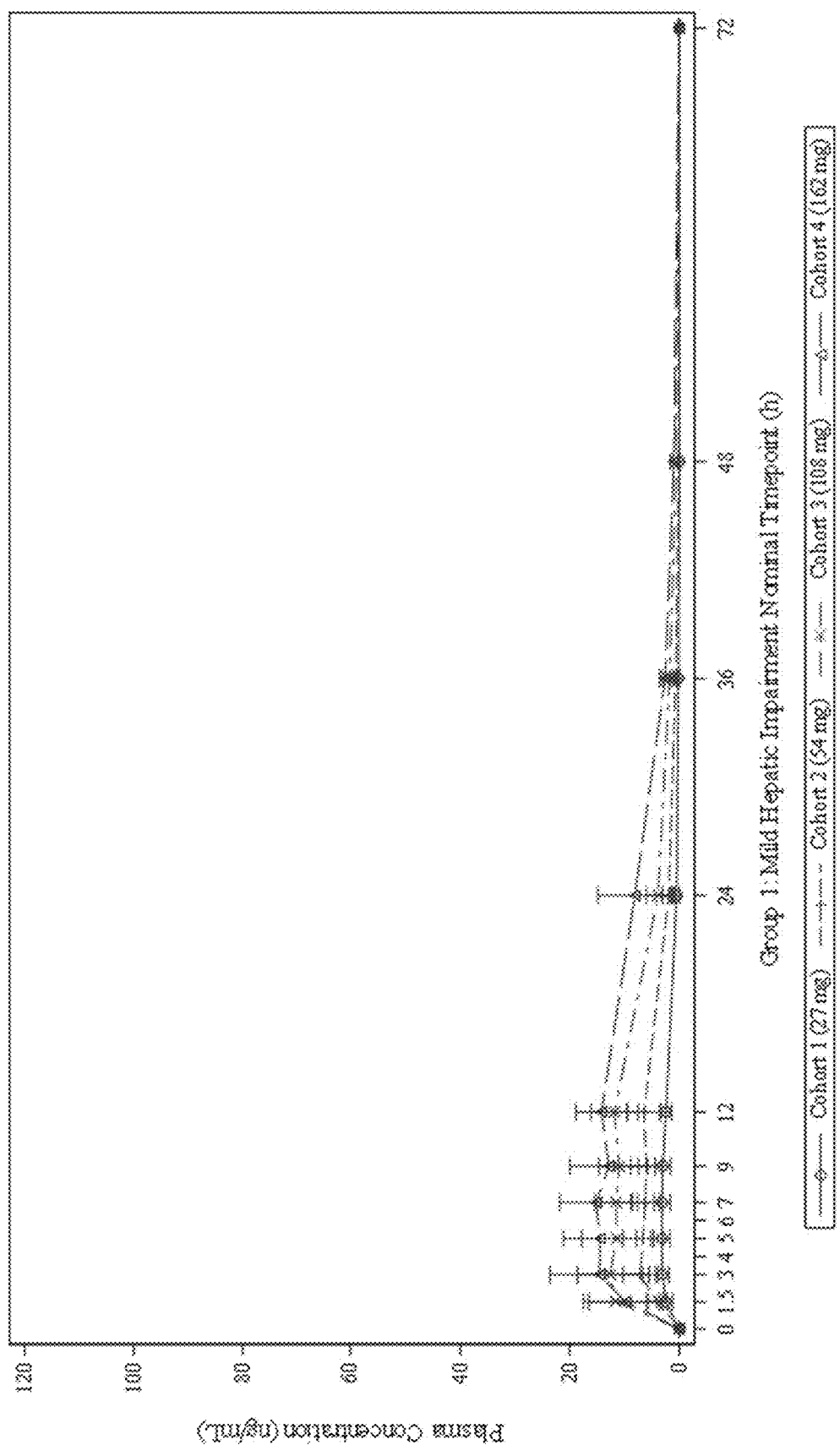
FIG. 1 shows the mean (±SD) plasma concentrations of nalbuphine in patients with mild hepatic impairment (Child Pugh A); in Cohorts 1-4 in Example 2) following single dose administration of 27 mg, 54 mg, 108 mg and 162 mg Nalbuphine extended release tablet.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The terms "administer," "administering" or "administration" as used herein refer to either directly administering a compound or pharmaceutically acceptable salt or ester of the compound or a composition comprising the compound or pharmaceutically acceptable salt or ester of the compound to a patient.

The term "adverse event" (AE) as used herein is defined as any untoward medical occurrence in a clinical investigation patient reported on or after the first screening date. An AE does not necessarily have to have a causal relationship with the treatment. An AE can therefore be any unfavorable and unintended sign (including an abnormal laboratory finding), symptom whether or not related to the medicinal (investigational) product, or disease temporally associated with the use of a medicinal (investigational) product. Typical adverse events include nausea, vomiting, somnolence, and dizziness. In accordance with the present disclosure, the rate of adverse events after the treatment is substantially the same as the rate of adverse events after administering a placebo for the same period of time.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound, or a salt, solvate or ester thereof, that, when administered to a patient, is capable of performing the intended result. For example, an effective amount of nalbuphine, or a pharmaceutically acceptable salt or ester thereof, is that amount which is required to reduce at least one symptom of pruritus in a patient, e.g. the amount required to reduce the itching sensation in a patient. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "salts" as used herein embraces pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid.

The term "treating" as used herein with regard to a patient, refers to improving at least one symptom of the patient's disorder. Treating can be improving, or at least partially ameliorating a disorder.

The term "therapeutic effect" as used herein refers to a desired or beneficial effect provided by the method and/or the composition. For example, the method for treating pruritus provides a therapeutic effect when the method reduces at least one symptom of pruritus, e.g., itching sensation, in a patient.

DETAILED DESCRIPTION

Nalbuphine is a synthetic opioid that acts as a competitive antagonist of the μ-opioid receptor while producing agonist effects at the κ-opioid receptor. Nalbuphine is currently available as a generic medication in an injectable form approved for use in the relief of moderate to severe pain, a supplement to balanced anesthesia, for pre-operative and post-operative analgesia and obstetrical analgesia during labor and delivery. Nalbuphine is hepatically cleared and extensively metabolized in the liver.

The development of portal systemic shunts by hepatic impairment leads to decreased hepatic blood flow and affect the rates of drug metabolism within the liver. These alterations in metabolic activities by hepatic impairment can significantly impact the efficacy and safety of highly metabolized drugs that may bypass first-pass metabolism because of these pathologies, leading, for example, to drug accumulation and alteration of drug absorption and disposition. Changes in pharmacokinetic parameters can lead to issues, including need for adjusting dose, complications for physicians in prescribing, lack of availability of correct doses, lack of availability of certain medications to those with hepatic impairment, and overdosing. Drugs with high extraction ratios (>0.7) are predicted to have altered pharmacokinetic (PK) properties (Gelot and Nakhla (2014); Delco et al (2005)). However, the extent of the alteration of PK cannot be predicted (Delco 2005; page 532). There is little information in the literature as it relates to dose ranging in hepatic impaired patients representing a significant gap in the medical literature given that the extent of PK alteration cannot be predicted. For example, Gelot and Nakhla (2014) report that most recommendations for opiate dosing guidelines in patients with hepatic impairment are based on case reports rather than sound clinical PK studies, and the use of immediate-release opioids rather than extended release (sustain release) formulations of opioids are recommended in hepatic impaired patients because the PK properties have not been formally studied. Thus, there are no clear guidelines in the literature to assist a physician in determining a safe and efficacious dose of a drug such as nalbuphine when treating hepatically impaired patients.

The present disclosure provides, among other things, methods of treating a patient with a Child-Pugh score of A, B, or C comprising administering an effective (e.g. therapeutically effective) amount of nalbuphine, or a pharmaceutically acceptable salt or ester thereof. In some embodiments, the methods of safely treating nalbuphine-treatable disorders comprise administering a therapeutically effective amount of nalbuphine, or a pharmaceutically acceptable salt or ester thereof, to a patient with a Child-Pugh score of A, B, or C.

According to the present disclosure, patients with varying hepatic impairment are classified by the Child Pugh system outlined in the Table below, which assigns a Child Pugh Score of A, B, or C to patients with mild, moderate, and severe hepatic impairment respectively.

| Parameter | 1 Point | 2 Points | 3 Points |
| --- | --- | --- | --- |
| Serum albumin (g/dL) | >3.5 | 2.8 to 3.5 | <2.8 |
| Total serum bilirubin (mg/dL) | <2.0 | 2.0 to 3.0 | >3.0 |
| Prolonged prothrombin time (sec) or prothrombin time INR (ratio) | <4<br><1.70 | 4 to 6<br>1.70 to 2.30 | >6<br>>2.30 |
| Ascites | Absent | Slight | Moderate or Subject on medication(s) to control ascites |
| Hepatic encephalopathy grade* | None | Grade 1 or 2 | Grade 3 or 4 or Subject receiving medication(s) to prevent encephalopathy |

*Grade 0: normal consciousness, personality, neurological examination, electroencephalogram
Grade 1: restless, sleep disturbed, irritable/agitated, tremor, impaired handwriting, 5 cps waves
Grade 2: lethargic, time-disoriented, inappropriate, asterixis, ataxia, slow triphasic waves
Grade 3: somnolent, stuporous, place-disoriented, hyperactive reflexes, rigidity, slower waves
Grade 4: unrousable coma, no personality/behavior, decerebrate, slow 2-3 cps delta activity
Assessment as good operative risk (A or mild) if 5 or 6 points; moderate risk (B or moderate) if 7 to 9 points; and poor operative risk (C or severe) if 10 to 15 points (developed for surgical evaluation of alcoholic cirrhotics).

In some embodiments, the present disclosure provides a method of safely administering nalbuphine, or a pharmaceutically acceptable salt thereof, in a hepatically impaired patient comprising:
  (a) determining the patient's Child-Pugh score;
  (b) administering a daily dose of about 15 mg to about 360 mg of nalbuphine, or a pharmaceutically acceptable salt thereof to a patient with a Child-Pugh score of A; and
  (c) administering a daily dose of about 4 mg to about 120 mg of nalbuphine, or a pharmaceutically acceptable salt thereof to a patient with a Child-Pugh score of B or C.

In some embodiments, the present disclosure provides a method of safely administering nalbuphine, or a pharmaceutically acceptable salt thereof, in a hepatically impaired patient comprising:
  (a) determining the patient's Child-Pugh score;
  (b) administering a daily dose of about 15 mg to about 360 mg of nalbuphine, or a pharmaceutically acceptable salt thereof to a patient with a Child-Pugh score of A;
  (c) administering a daily dose of about 4 mg to about 120 mg of nalbuphine, or a pharmaceutically acceptable salt thereof to a patient with a Child-Pugh score of B; and
  (d) administering a daily dose of about 2 mg to about 45 mg of nalbuphine, or a pharmaceutically acceptable salt thereof to a patient with a Child-Pugh score of C.

In some embodiments, the present disclosure provides methods of safely administering nalbuphine, or a pharmaceutically acceptable salt thereof, in a hepatically impaired patient comprising: administering a daily dose of about 15 mg to about 360 mg of nalbuphine, or a pharmaceutically acceptable salt thereof to a patient with a Child-Pugh score of A. In some embodiments, the present disclosure provides methods of safely administering nalbuphine, or a pharmaceutically acceptable salt thereof, in a hepatically impaired patient comprising: administering a daily dose of about 4 mg to about 120 mg of nalbuphine, or a pharmaceutically acceptable salt thereof to a patient with a Child-Pugh score of B. In some embodiments, the present disclosure provides methods of safely administering nalbuphine, or a pharmaceutically acceptable salt thereof, in a hepatically impaired patient comprising: administering a daily dose of about 4 mg to about 120 mg, or 4 mg to about 54 mg, or about 2 mg to about 45 mg of nalbuphine, or a pharmaceutically acceptable salt thereof to a patient with a Child-Pugh score of C.

In one aspect, the present disclosure provides method of treating a nalbuphine-treatable disorder in a hepatically impaired patient, comprising:

(a) determining the patient's Child-Pugh score;
(b) administering a daily dose of about 15 mg to about 360 mg of nalbuphine, or a pharmaceutically acceptable salt thereof, to a patient with a Child-Pugh score of A; and
(c) administering a daily dose of about 4 mg to about 120 mg of nalbuphine, or a pharmaceutically acceptable salt thereof, to a patient with a Child-Pugh score of B or C,
wherein the nalbuphine-treatable disorder is selected from the group consisting of chronic cough, pruritus, prurigo nodularis, uremic pruritus, tardive dyskinesia, Huntington's disease and levodopa-induced dyskinesia (LID).

In one aspect, the present disclosure provides method of treating a nalbuphine-treatable disorder in a hepatically impaired patient, comprising:
(a) determining the patient's Child-Pugh score;
(b) administering a daily dose of about 15 mg to about 360 mg of nalbuphine, or a pharmaceutically acceptable salt thereof, to a patient with a Child-Pugh score of A;
(c) administering a daily dose of about 4 mg to about 120 mg of nalbuphine, or a pharmaceutically acceptable salt thereof, to a patient with a Child-Pugh score of B; and
(d) administering a daily dose of about 2 mg to about 45 mg of nalbuphine, or a pharmaceutically acceptable salt thereof to a patient with a Child-Pugh score of C.
wherein the nalbuphine-treatable disorder is selected from the group consisting of chronic cough, pruritus, prurigo nodularis, uremic pruritus, tardive dyskinesia, Huntington's disease and levodopa-induced dyskinesia (LID).

In some embodiments of the methods described herein, the hepatically impaired patient has a Child-Pugh score of A. In some embodiments, the hepatically impaired patient has a Child-Pugh score of B. In some embodiments, the hepatically impaired patient has a Child-Pugh score of C.

In one aspect, provided herein is a method of treating pruritus in hepatically impaired patients comprising:
(a) determining the patient's Child-Pugh score;
(b) administering a daily dose of about 15 mg to about 360 mg of nalbuphine, or a pharmaceutically acceptable salt thereof, to a patient with a Child-Pugh score of A.

In some embodiments, provided herein is a method of treating pruritus in hepatically impaired patients comprising:
(a) determining the patient's Child-Pugh score;
(b) administering a daily dose of about 4 mg to about 120 mg of nalbuphine, or a pharmaceutically acceptable salt thereof, to a patient with a Child-Pugh score of B or C.

In some embodiments, provided herein is a method of treating pruritus in hepatically impaired patients comprising:
(a) determining the patient's Child-Pugh score;
(b) administering a daily dose of about 4 mg to about 120 mg of nalbuphine, or a pharmaceutically acceptable salt thereof, to a patient with a Child-Pugh score of B.

In some embodiments, provided herein is a method of treating pruritus in hepatically impaired patients comprising:
(a) determining the patient's Child-Pugh score;
(b) administering a daily dose of about 4 mg to about 120 mg of nalbuphine, or a pharmaceutically acceptable salt thereof, to a patient with a Child-Pugh score of C.

In some embodiments, provided herein is a method of treating pruritus in hepatically impaired patients comprising:
(a) determining the patient's Child-Pugh score;
(b) administering a daily dose of about 2 mg to about 45 mg of nalbuphine, or a pharmaceutically acceptable salt thereof, to a patient with a Child-Pugh score of C.

In another aspect, provided herein is a method of treating pruritus or idiopathic pulmonary fibrosis (IPF) cough, breathlessness or dyspnea in hepatically impaired patients comprising:
(a) determining the patient's Child-Pugh score;
(b) administering a daily dose of about 15 mg to about 360 mg of nalbuphine, or a pharmaceutically acceptable salt thereof, to a patient with a Child-Pugh score of A; and
(c) administering a daily dose of about 4 mg to about 120 mg of nalbuphine, or a pharmaceutically acceptable salt thereof, to a patient with a Child-Pugh score of B or C.

In another aspect, provided herein is a method of treating pruritus or idiopathic pulmonary fibrosis (IPF) cough, breathlessness or dyspnea in hepatically impaired patients comprising:
(a) determining the patient's Child-Pugh score;
(b) administering a daily dose of about 15 mg to about 360 mg of nalbuphine, or a pharmaceutically acceptable salt thereof, to a patient with a Child-Pugh score of A;
(c) administering a daily dose of about 4 mg to about 120 mg of nalbuphine, or a pharmaceutically acceptable salt thereof, to a patient with a Child-Pugh score of B; and
(d) administering a daily dose of about 2 mg to about 45 mg of nalbuphine, or a pharmaceutically acceptable salt thereof to a patient with a Child-Pugh score of C.

In some embodiments, provided herein is a method of treating pruritus or idiopathic pulmonary fibrosis (IPF) cough, breathlessness or dyspnea in hepatically impaired patients comprising: administering a daily dose of about 15 mg to about 360 mg of nalbuphine, or a pharmaceutically acceptable salt thereof, to a patient with a Child-Pugh score of A. In some embodiments, provided herein is a method of treating pruritus or idiopathic pulmonary fibrosis (IPF) cough, breathlessness or dyspnea in hepatically impaired patients comprising: administering a daily dose of about 4 mg to about 120 mg of nalbuphine, or a pharmaceutically acceptable salt thereof, to a patient with a Child-Pugh score of B or C. In some embodiments, provided herein is a method of treating pruritus or idiopathic pulmonary fibrosis (IPF) cough, breathlessness or dyspnea in hepatically impaired patients comprising: administering a daily dose of about 4 mg to about 120 mg of nalbuphine, or a pharmaceutically acceptable salt thereof, to a patient with a Child-Pugh score of B. In some embodiments, provided herein is a method of treating pruritus or idiopathic pulmonary fibrosis (IPF) cough, breathlessness or dyspnea in hepatically impaired patients comprising: administering a daily dose of about 4 mg to about 120 mg, or 4 mg to about 54 mg, or about 2 mg to about 45 mg of nalbuphine, or a pharmaceutically acceptable salt thereof, to a patient with a Child-Pugh score of C.

Throughout the present disclosure, the methods and doses used herein are generally expressed in terms of an amount of nalbuphine, or a pharmaceutically acceptable salt or ester thereof, for the "treatment of nalbuphine-treatable disorders" without specifying a particular nalbuphine-treatable disorder. For clarity, the present disclosure contemplates embodiments where methods and doses disclosed herein are effective for the treatment of any particular nalbuphine-treatable disorder, for example, chronic cough, pruritus, prurigo nodularis, uremic pruritus, pruritus associated with liver disease, tardive dyskinesia, Huntington's disease and levodopa-induced dyskinesia (LID). In some embodiments, the present disclosure provides methods of treating pruritus associated with liver disease in hepatically impaired patients. In some embodiments, the present disclosure provides methods of treating prurigo nodularis in hepatically impaired patients. In some embodiments, the present disclosure provides methods of treating uremic pruritus in hepatically impaired patients. In some embodiments, the present disclosure provides methods of treating cough, breathlessness or dyspnea in hepatically impaired patients. In some embodiments, the present disclosure provides methods of treating idiopathic pulmonary fibrosis (IPF) cough, breathlessness or dyspnea in hepatically impaired patients. In some embodiments, nalbuphine HCl is administered in the methods of the present disclosure. The present disclosure also contemplates the treatment of the nalbuphine-treatable disorders using the nalbuphine doses described in U.S. Pat. No. 8,637,538, and U.S. Patent Publication Nos. 2014/0179727; 2018/0008592; 2018/0125840; and 2020/0022974, which are incorporated by reference herein in their entirety.

In some embodiments, the pruritus is associated with liver disease. In some embodiments, the pruritus is associated with obstructive cholestasis secondary to bile duct obstruction due to non-hepatic tissue disease. In some embodiments, Nalbuphine is used or indicated for the treatment of pruritus associated with obstructive cholestasis secondary to bile duct obstruction due to non-hepatic tissue disease wherein the obstruction is caused by a condition selected from the group consisting of pancreatic cancer, pancreatitis, congenital or acquired biliary strictures, lymph node obstruction such as from lymphomas or bile duct stones.

In some embodiments, methods of the present disclosure are used for the treatment of pruritus associated with cholestatic liver disease in a patient with a Child Pugh score of A, B, or C. In some embodiments, the cholestatic liver disease is primary sclerosing cholangitis. In some embodiments, the cholestatic liver disease is primary biliary cholangitis.

In some embodiments, methods of the present disclosure are used for the treatment of pruritus associated with non-cholestatic liver disease in a patient with a Child Pugh score of A, B, or C.

In some embodiments, the methods of the present disclosure are used to treat pruritus associated with a liver disease selected from infectious hepatitis; cirrhotic liver disease, drug-induced liver disease, idiopathic portal hypertension, congenital malformations or genetic diseases affecting liver function, sarcoidosis, primary or metastatic neoplasm involvement of the liver and autoimmune hepatitis-cholangitis (Overlap syndrome) in a patient with a Child Pugh score of A, B, or C.

In some embodiments, the methods of the present disclosure are used to treat pruritus associated with infectious hepatitis in a patient with a Child Pugh score of A, B, or C. In some embodiments, the infectious hepatitis is selected from hepatitis C (HCV) and hepatitis B (HBV). In some embodiments, the HCV is selected from chronic HCV and HCV post-sustained virologic response. In some embodiments, the hepatitis B is selected from inactive HBV in a carrier and active HBV infection.

In some embodiments, the methods of the present disclosure are used to treat pruritus associated with cirrhotic liver disease in a patient with a Child Pugh score of A, B, or C. In some embodiments, the cirrhotic liver disease is selected from alcoholic liver disease, autoimmune hepatitis, and non-alcoholic fatty liver disease.

In some embodiments, the methods of the present disclosure are used to treat pruritus associated with a liver disease selected from drug-induced liver disease, idiopathic portal hypertension, congenital malformations or genetic diseases affecting liver function, sarcoidosis, primary or metastatic neoplasm involvement of the liver and autoimmune hepatitis-cholangitis (Overlap syndrome) in a patient with a Child Pugh score of A, B, or C.

In some embodiments, the methods of the present disclosure are used to treat pruritus associated with a liver disease in patients with hepatic impairment, wherein the patient's serum levels of endogenous opioids are elevated compared to normal serum levels. In some embodiments, the endogenous opioid is one or more endogenous μ-opioid receptor agonists. In some embodiments, the endogenous μ-opioid receptor agonist is selected from enkephalin and β-endorphin.

In some embodiments, the cough, breathlessness, or dyspnea associated with a particular condition such as IPF, refractory chronic cough, unexplained chronic cough, hypersensitivity pneumonitis, sarcoidosis, asbestosis, bronchiolitis obliterans, histiocytosis X, chronic eosinophilic pneumonia, collagen vascular disease, granulomatous vasculitis, Goodpasture's syndrome and, pulmonary alveolar proteinosis, COPD (such as COPD is associated with a condition such as emphysema, chronic bronchitis and Alpha-1-antitrypsin (AAt) deficiency or COPD associated with an irritant such as cigarette smoke, secondhand smoke, pipe smoke, air pollution and workplace exposure to dust, smoke or fumes) and other conditions described herein. In some embodiments, the chronic cough is selected from refractory chronic cough, unexplained chronic cough, unexplained and refractory chronic cough, idiopathic chronic cough, cough hypersensitivity syndrome, hypertussia, allotussia and neurogenic cough as well as suppression of the sensation of the urge to cough. In some embodiments, methods of the present disclosure are used for the treatment of cough, breathlessness, or dyspnea associated with IPF.

In accordance with some embodiments of the present disclosure, the method provides a therapeutic effect without producing a substantial adverse event. In some embodiments, the rate of adverse events after the treatment with nalbuphine is substantially the same as the rate of adverse events after administering a placebo for the same period of time. In some embodiments, the rate of liver-associated adverse events (such as elevated serum levels of liver function enzymes (i.e., serum alkaline phosphatase ("AP"), gamma-glutamyltranspeptidase ("GGT"), serum aminotransferases (alanine transaminase ("ALT") and/or aspartate transaminase ("AST")) after the treatment with nalbuphine is substantially the same as the rate of adverse events after administering a placebo for the same period of time.

In accordance with some embodiments of the present disclosure, the method of treating pruritus does not produce a substantial aquaretic effect.

In some embodiments of the present disclosure, the hepatically impaired patient treated for a nalbuphine-treatable disorder is a pediatric patient. In some embodiments of the present disclosure, the hepatically impaired patient treated a nalbuphine-treatable disorder is a geriatric patient.

Nalbuphine

Nalbuphine as employed in the present methods can form a part of a pharmaceutical composition by combining nalbuphine, or a pharmaceutically acceptable salt, solvate or ester thereof, with a pharmaceutically acceptable carrier. Additionally, the compositions can include an additive selected from the group consisting of adjuvants, excipients, diluents, release-modifying agents and stabilizers. The composition can be an immediate release formulation, a delayed release formulation, a sustained release formulation or an extended release formulation.

Nalbuphine HCl (17-(cyclobutylmethyl)-4,5α-epoxymorphinian-3, 6α, 14-triol, hydrochloride) is a synthetic opioid. Structurally, nalbuphine is a derivative of 14 hydroxymorphine.

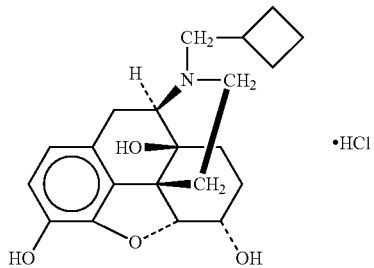

Nalbuphine HCl is currently available only as a generic medication in an injectable form. An injectable form of nalbuphine has been available as an approved drug formulation since 1978. Nubain® was the innovator brand injectable form of nalbuphine on which the presently sold generic bioequivalent injectable formulations are based. The injectable formulation is currently approved for use in the relief of moderate to severe pain, a supplement to balanced anesthesia, for pre-operative and post-operative analgesia and obstetrical analgesia during labor and delivery.

The present disclosure also includes pharmaceutically acceptable esters of nalbuphine. The term "ester" denotes a derivative of the agent containing an ester functional group (as described herein), which is capable of releasing the agent when the ester form is administered to a patient. Release of the active ingredient occurs in vivo. Pharmaceutically acceptable esters can be prepared by techniques known to one skilled in the art. These techniques generally modify appropriate functional groups in a given compound. These modified functional groups however regenerate original functional groups by metabolism of the compound in vivo. Esters include compounds wherein a hydroxy, carboxylic, or a similar group is modified.

Suitable pharmaceutically acceptable esters for a hydroxyl group include inorganic esters such as phosphate esters and α-acyloxyalkyl ethers and related compounds which, as a result of in vivo hydrolysis of the ester, provide the parent hydroxy group. In vivo hydrolyzable ester forming groups for hydroxy include alkanoyl (e.g., $C_{1-10}$ linear, branched or cyclic alkyl), benzoyl, phenylacetyl and substituted benzoyl and phenylacetyl, alkoxycarbonyl (to give alkyl carbonate esters), dialkylcarbamoyl and N—(N, N-dialkylaminoethyl)-N-alkylcarbamoyl (to give carbamates), N, N-dialkylaminoacetyl and carboxyacetyl.

In some embodiments, the nalbuphine used in the formulations and methods of the present disclosure is a pharmaceutically acceptable co-crystal of nalbuphine.

Formulations

The methods of the present disclosure can employ various formulations for administration to patients, e.g., humans and animals in unit dosage forms, such as tablets, capsules, pills, powders, granules, sterile parenteral solutions or suspensions, and oral solutions or suspensions, and oil-water emulsions containing suitable quantities of nalbuphine, or pharmaceutically acceptable salts or esters thereof.

Oral pharmaceutical dosage forms can be either solid or liquid. The solid dosage forms can be tablets, capsules, granules, and bulk powders. Types of oral tablets include compressed, chewable lozenges and tablets, which can be enteric-coated, sugar-coated or film-coated. Capsules can be hard or soft gelatin capsules, while granules and powders can be provided in non-effervescent or effervescent form with the combination of other ingredients known to those skilled in the art. In some embodiments, the oral dosage form may be an osmotic-controlled release oral delivery system (OROS). In some embodiments, the oral dosage form may include matrix-embedded dosage forms or related devices. In some embodiments, the present oral dosage forms may include orally-disintegrating tablets.

Pharmaceutically acceptable carriers utilized in tablets include binders, lubricants, diluents, disintegrating agents, coloring agents, flavoring agents, and wetting agents.

Liquid oral dosage forms include aqueous solutions, emulsions, suspensions, solutions and/or suspensions reconstituted from non-effervescent granules and effervescent preparations reconstituted from effervescent granules.

Aqueous solutions include, for example, elixirs and syrups. Elixirs are clear, sweetened, hydroalcoholic preparations. Pharmaceutically acceptable carriers used in elixirs include solvents. Syrups can be concentrated aqueous solutions of a sugar, for example, sucrose, and can contain a preservative. An emulsion is a two-phase system in which one liquid is dispersed in the form of small globules throughout another liquid. Emulsions can be either oil-in water or water-in-oil. Pharmaceutically acceptable carriers used in emulsions are non-aqueous liquids, emulsifying agents and preservatives. Suspensions can use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, can include organic acids and a source of carbon dioxide. Coloring and flavoring agents can be used in all of the above dosage forms.

Parenteral administration of the formulations of the present disclosure includes intravenous, subcutaneous and intramuscular administrations of immediate, sustained (e.g., depot), extended, and/or modified release formulations (e.g., as described herein). Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous. Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

The concentration of the pharmaceutically active compound can be adjusted so that an injection provides an effective amount to produce the desired pharmacological effect. The exact dose depends on the age, weight and condition of the patient or animal, as is known in the art. The unit-dose parenteral preparations are packaged in an ampoule or a syringe with a needle. All preparations for parenteral administration must be sterile, as is known and practiced in the art. Illustratively, intravenous or intra-arterial infusion of a sterile aqueous solution containing nalbuphine, or a pharmaceutically acceptable salt or ester thereof, is an effective mode of administration.

Pharmaceutical dosage forms for rectal administration can be rectal suppositories, capsules and tablets for systemic effect. Rectal suppositories as used herein mean solid bodies for insertion into the rectum which melt or soften at body temperature releasing the pharmacologically and/or therapeutically active ingredients contained in the composition of this disclosure. Pharmaceutically acceptable substances utilized in rectal suppositories are bases or vehicles and agents to raise the melting point. Examples of bases include cocoa butter (theobroma oil), glycerin-gelatin, carbowax, polyoxyethylene glycol and mixtures of mono-, di- and triglycerides of fatty acids. Combinations of the various bases can be used. Agents to raise the melting point of suppositories include spermaceti and wax. Rectal suppositories can be prepared either by the compressed method or by molding. The typical weight of a rectal suppository is about 2 to 3 gm. Tablets and capsules for rectal administration can be manufactured using the same pharmaceutically acceptable substance and by the same methods as for formulations for oral administration.

The compositions can be suspended in micronized or other suitable form or can be derivatized to produce a more soluble active product. The form of the resulting composition depends upon a number of factors, including the intended mode of administration and the solubility of the nalbuphine, or a pharmaceutically acceptable salt or ester thereof, in the selected carrier or vehicle. The effective concentration is sufficient for treating or alleviating pruritus, and can be empirically determined. The concentration is generally greater than the concentration for systemic administration of the compound.

The resulting mixture can be a solution, suspension, emulsion or the like, and can be formulated as a cream, gel, ointment, emulsion, solution, elixir, lotion, suspension, tincture, paste, foam, aerosol, irrigation, spray, suppository, bandage, or any other formulation suitable for topical administration. Modes of administration can include topical application to the skin, scalp, eyes, and/or nasal, buccal or sublingual mucosa.

Pharmaceutical and cosmetic carriers or vehicles suitable for administration of the compositions include any such carriers known to those skilled in the art to be suitable for the particular mode of administration. The nalbuphine, or a pharmaceutically acceptable salt or ester thereof, can be included in the carriers in amounts sufficient to exert a therapeutically useful effect without serious toxic effects on the treated individual.

To formulate these compositions, a weight fraction of nalbuphine, or a pharmaceutically acceptable salt or ester thereof, is dissolved, suspended, dispersed or otherwise mixed in a selected vehicle at an effective concentration such that the pruritic condition is relieved or ameliorated. Generally, emollient or lubricating vehicles that help hydrate the skin are more preferred than volatile vehicles, such as ethanol, that dry the skin. Examples of suitable bases or vehicles for preparing compositions for use with human skin are petrolatum, petrolatum plus volatile silicones, lanolin, cold cream (USP), and hydrophilic ointment (USP).

The compositions employed in the present methods can relieve pruritus when applied to the skin. Relief can be temporary or permanent, and can even be evident after a single dose of the composition. When the composition is administered in a form other than a topical preparation, it should be administered in an amount sufficient to provide relief from pruritus that is within safety guidelines established by the FDA. Determining the appropriate amount to administer to a patient is within the skill of the person of ordinary skill in the art in association with teachings provided by the present disclosure.

Solutions of the compositions of this disclosure intended for topical administration contain an amount of the composition effective to deliver a tolerable and therapeutically effective amount, typically at a concentration of between about 0.01% w/w to about 5% w/w. The balance of the solution is water, a suitable organic solvent or other suitable solvent or buffer. These compositions that are formulated as solutions or suspensions can be applied to the skin, or can be formulated as an aerosol or foam and applied to the skin as a spray-on. The aerosol compositions typically contain from 25% to 80% w/w, preferably from 30% to 50% w/w, of a suitable propellant. Gel compositions can be formulated by simply admixing a suitable thickening agent to the solution or suspension.

Compositions of solid forms intended for topical application can be formulated as stick-type compositions intended for application to the lips or other parts of the body. Such compositions contain an effective amount of nalbuphine, or a pharmaceutically acceptable salt, solvate or ester thereof. The amount of the nalbuphine, or a pharmaceutically acceptable salt or ester thereof, present is typically from about 0.01% w/w to about 5% w/w. The solids also contain from about 40% to 98% w/w, preferably from about 50% to 90% w/w, of emollients. This composition can further contain from 1% to 20% w/w, preferably from 5% to 15% w/w, of a suitable thickening agent, and, if desired or needed, emulsifiers and water or buffers.

Sustained Release

Nalbuphine formulations that can be employed in the present methods include oral sustained release nalbuphine formulations as described in U.S. Patent Publication Nos. 2019/0117576, 2019/0099416, 2015/0359789 2009/0030026, and 2007/0048376; and PCT Publication Nos. 2015/192071 and 2007/025005; each of which is incorporated herein by reference in their entireties.

"Sustained release" or "extended release" means that the nalbuphine, or pharmaceutically acceptable salt, solvate or ester thereof, is released from the formulation at a controlled rate so that therapeutically beneficial blood levels (but below toxic levels) of the nalbuphine, or pharmaceutically acceptable salt, solvate or ester thereof, are maintained over an extended period of time. Alternatively, "sustained release" or "extended release" means that the desired pharmacologic effect is maintained over an extended period of time.

The half-life of nalbuphine injectable formulations (i.e., IV or IM or SC) has been reported to be relatively short, only about 2-3 hours. In some embodiments, the present methods can employ oral sustained release formulations of nalbuphine including an effective amount of nalbuphine, or a pharmaceutically acceptable salt, solvate or ester thereof. The oral sustained release formulations can provide a controlled release and a lower $C_{max}$ of the nalbuphine, or a pharmaceutically acceptable salt thereof, over a longer period than observed for bolus injections or immediate release oral formulations (e.g., at least about 8-12 hours). Reducing the frequency of dosing provides the potential for enhanced patient convenience and compliance with the present methods. The lower dosing frequency also has the potential to provide reduced side effects because the patient may be exposed to lower peak concentrations of agent over time.

Without wishing to be bound by a particular theory, the longer than expected duration of therapeutic effect is attributed to the enterohepatic recirculation of nalbuphine. Nalbuphine forms a glucuronic acid or other type of conjugated metabolite in vivo through enzymatic reaction with an enzyme system such as UDP-glucuronyl transferase. It is also possible that enterohepatic recirculation also occurs when parent drug in the bile is released from the gallbladder into the intestine and reabsorbed. Once formed, the conjugated nalbuphine product is thought to be transported into the gastrointestinal tract via biliary secretion whereby the drug conjugate is cleaved liberating nalbuphine, which can be reabsorbed from the intestine. The sustained release formulation can improve the duration of therapeutic effect, by more slowly releasing nalbuphine into the in vivo system and allowing more drug to be conjugated and therefore available for recirculation and later reabsorption from the intestine.

The present methods can employ compositions including nalbuphine, or a pharmaceutically acceptable salt, solvate or ester thereof, nalbuphine, or a pharmaceutically acceptable salt thereof, and a sustained release delivery system. The sustained release delivery system includes (i) at least one hydrophilic compound, at least one cross-linking agent, and at least one pharmaceutical diluent; (ii) at least one hydrophilic compound, at least one cross-linking agent, at least one pharmaceutical diluent, and at least one cationic cross-linking agent different from the first cross-linking agent; or (iii) at least one hydrophilic compound, at least one cationic cross-linking compound, and at least one pharmaceutical diluent. Alternatively, in some embodiments, the present methods can employ compositions including nalbuphine, or a pharmaceutically acceptable salt, solvate or ester thereof, and a sustained release delivery system, which may employ a hydrophobic compound in a sustained release system.

The nalbuphine can be homogeneously dispersed in the sustained release delivery system.

In some embodiments, the nalbuphine, or pharmaceutically acceptable salt, solvate or ester thereof, is present in the composition in an amount of about 1 mg to 360 mg, including in an amount of from about 1 mg, about 2 mg, about 3 mg, about 4 mg, about 5 mg, about 6 mg, about 7 mg, bout 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 60 mg, about 65 mg, about 70 mg, about 75 mg, about 80 mg, about 85 mg, about 90 mg, about 95 mg, about 100 mg, about 105 mg, about 108 mg, about 110 mg, about 120 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 200 mg, about 210 mg, about 220 mg, about 230 mg, about 240 mg, about 250 mg, about 360 mg, about 260 mg, about 280 mg, about 290 mg, about 300 mg, about 310 mg, about 320 mg, about 330 mg, about 340 mg, about 350 mg, to about 360 mg, including all ranges therebetween. In some embodiments, the nalbuphine, or a pharmaceutically acceptable salt thereof, is present in the composition in an amount of about 1 mg to about 240 mg; about 1 mg to about 150 mg; about 1 mg to about 125 mg; or about 1 mg to about 100 mg. In some embodiments, nalbuphine, or pharmaceutically acceptable salt, solvate or ester thereof, is present in the composition in an amount of about 1 mg to about 50 mg, about 5 mg to about 80 mg; about 10 mg to about 70 mg; about 15 mg to about 60 mg; about 40 mg to about 80 mg; about 50 mg to about 70 mg; or about 45 mg to about 60 mg. In some embodiments, the nalbuphine, or pharmaceutically acceptable salt, solvate or ester thereof, is present in the composition in an amount of about 1 mg, about 2 mg, about 3 mg, about 4 mg, about 5 mg, about 6 mg, about 7 mg, bout 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 60 mg, about 65 mg, about 70 mg, about 75 mg, about 80 mg, about 85 mg, about 90 mg, about 95 mg, about 100 mg, about 108 mg, about 110 mg, about 120 mg, about 130 mg, about 140 mg, about 150 mg, about 160 mg, about 170 mg, about 180 mg, about 190 mg, or about 240 mg including all values therebetween. In some embodiments, the nalbuphine, or pharmaceutically acceptable salt thereof, is present in the composition in an amount of about 15 mg, about 30 mg, about 45 mg, about 60 mg, about 90 mg, about 120 mg, or about 180 mg.

In some embodiments, the pharmaceutically acceptable salt of nalbuphine, e.g., nalbuphine HCl, is present in the composition in an amount of about 15 mg, about 30 mg, about 60 mg, about 90 mg, about 120 mg, or about 180 mg, or about 360 mg. For compositions comprising a pharmaceutically acceptable salt of nalbuphine, the amount of nalbuphine in said compositions may be expressed as the Equivalent Amount of Nalbuphine Free Base, which is the calculated amount of nalbuphine free base in the composition based on the actual amount of the pharmaceutically acceptable salt of nalbuphine in the composition. The amount of the Equivalent Amount of Nalbuphine Free Base in a composition will vary within the manufacturing process, and the compositions of the present disclosure encompass pharmaceutically-acceptable deviations (i.e., FDA-acceptable) from the nalbuphine content that is recited in the present disclosure.

The following table shows the Equivalent Amount of Nalbuphine Free Base for compositions containing 15 mg, 30 mg, 60 mg, 90 mg, 120 mg, 180 mg and 240 mg of nalbuphine HCl:

| Amount of nalbuphine HCl | Equivalent Amount of Nalbuphine Free Base |
| --- | --- |
| 15 mg | 13.6[1] |
| 30 mg | 27.2 |
| 60 mg | 54.4 |
| 90 mg | 81.6 |
| 120 mg | 108.8 |
| 180 mg | 163.2 |
| 240 mg | 217.6 |

[1]The amount of Equivalent Amount of Nalbuphine Free Base is rounded to the nearest 0.1 decimal place using the equation below.

Throughout the present disclosure, the amount of nalbuphine in a composition is generally expressed in terms of the amount of nalbuphine hydrochloride present in a composition. However, the present disclosure contemplates embodiments where the nalbuphine is present in another nalbuphine form (such as a different pharmaceutically acceptable salt and/or ester) and provides about the same Equivalent Amount of Nalbuphine Free Base as the embodiments that are expressly described herein. For example, about 251 mg of nalbuphine citrate (FW=549.57 g/mol) provides about the same Equivalent Amount of Nalbuphine Free Base as about 180 mg of nalbuphine hydrochloride. The Equivalent Amount of Nalbuphine Free Base in said compositions may be calculated by the following formula:

Equivalent Amount of Nalbuphine Free Base=

$$\frac{\text{Mass of Pharmaceutically Acceptable Salt (g)} \times 357.45 \left(\text{Formula Weight of Nalbuphine Free Base}, \frac{g}{mol}\right)}{\text{Formula Weight of Pharmaceutically Acceptable Salt} \left(\frac{g}{mol}\right)}$$

The Equivalent Amount of Nalbuphine Free Base content of the dosage form calculated using the equation above may be adjusted by a pharmaceutically acceptable amount (for example, within an amount permitted by FDA safety standards, which in some embodiments is 1% or less of the calculated Equivalent Amount of Nalbuphine Free Base) to allow product labeling using a whole number integer when referencing the dosage strength. For example, the calculated Equivalent Amount of Nalbuphine Free Base for 240 mg of nalbuphine hydrochloride is 217.6 mg. According to the present disclosure, the nalbuphine content of the composition may be adjusted for a product labelling of 216 mg of Equivalent Amount of Nalbuphine Free Base.

In some embodiments, the sustained release delivery system is present in the composition in an amount from about 10 mg to about 420 mg; from about 15 mg to about 360 mg, from about 7 mg to about 108 mg; from about 25 mg to about 225 mg; from about 21 mg to about 198 mg; from about 80 mg to about 200 mg; from about 80 mg to about 220 mg; from about 90 mg to about 210 mg; from about 100 mg to about 200 mg; from about 110 mg to about 190 mg; from about 120 mg to about 180 mg; from about 130 mg to about 170 mg; from about 140 mg to about 160 mg; from about 30 mg to about 60 mg; from about 60 mg to about 180 mg; from about 30 mg to about 180 mg; from about 75 mg to about 150 mg; from about 80 mg to about 160 mg; from about 90 mg to about 150 mg; from about 100 mg to about 140 mg; from about 110 mg to about 130 mg, from about 100 mg to about 300 mg; from about 200 mg to about 300 mg or from about 200 mg to about 250 mg. In some embodiments, the sustained release delivery system is present in the composition in an amount from about 75 mg to about 150 mg.

In some embodiments, the sustained release delivery system is present in the composition in an amount of about 7 mg, about 9 mg, about 11 mg, about 13 mg, about 15 mg, about 20 mg, about 30 mg, about 31 mg, about 60 mg, about 75 mg, about 80 mg, about 90 mg, about 100 mg, about 108 mg, about 110 mg, about 112 mg, about 115 mg, about 117 mg, about 120 mg, about 125 mg, about 130 mg, about 135 mg, about 140 mg, about 145 mg, about 150 mg, about 160 mg, about 170 mg, about 180 mg, about 190 mg, about 200 mg, about 210 mg, about 220 mg, about 225 mg, about 230 mg, about 240 mg, about 250 mg, about 260 mg, about 270 mg, about 280 mg, about 300 mg, about 320 mg, about 340 mg, about 360 mg, about 380 mg, about 400 mg or about 420 mg. In some embodiments, the sustained release delivery system is present in the composition in an amount of about 112 mg.

The ratio of nalbuphine, or pharmaceutically acceptable salt, solvate or ester thereof, in the compositions to the sustained release delivery system is generally from about 4:1 to about 1:25. In some embodiments, the ratio of nalbuphine, or pharmaceutically acceptable salt, solvate or ester thereof, to the sustained release delivery system is generally from about 2.5:1 to about 1:4. In some embodiments, the ratio of nalbuphine, or pharmaceutically acceptable salt, solvate or ester thereof, to the sustained release delivery system is generally from about 5:1 to about 1:5, about 4:1 to about 1:4, about 3:1 to about 1:3, about 2:1 to about 1:2, about 1:1 to about 1:5, about 1:1 to about 1:4, about 1:1 to about 1:3, about 1:1 to about 1.2, and about 1:2 to about 1:3. In some embodiments, the ratio of nalbuphine, or pharmaceutically acceptable salt, solvate or ester thereof, to the sustained release delivery system is about 1:1, about 1:2, about 1:2.5, about 1:3, about 1:4, or about 1:5.

In some embodiments, at least one hydrophilic compound is present in the sustained release delivery system in an amount of about 5% to about 80% by weight; the at least one cross-linking agent is present in the sustained release delivery system in an amount of about 0.5% to about 80% by weight; and the at least one pharmaceutical diluent is present in the sustained release delivery system in an amount of about 20% to about 80% by weight. In some embodiments, the at least one hydrophilic compound is present in the sustained release delivery system in an amount of about 8% to about 31% by weight; the at least one cross-linking agent is present in the sustained release delivery system in an amount of about 12% to about 47% by weight; and the at least one pharmaceutical diluent is present in the sustained release delivery system in an amount of about 20% to about 78% by weight. In some embodiments, the at least one hydrophilic compound is present in the sustained release delivery system in an amount of about 10% to about 20% by weight; the at least one cross-linking agent is present in the sustained release delivery system in an amount of about 15% to about 25% by weight; and the at least one pharmaceutical diluent is present in the sustained release delivery system in an amount of about 50% to about 85% by weight. In some embodiments, the at least one hydrophilic compound is present in the sustained release delivery system in an amount of about 8%, about 9%, about 10%, about 11%, about 12%, about 13%, about 14%, about 15%, about 16%, about 17%, about 18%, about 19%, about 20%, about 22%, about 24%, about 26%, about 28%, about 30%, about 32%, about 34%, or about 36% by weight; the at least one cross-linking agent is present in the sustained release delivery system in an amount of about 10%, about 11%, about 12%, about 13%, about 14%, about 15%, about 16%, about 17%, about 18%, about 19%, about 20%, about 22%, about 24%, about 26%, about 28%, about 30%, about 32%, about 33%, about 34%, or about 35% by weight; and the at least one pharmaceutical diluent is present in the sustained release delivery system in an amount of about 40%, about 45%, about 50%, about 55%, about 60%, about 65%, about 70%, about 80%, or about 85% by weight.

In some embodiments, the at least one hydrophilic compound is present in the sustained release delivery system in an amount of about 10%, about 11%, about 12%, about 13%, about 14%, about 15%, about 16%, about 17%, about 18%, about 19%, or about 20% by weight; the at least one cross-linking agent is present in the sustained release delivery system in an amount of about 15%, about 16%, about 17%, about 18%, about 19%, about 20%, or about 22% by weight; and the at least one pharmaceutical diluent is present in the sustained release delivery system in an amount of about 55%, about 60%, about 65%, about 70%, about 80%, or about 85% by weight. In some embodiments, the at least one hydrophilic compound is present in the sustained release delivery system in an amount of about 8%, about 12%, or about 20% by weight; the at least one cross-linking agent is present in the sustained release delivery system in an amount of about 12%, about 18%, or about 30% by weight; and the at least one pharmaceutical diluent is present in the sustained release delivery system in an amount of about 40%, about 60%, or about 70% by weight.

In some embodiments, nalbuphine is in the form of any pharmaceutically acceptable salt known in the art. Exemplary pharmaceutically acceptable salts include without limitation hydrochloric, sulfuric, nitric, phosphoric, hydrobromic, maleic, malic, ascorbic, citric, tartaric, pamoic, lauric, stearic, palmitic, oleic, myristic, lauryl sulfuric, napthalenesulfonic, linoleic, linolenic acid, and the like. Some embodiments includes the hydrochloride salt of nalbuphine.

The sustained release delivery system includes at least one hydrophilic compound. The hydrophilic compound preferably forms a gel matrix that releases the nalbuphine, or the pharmaceutically acceptable salt, solvate or ester thereof, at a sustained rate upon exposure to liquids. The rate of release of the nalbuphine, or the pharmaceutically acceptable salt, solvate or ester thereof, from the gel matrix depends on the drug's partition coefficient between the components of the gel matrix and the aqueous phase within the gastrointestinal tract. The weight ratio of nalbuphine to hydrophilic compound is generally in the range of about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, and about 2:1 to about 1:2. In some embodiments, the weight ratio of nalbuphine to hydrophilic compound is in the range of about 10:1 to about 1:1, about 10:1 to about 2:1, about 9:1 to about 1:1, about 8:1 to about 1:1, about 7:1 to about 1:1, about 6:1 to about 1:1, about 5:1 to about 1:1, about 4:1 to about 1:1, about 3:1 to about 1:1, and about 2:1 to about 1:1. In some embodiments, the weight ratio of nalbuphine to hydrophilic compound is in the range of about 6:1 to about 1:1, about 5:1 to about 2:1, about 4:1 to about 3:1, about 4:1 to about 2:1, and about 5:1 to about 2:1. In some embodiments, the weight ratio of nalbuphine to hydrophilic compound is about 1:5, about 1:4.5, about 1:4.4, about 1:4, about 1:3.5, about 1:3.3, about 1:3, about 1:2.5, about 1:2, about 1:1, and about 1:1.5.

The sustained release delivery system generally includes the hydrophilic compound in an amount of about 5% to about 80% by weight. In some embodiments, the sustained release delivery system generally includes the hydrophilic compound in an amount of about 5% to about 30%, about 8% to about 31%, about 10% to about 20%, about 20% to about 60%, or about 40% to about 60% by weight. In some embodiments, the sustained release delivery system includes the hydrophilic compound in an amount of about 8% to about 31% by weight. In some embodiments, the sustained release delivery system includes the hydrophilic compound in an amount of about 10% to about 20% by weight. In some embodiments, the sustained release delivery system includes the hydrophilic compound in an amount of about 10%, about 11%, about 12%, about 13%, about 14%, about 15%, about 16%, about 17%, about 18%, about 19%, or about 20% by weight. In some embodiments, the sustained release delivery system includes the hydrophilic compound in an amount of about 12% by weight. In some embodiments, the sustained release delivery system includes the hydrophilic compound in an amount of about 8% by weight. In some embodiments, the sustained release delivery system includes the hydrophilic compound in an amount of about 20% by weight. In some embodiments, the sustained release delivery system includes the hydrophilic compound in an amount of about 28% by weight.

The hydrophilic compound is any pharmaceutically acceptable compound known in the art to be hydrophilic. Exemplary hydrophilic compounds include without limitation pharmaceutically acceptable gums, cellulose ethers, polyvinyl pyrrolidone, protein-derived compounds, and mixtures thereof. Exemplary gums include without limitation heteropolysaccharide gums and homopolysaccharide gums, such as xanthan, tragacanth, pectins, acacia, karaya, alginates, agar, guar, hydroxypropyl guar, carrageenan, locust bean gums, and gellan gums. Exemplary cellulose ethers include without limitation hydroxyalkyl celluloses and carboxyalkyl celluloses. In some embodiments, cellulose ethers include hydroxyethyl celluloses, hydroxypropyl celluloses, hydroxypropylmethyl-celluloses, carboxy methylcelluloses, and mixtures thereof. In some embodiments, the hydrophilic compound is a gum. In some embodiments, the hydrophilic compound is a heteropolysaccharide gum. In further embodiments, the hydrophilic compound is a xanthan gum or derivative thereof. Derivatives of xanthan gum include without limitation, for example, deacylated xanthan gum, the carboxymethyl esters of xanthan gum, and the propylene glycol esters of xanthan gum.

In another aspect, the sustained release delivery system further includes at least one cross-linking agent. In some embodiments, the cross-linking agent is a compound that is capable of cross-linking the hydrophilic compound to form a gel matrix in the presence of liquids. As used herein, "liquids" includes, for example, gastrointestinal fluids and aqueous solutions, such as those used for in vitro dissolution testing. The sustained release delivery system generally includes the cross-linking agent in an amount of about 0.5% to about 80% by weight. In some embodiments, the sustained release delivery system generally includes the cross-linking agent in an amount of about 12% to about 47% by weight. In some embodiments, the sustained release delivery system generally includes the cross-linking agent in an amount of about 20% to about 30% by weight. In some embodiments, the sustained release delivery system generally includes the cross-linking agent in an amount of about 15% to about 25% by weight. In some embodiments, the at least one cross-linking agent is present in the sustained release delivery system in an amount of about 15%, about 16%, about 17%, about 18%, about 19%, about 20%, about 21%, about 22%, about 23%, about 24%, or about 25% by weight. In some embodiments, the sustained release delivery system includes the cross-linking agent in an amount of about 18% by weight. In some embodiments, the sustained release delivery system includes the cross-linking agent in an amount of about 12% by weight. In some embodiments, the sustained release delivery system includes the cross-linking agent in an amount of about 30% by weight. In some embodiments, the sustained release delivery system includes the cross-linking agent in an amount of about 42% by weight.

Exemplary cross-linking agents include homopolysaccharides. Exemplary homopolysaccharides include without limitation galactomannan gums, such as guar gum, hydroxypropyl guar gum, and locust bean gum. In some embodiments, the cross-linking agent is a locust bean gum or a guar gum. In some embodiments, the cross-linking agent is an alginic acid derivative or hydrocolloid.

In some embodiments, when the sustained release delivery system includes at least one hydrophilic compound and at least one cross-linking agent, the weight ratio of hydrophilic compound to cross-linking agent is from about 1:9 to about 9:1, about 1:8 to about 8:1, about 1:7 to about 7:1, about 1:6 to about 6:1, about 1:5 to about 5:1, about 1:4 to about 4:1, about 1:3 to about 3:1, or about 1:2 to about 2:1. In some embodiments, the weight ratio of hydrophilic compound to cross-linking agent is about 1:5, about 1:4.5, about 1:4, about 1:3.5, about 1:3, about 1:2.5, about 1:2, about 1:1.5, and about 1:1.

When the sustained release delivery system includes at least one hydrophilic compound and at least one cross-linking agent, the weight ratio of the nalbuphine, or pharmaceutically acceptable salt, solvate or ester thereof, to the sum of the at least one hydrophilic compound and the at least one cross-linking agent is from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3, or from about 2:1 to about 1:2. In some embodiments, the weight ratio of the nalbuphine, or pharmaceutically acceptable salt, solvate or ester thereof, to the sum of the at least one hydrophilic compound and the at least one cross-linking agent is from about 4:1 to about 1:1, from about 4:1 to about 1:1.5, from about 3:1 to about 1:1, or from about 2:1 to about 1:1. In some embodiments, the ratio of the nalbuphine, or pharmaceutically acceptable salt, solvate or ester thereof, to the sum of the at least one hydrophilic compound and the at least one cross-linking agent is about 5:1, about 4:1 (i.e., 1:0.25), about 3.5:1, about 3:1, about 2.5:1, about 2:1 (i.e., 1:0.5), about 1.9:1, about 1.8:1, about 1.7:1, about 1.6:1, about 1.5:1, about 1.4:1, about 1.3:1, about 1.2:1, about 1.1:1, about 1:1, about 1:1.5, about 1:2, about 1:3, about 1:4, and about 1:5.

The sustained release delivery system further includes one or more pharmaceutical diluents known in the art. Exemplary pharmaceutical diluents include without limitation monosaccharides, disaccharides, polyhydric alcohols and mixtures thereof. In some embodiments, pharmaceutical diluents include, for example, starch, mannitol, lactose, dextrose, sucrose, microcrystalline cellulose, sorbitol, xylitol, fructose, and mixtures thereof. In some embodiments, the pharmaceutical diluent is water-soluble. Non limiting examples of water-soluble pharmaceutical diluents include lactose, dextrose, sucrose, or mixtures thereof. The weight ratio of pharmaceutical diluent to hydrophilic compound is generally from about 1:9 to about 9:1, from about 1:8 to about 8:1, from about 1:7 to about 7:1, from about 1:6 to about 6:1, from about 1:5 to about 5:1, from about 1:4 to about 4:1, from about 1:3 to about 3:1, or from about 1:2 to about 2:1. In some embodiments, the weight ratio of pharmaceutical diluent to hydrophilic compound is generally from about 9:1 to about 1:1.5. In some embodiments, the weight ratio of pharmaceutical diluent to hydrophilic compound is about 9:1, about 8.75:1, about 8.5:1, about 8.25:1, about 8:1, about 7.5:1, about 7:1, about 6.5:1, about 6:1, about 5.5:1, about 5:1, about 4.5:1, about 4:1, about 3.5:1, about 3:1, about 2.5:1, about 2:1, about 1.5:1, or about 1:1.

The sustained release delivery system generally includes one or more pharmaceutical diluents in an amount of about 20% to about 80%, about 30% to about 70%, about 40% to about 70%, or about 40% to about 60%. In some embodiments, the sustained release delivery system includes one or more pharmaceutical diluents in an amount of about 20% to about 70% by weight. In some embodiments, the sustained release delivery system includes one or more pharmaceutical diluents in an amount of about 50% to about 85% by weight. In some embodiments, the sustained release delivery system includes one or more pharmaceutical diluents in an amount of about 55%, about 60%, about 65%, about 70%, about 80%, or about 85% by weight. In some embodiments, the sustained release delivery system includes one or more pharmaceutical diluents in an amount of about 20% by weight. In some embodiments, the sustained release delivery system includes one or more pharmaceutical diluents in an amount of about 30% by weight. In some embodiments, the sustained release delivery system includes one or more pharmaceutical diluents in an amount of about 40% by weight. In some embodiments, the sustained release delivery system includes one or more pharmaceutical diluents in an amount of about 50% by weight. In some embodiments, the sustained release delivery system includes one or more pharmaceutical diluents in an amount of about 60% by weight. In some embodiments, the sustained release delivery system includes one or more pharmaceutical diluents in an amount of about 70% by weight.

In a further aspect, the sustained release delivery system includes one or more cationic cross-linking compounds. In some embodiments, the one or more cationic cross-linking compounds are used instead of the cross-linking agent. In some embodiments, the one or more cationic cross-linking compounds are used in addition to the cross-linking agent. In some embodiments, the one or more cationic cross-linking compounds are used in an amount sufficient to cross-link the hydrophilic compound to form a gel matrix in the presence of liquids. In some embodiments, the one or more cationic cross-linking compounds are present in the sustained release delivery system in an amount of about 0.5% to about 30%, about 0.5% to about 25%, about 0.5% to about 20%, about 0.5% to about 15%, about 0.5% to about 10%, or about 0.5% to about 5% by weight. In some embodiments, the one or more cationic cross-linking compounds are present in the sustained release delivery system in an amount of about 5% to about 20%, about 5% to about 15%, about 6% to about 14%, about 7% to about 13%, about 8% to about 12%, or about 9% to about 11% by weight. In some embodiments, the one or more cationic cross-linking compounds are present in the sustained release delivery system in an amount of about 5%, about 6%, about 7%, about 8%, about 9%, about 10%, about 11%, about 12%, about 13%, about 14%, or about 15% by weight. In some embodiments, the cationic cross-linking compound is present in the sustained release delivery system in an amount of about 10% by weight.

Exemplary cationic cross-linking compounds include without limitation monovalent metal cations, multivalent metal cations, and inorganic salts, including alkali metal and/or alkaline earth metal sulfates, chlorides, borates, bromides, citrates, acetates, lactates, and mixtures thereof. For example, the cationic cross-linking compound include without limitation one or more of calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, sodium fluoride, or mixtures thereof.

When the sustained release delivery system includes at least one hydrophilic compound and at least one cationic cross-linking compound, the weight ratio of hydrophilic compound to cationic cross-linking compound ranges from about 1:9 to about 9:1, from about 1:8 to about 8:1, from about 1:7 to about 7:1, from about 1:6 to about 6:1, from about 1:5 to about 5:1, from about 1:4 to about 4:1, from about 1:3 to about 3:1, or from about 1:2 to about 2:1. In some embodiments, the weight ratio of hydrophilic compound to cationic cross-linking compound ranges from about 1:3 to about 3:1. In some embodiments, the weight ratio of hydrophilic compound to cationic cross-linking compound is about 3:1, about 2.75:1, about 2.5:1, about 2.25:1, about 2:1, about 1.8:1, about 1.6:1, about 1.4:1, about 1.2:1, about 1:1, about 1:1.25, about 1:1.5, or about 1:2. In some embodiments, the weight ratio of hydrophilic compound to cationic cross-linking compound is about 1:1.25. In some embodiments, the weight ratio of hydrophilic compound to cationic cross-linking compound is about 1.2:1. In some embodiments, the weight ratio of hydrophilic compound to cationic cross-linking compound is about 2:1. In some embodiments, the weight ratio of hydrophilic compound to cationic cross-linking compound is about 2.8:1.

In some embodiments, the at least one hydrophilic compound is present in the sustained release delivery system in an amount of about 5% to about 80% by weight; the at least one cationic cross-linking agent is present in the sustained release delivery system in an amount of about 0.5% to about 30% by weight; and the at least one pharmaceutical diluent is present in the sustained release delivery system in an amount of about 20% to about 80% by weight. In some embodiments, the at least one hydrophilic compound is present in the sustained release delivery system in an amount of about 8% to about 30% by weight; the at least one cationic cross-linking agent is present in the sustained release delivery system in an amount of about 10% by weight; and the at least one pharmaceutical diluent is present in the sustained release delivery system in an amount of about 20% to about 70% by weight. In some embodiments, the at least one hydrophilic compound is present in the sustained release delivery system in an amount of about 5% to about 30% by weight; the at least one cationic cross-linking agent is present in the sustained release delivery system in an amount of about 5% to about 20% by weight; and the at least one pharmaceutical diluent is present in the sustained release delivery system in an amount of about 20% to about 85% by weight. In some embodiments, the at least one hydrophilic compound is present in the sustained release delivery system in an amount of about 10% to about 20% by weight; the at least one cationic cross-linking agent is present in the sustained release delivery system in an amount of about 5% to about 15% by weight; and the at least one pharmaceutical diluent is present in the sustained release delivery system in an amount of about 50% to about 85% by weight.

In some embodiments, the at least one hydrophilic compound is present in the sustained release delivery system in an amount of about 8%, about 9%, about 10%, about 11%, about 12%, about 13%, about 14%, about 15%, about 16%, about 17%, about 18%, about 19%, about 20%, about 22%, about 24%, about 26%, about 28%, or about 30% by weight; the at least one cationic cross-linking agent is present in the sustained release delivery system in an amount of about 5%, about 6%, about 7%, about 8%, about 9%, about 10%, about 11%, about 12%, about 13%, about 14%, about 15%, about 16%, about 17%, about 18%, about 19%, or about 20%, by weight; and the at least one pharmaceutical diluent is present in the sustained release delivery system in an amount of about 40%, about 45%, about 50%, about 55%, about 60%, about 65%, about 70%, about 80%, or about 85% by weight. In some embodiments, the at least one hydrophilic compound is present in the sustained release delivery system in an amount of about 10%, about 11%, about 12%, about 13%, about 14%, about 15%, about 16%, about 17%, about 18%, about 19%, or about 20% by weight; the at least one cationic cross-linking agent is present in the sustained release delivery system in an amount of about 5%, about 6%, about 7%, about 8%, about 9%, about 10%, about 11%, about 12%, about 13%, about 14%, about 15%, by weight; and the at least one pharmaceutical diluent is present in the sustained release delivery system in an amount of about 55%, about 60%, about 65%, about 70%, about 80%, or about 85% by weight. In some embodiments, the at least one hydrophilic compound is present in the sustained release delivery system in an amount of about 8%, about 12%, or about 20% by weight; the at least one cationic cross-linking agent is present in the sustained release delivery system in an amount of about 10%, about 12%, or about 14% by weight; and the at least one pharmaceutical diluent is present in the sustained release delivery system in an amount of about 40%, about 60%, or about 70% by weight.

In some embodiments, the sustained release delivery system includes about 0.5% to about 80% locust bean gum, about 5% to about 80% xanthan gum, about 20% to about 80% mannitol and about 0.5% to 80% calcium sulfate dihydrate. In some embodiments, the sustained release delivery system includes about 12% to about 47% locust bean gum, about 8% to about 31% xanthan gum, about 20% to about 78% mannitol and about 0.5% to 25% calcium sulfate dihydrate. In some embodiments, the sustained release delivery system includes about 15% to about 25% locust bean gum, about 10% to about 20% xanthan gum, about 50% to about 85% mannitol and about 5% to 15% calcium sulfate dihydrate. In some embodiments, the sustained release delivery system includes about 18% locust bean gum, about 12% xanthan gum, about 60% mannitol and about 10% calcium sulfate dihydrate. In some embodiments, the sustained release delivery system includes about 12% locust bean gum, about 8% xanthan gum, about 70% mannitol and about 10% calcium sulfate dihydrate. In some embodiments, the sustained release delivery system includes about 20% locust bean gum, about 30% xanthan gum, about 40% mannitol and about 10% calcium sulfate dihydrate. In some embodiments, the sustained release delivery system includes about 30% locust bean gum, about 20% xanthan gum, about 40% mannitol and about 10% calcium sulfate dihydrate. In some embodiments, the sustained release delivery system includes about 42% locust bean gum, about 28% xanthan gum, about 20% mannitol and about 10% calcium sulfate dihydrate.

Two properties of the components of this sustained release system (e.g., the at least one hydrophilic compound and the at least one cross-linking agent; or the at least one hydrophilic compound and at least one cationic cross-linking compound) are that it forms a gel matrix upon exposure to liquids are fast hydration of the compounds/agents and the ability to form a gel matrix having a high gel strength. These two properties, which are needed to achieve a slow release gel matrix, are maximized by the particular combination of compounds (e.g., the at least one hydrophilic compound and the at least one cross-linking agent; or the at least one hydrophilic compound and the at least one cationic cross-linking compound). For example, hydrophilic compounds (e.g., xanthan gum) have excellent water-wicking properties that provide fast hydration. The combination of hydrophilic compounds with materials that are capable of cross-linking the rigid helical ordered structure of the hydrophilic compound (e.g., cross-linking agents and/or cationic cross-linking compounds) thereby acts synergistically to provide a higher than expected viscosity (i.e., high gel strength) of the gel matrix.

In some embodiments, the sustained release compositions are further admixed with one or more wetting agents (e.g., polyethoxylated castor oil, polyethoxylated hydrogenated castor oil, polyethoxylated fatty acid from castor oil, polyethoxylated fatty acid from hydrogenated castor oil) one or more lubricants (e.g., magnesium stearate, sodium stearyl fumarate, and the like), one or more buffering agents, one or more colorants, and/or other conventional ingredients.

In some embodiments, compositions employed in the present methods can contain additional pharmaceutical excipients. For example, in some embodiments, fumaric acid can be added to the formulations described herein.

In some embodiments, a non-functional coating, e.g., Opadry® can be added to the compositions described herein.

In some embodiments, the compositions described herein further include a second hydrophilic compound. In some embodiments, the second hydrophilic compound is a cellulose ether. In some embodiments, the second hydrophilic compound is a hydroxyalkyl cellulose or a carboxyalkyl cellulose. In some embodiments, the second hydrophilic compound is a hydroxyethyl cellulose, a hydroxypropyl cellulose, a hydroxypropylmethyl-cellulose, a carboxy methylcellulose, or a mixture thereof. In some embodiments, the second hydrophilic is an ethyl cellulose or wax (e.g., including without limitation cetyl alcohol, stearyl alcohol, white wax, or carnauba wax). The second hydrophilic compound is present in the formulation in an amount ranging from about 5% to about 45%, about 5% to about 25%, about 10% to about 20%, or 12% to about 18% by weight. In some embodiments, the second hydrophilic compound is present in the formulation in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, or about 45%.

In some embodiments, the weight ratio of the second hydrophilic compound to the nalbuphine, or a pharmaceutically acceptable salt, solvate or ester thereof ranges from about 5:1 to about 1:5, about 4:1 to about 1:4, about 3:1 to about 1:3, about 2:1 to about 1:2, about 1:1 to about 1:3, or about 1:1 to about 1:2. In some embodiments, the weight ratio of the second hydrophilic compound to the nalbuphine, or a pharmaceutically acceptable salt, solvate or ester thereof, is about 5:1, about 4:1, about 3:1, about 2:1, about 1:1, about 1:2, about 1:3, about 1:4, or about 1:5.

In some embodiments, the weight ratio of the second hydrophilic compound to the sustained release delivery system ranges from about 10:1 to about 1:10, about 8:1 to about 1:8, about 6:1 to about 1:6, about 4:1 to about 1:4, about 2:1 to about 1:3, about 1:1 to about 1:10, about 1:1 to about 1:6, or about 1:2 to about 1:6. In some embodiments, the weight ratio of the second hydrophilic compound to the sustained release delivery system is about 10:1, about 8:1, about 6:1, about 4:1, about 2:1, about 1:1, about 1:1.5, about 1:2, about 1:2.5, about 1:3, about 1:4, about 1:5, about 1:6, about 1:7, about 1:8, about 1:9 or about 1:10.

In some embodiments, the oral sustained release solid dosage formulations including from about 1 mg to 200 mg nalbuphine hydrochloride and about 10 mg to about 420 mg of a sustained release delivery system. In these embodiments, the sustained release delivery system includes about 12% to about 42% locust bean gum; about 8.0% to about 28% xanthan gum; about 20% to about 70% mannitol; and about 5% to about 20% calcium sulfate dihydrate. In some embodiments, the present methods can employ oral sustained release solid dosage formulations including from about 5 mg to about 80 mg nalbuphine hydrochloride and about 80 mg to about 360 mg of a sustained release delivery system. In some embodiments, the present methods can employ oral sustained release solid dosage formulations including from about 50 mg to about 150 mg nalbuphine hydrochloride and about 100 mg to about 300 mg of a sustained release delivery system.

In some embodiments, the present methods employ oral sustained release solid dosage formulations including about 15 mg nalbuphine hydrochloride, and from about 25 mg to about 225 mg, for example about 195 mg, of a sustained release delivery system. In these embodiments, the sustained release delivery system includes about 14% locust bean gum; about 9% xanthan gum; about 47% mannitol; and about 8% calcium sulfate dihydrate.

In some embodiments, the present methods employ oral sustained release solid dosage formulations including about 30 mg nalbuphine hydrochloride, and from about 25 mg to about 225 mg, for example about 180 mg, of a sustained release delivery system. In these embodiments, the sustained release delivery system includes about 18% locust bean gum; about 12% xanthan gum; about 60% mannitol; and about 10% calcium sulfate dihydrate.

In some embodiments, the present methods employ oral sustained release solid dosage formulations including about 60 mg nalbuphine hydrochloride, and from about 25 mg to about 225 mg, for example about 120 mg, of a sustained release delivery system. In these embodiments, the sustained release delivery system includes about 10% locust bean gum; about 12% xanthan gum; about 60% mannitol; and about 10% calcium sulfate dihydrate. In some embodiments, the present methods employ oral sustained release solid dosage formulations including from about 5 mg to about 80 mg nalbuphine hydrochloride and about 80 mg to about 360 mg of a sustained release delivery system.

In some embodiments, the present methods employ oral sustained release solid dosage formulations including about 120 mg nalbuphine hydrochloride, and from about 25 mg to about 250 mg, for example about 240 mg, of a sustained release delivery system. In these embodiments, the sustained release delivery system includes about 18% locust bean gum; about 12% xanthan gum; about 60% mannitol; and about 10% calcium sulfate dihydrate.

In some embodiments, the present methods employ oral sustained release solid dosage formulations including about 30 mg nalbuphine hydrochloride, and from about 25 mg to about 350 mg, for example about 270 mg or about 360 mg, of a sustained release delivery system. In these embodiments, the sustained release delivery system includes about 18% locust bean gum; about 12% xanthan gum; about 60% mannitol; and about 10% calcium sulfate dihydrate.

In some embodiments, the present methods employ oral sustained release solid dosage formulations including about 45 to about 60 mg nalbuphine hydrochloride and from about 100 mg to about 200 mg of a sustained release delivery system. In these embodiments, the sustained release delivery system includes about 15% to about 25% locust bean gum; about 10% to about 20% xanthan gum; about 50% to about 85% mannitol; and about 5% to about 15% calcium sulfate dihydrate.

In some embodiments, the present methods employ oral sustained release solid dosage formulations including about 30 mg nalbuphine hydrochloride, about 32.4 mg locust bean gum; about 21.6 mg xanthan gum; about 108 mg mannitol;

about 18 mg calcium sulfate dihydrate, about 35 mg hydroxypropylcellulose, and about 1.9 mg magnesium stearate.

In some embodiments, the present methods employ oral sustained release solid dosage formulations including about 29.8 mg nalbuphine hydrochloride, about 32.2 mg locust bean gum; about 21.4 mg xanthan gum; about 107 mg mannitol; about 18 mg calcium sulfate dihydrate, about 35 mg hydroxypropylcellulose, and about 1.9 mg magnesium stearate.

In some embodiments, the present methods employ oral sustained release solid dosage formulations including about 60 mg nalbuphine hydrochloride, about 21.6 mg locust bean gum; about 14.4 mg xanthan gum; about 72 mg mannitol; about 12 mg calcium sulfate dihydrate, about 30 mg hydroxypropylcellulose, and about 1.6 mg magnesium stearate.

In some embodiments, the present methods employ oral sustained release solid dosage formulations including about 59.5 mg nalbuphine hydrochloride, about 21.4 mg locust bean gum; about 14.3 mg xanthan gum; about 71 mg mannitol; about 12 mg calcium sulfate dihydrate, about 30 mg hydroxypropylcellulose, and about 1.6 mg magnesium stearate.

In some embodiments, the present methods employ oral sustained release solid dosage formulations including about 120 mg nalbuphine hydrochloride, about 43.2 mg locust bean gum; about 28.8 mg xanthan gum; about 144 mg mannitol; about 24 mg calcium sulfate dihydrate, about 60 mg hydroxypropylcellulose, and about 3.2 mg magnesium stearate.

In some embodiments, the present methods employ oral sustained release solid dosage formulations including about 119.0 mg nalbuphine hydrochloride, about 42.9 mg locust bean gum; about 25.6 mg xanthan gum; about 143 mg mannitol; about 24 mg calcium sulfate dihydrate, about 60 mg hydroxypropylcellulose, and about 3 mg magnesium stearate.

In some embodiments, the present methods employ oral sustained release solid dosage formulations including about 180 mg nalbuphine hydrochloride, about 64.8 mg locust bean gum; about 43.2 mg xanthan gum; about 216 mg mannitol; about 36 mg calcium sulfate dihydrate, about 90 mg hydroxypropylcellulose, about 5 mg magnesium stearate, and about 25 mg fumaric acid.

In some embodiments, the present methods employ oral sustained release solid dosage formulations including about 180 mg nalbuphine hydrochloride, about 48.6 mg locust bean gum; about 32.4 mg xanthan gum; about 162 mg mannitol; about 27 mg calcium sulfate dihydrate, about 60 mg hydroxypropylcellulose, about 4 mg magnesium stearate, and about 25 mg fumaric acid.

In some embodiments, the present methods employ oral sustained release solid dosage formulations including about 30 mg nalbuphine hydrochloride, about 32.4 mg locust bean gum; about 21.6 mg xanthan gum; about 108 mg mannitol; about 18 mg calcium sulfate dihydrate, about 35 mg hydroxypropylcellulose, about 1.9 mg magnesium stearate, and about 7.4 mg Opadry II White.

In some embodiments, the present methods employ oral sustained release solid dosage formulations including about 178.5 mg nalbuphine hydrochloride, about 48.2 mg locust bean gum; about 32.2 mg xanthan gum; about 161 mg mannitol; about 27 mg calcium sulfate dihydrate, about 60 mg hydroxypropylcellulose, about 4 mg magnesium stearate, and about 25 mg fumaric acid.

The sustained release formulations of nalbuphine are orally administrable solid dosage formulations. Nonlimiting examples of oral solid dosage formulations include tablets, capsules including a plurality of granules, sublingual tablets, powders, granules, syrups, and buccal dosage forms or devices (e.g., buccal patches, tablets, etc.). In some embodiments, tablets have an enteric coating or a hydrophilic coating.

The sustained release delivery system is prepared by dry granulation or wet granulation, before the nalbuphine, or pharmaceutically acceptable salt, solvate or ester thereof, is added, although the components can be held together by an agglomeration technique to produce an acceptable product. In the wet granulation technique, the components (e.g., hydrophilic compounds, cross-linking agents, pharmaceutical diluents, cationic cross-linking compounds, hydrophobic polymers, etc.) are mixed together and then moistened with one or more liquids (e.g., water, propylene glycol, glycerol, alcohol) to produce a moistened mass that is subsequently dried. The dried mass is then milled with conventional equipment into granules of the sustained release delivery system. Thereafter, the sustained release delivery system is mixed in the desired amounts with the nalbuphine, or the pharmaceutically acceptable salt, solvate or ester thereof, and, optionally, one or more wetting agents, one or more lubricants, one or more buffering agents, one or more coloring agents, one or more second hydrophilic compounds, or other conventional ingredients, to produce a granulated composition. The sustained release delivery system and the nalbuphine can be blended with, for example, a high shear mixer. The nalbuphine is preferably finely and homogeneously dispersed in the sustained release delivery system. The granulated composition, in an amount sufficient to make a uniform batch of tablets, is subjected to tableting in a conventional production scale tableting machine at typical compression pressures, i.e., about 2,000-16,000 psi. In some embodiments, the mixture should not be compressed to a point where there is subsequent difficulty with hydration upon exposure to liquids.

In some embodiments, the nalbuphine formulation is prepared by dry granulation or wet granulation. The components of the sustained release delivery system are added, along with the nalbuphine, or a pharmaceutically acceptable salt, solvate or ester thereof. Alternatively, all of the components can be held together by an agglomeration technique to produce an acceptable product. In the wet granulation technique, nalbuphine, or pharmaceutically salt, solvate or ester thereof, and the components (e.g., hydrophilic compounds, cross-linking agents, pharmaceutical diluents, cationic cross-linking compounds, hydrophobic polymers, etc.) are mixed together and then moistened with one or more liquids (e.g., water, propylene glycol, glycerol, alcohol) to produce a moistened mass that is subsequently dried. The dried mass is then milled with conventional equipment into granules. Optionally, one or more wetting agents, one or more lubricants, one or more buffering agents, one or more coloring agents, one or more second hydrophilic compounds, or other conventional ingredients, are also added to the granulation. The granulated composition, in an amount sufficient to make a uniform batch of tablets, is subjected to tableting in a conventional production scale tableting machine at typical compression pressures, i.e., about 2,000-16,000 psi. In some embodiments, the mixture should not be compressed to a point where there is subsequent difficulty with hydration upon exposure to liquids.

The average particle size of the granulated composition is from about 50 μm to about 400 μm by weight. In some embodiments, the average particle size by weight is from about 185 µm to about 265 The average density of the granulated composition is from about 0.3 g/mL to about 0.8 g/mL. In some embodiments, the average density is from about 0.5 g/mL to about 0.7 g/mL. The tablets formed from the granulations are generally from about 4 Kp to about 22 Kp hardness. The average flow of the granulations is from about 25 to about 40 g/sec.

In some embodiments, the present methods can employ a multilayer solid dosage form, in which the layers are formulated to release the nalbuphine hydrochloride at different rates. For example, in some embodiments, the second layer is an extended release layer that includes nalbuphine, or a pharmaceutically acceptable salt, solvate or ester thereof, and a sustained release delivery system designed to release the nalbuphine, or the pharmaceutically acceptable salt, solvate or ester thereof, at a controlled rate so that therapeutically effective blood levels are maintained over an extended period of time (e.g., from about 8 to about 12 hours). The first layer is an immediate release layer that includes a formulation of nalbuphine, or a pharmaceutically acceptable salt, solvate or ester thereof, designed to release the nalbuphine, or the pharmaceutically acceptable salt, solvate or ester thereof, at a rate that is faster than the rate of the second layer to achieve a therapeutically effective blood level in an immediate period of time (e.g., from about 1 to about 2 hours). In some embodiments, the first layer includes a sustained release delivery system. In some embodiments, the first layer does not include a sustained release delivery system.

In some embodiments, the weight ratio of the second layer to the first layer is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, about 2:1 to about 1:2. In some embodiments, the weight ratio of the second layer to the first layer is about 5:1 to about 1:5. In a further embodiment, the weight ratio of the second layer to the first layer is about 1:1 to about 1:2. In some embodiments, the weight ratio of the second layer to the first layer is about 1:1, about 1:1.2, about 1:1.4, about 1:1.6, about 1:1.8, or about 1:2. In some embodiments, the weight ratio of the second layer to the first layer is about 1:2. In some embodiments, the weight ratio of the second layer to the first layer is about 1:1.4. In some embodiments, the weight ratio of the second layer to the first layer is about 3:1, about 2.5:1, about 2:1, about 1.5:1. In some embodiments, the weight ratio of the second layer to the first layer is about 2.5:1.

The sustained release delivery system of the multilayer dosage form includes (i) at least one hydrophilic compound, at least one cross-linking agent, and at least one pharmaceutical diluent; (ii) at least one hydrophilic compound, at least one cross-linking agent, at least one pharmaceutical diluent, and at least one cationic cross-linking agent different from the first cross-linking agent; or (iii) at least one hydrophilic compound, at least one cationic cross-linking compound, and at least one pharmaceutical diluent. In some embodiments, when the first layer includes a sustained release delivery system, the sustained release delivery system of the first layer includes the same components as the sustained release delivery system of the second layer (e.g., both the first and second layers are one of embodiments (i)-(iii), listed above). In some embodiments, the sustained release delivery system of the first layer includes different components as the sustained release delivery system of the second layer (e.g., the first layer is embodiment (i), listed above, while the second layer is embodiment (iii), listed above). It is recognized that the sustained release delivery system of either layer can be one of embodiments (i)-(iii) listed above. Moreover, it is recognized that in some embodiments, the first layer does not include a sustained release delivery system.

The sustained release delivery system is generally present in the second layer (e.g., extended release layer) in an amount ranging from about 10 mg to about 420 mg. In some embodiments, the sustained release delivery system is present in the second layer in an amount ranging from about 110 mg to about 200 mg. In some embodiments, the sustained release delivery system is present in the second layer in an amount ranging from about 110 mg to about 150 mg. In some embodiments, the sustained release delivery system is present in the second layer in an amount ranging from about 90 mg to about 150 mg. In some embodiments, the sustained release delivery system is present in the second layer in an amount of about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg. In some embodiments, the sustained release delivery system is present in the second layer in an amount of about 123 mg. In some embodiments, the sustained release delivery system is present in the second layer in an amount of about 101 mg. In some embodiments, the sustained release delivery system is present in the second layer in an amount of about 92 mg. In some embodiments, the sustained release delivery system is present in the second layer in an amount of about 112.5 mg. In some embodiments, the sustained release delivery system is present in the second layer in an amount of about 135 mg. In some embodiments, the sustained release delivery system is present in the second layer in an amount of about 150 mg.

Nalbuphine, or a pharmaceutically acceptable salt, solvate or ester thereof, is generally present in the second layer in an amount ranging from about 15 mg to about 60 mg. In some embodiments, nalbuphine, or a pharmaceutically acceptable salt, solvate or ester thereof, is present in the second layer in an amount ranging from about 30 mg to about 60 mg. In some embodiments, nalbuphine, or a pharmaceutically acceptable salt, solvate or ester thereof, is present in the second layer in an amount ranging from about 45 mg to about 60 mg. In some embodiments, nalbuphine, or a pharmaceutically acceptable salt, solvate or ester thereof, is present in the second layer in an amount of about 15 mg. In some embodiments, nalbuphine, or a pharmaceutically acceptable salt, solvate or ester thereof, is present in the second layer in an amount of about 30 mg. In some embodiments, nalbuphine, or a pharmaceutically acceptable salt, solvate or ester thereof, is present in the second layer in an amount of about 45 mg. In some embodiments, nalbuphine, or a pharmaceutically acceptable salt, solvate or ester thereof, is present in the second layer in an amount of about 15 mg, about 30 mg, about 60 mg, about 90 mg, about 120 mg, or about 180 mg.

In some embodiments, the weight ratio of nalbuphine, or a pharmaceutically acceptable salt, solvate or ester thereof, to the sustained release delivery system in the second layer is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, or about 2:1 to about 1:2. In some embodiments, the weight ratio of nalbuphine, or a pharmaceutically acceptable salt, solvate or ester thereof, to the sustained release delivery system in the second layer is about 1:2 to about 1:4. In some embodiments, the weight ratio of nalbuphine, or a pharmaceutically acceptable salt, solvate or ester thereof, to the sustained release delivery system in the second layer is about 1:1 to about 1:5. In some embodiments, the weight ratio of nalbuphine, or a pharmaceutically acceptable salt, solvate or ester thereof, to the sustained release delivery system in the second layer is about 1:1, about 1:1.2, about 1:1.4, about 1:1.6, about 1:1.8, about 1:2, about 1:2.5, about 1:3, or about 1:3.5. In some embodiments, the weight ratio of nalbuphine, or a pharmaceutically acceptable salt, solvate or ester thereof, to the sustained release delivery system in the second layer is about 1:2.5. In some embodiments, the weight ratio of nalbuphine, or a pharmaceutically acceptable salt, solvate or ester thereof, to the sustained release delivery system in the second layer is about 1:3.3. In a further embodiment, the weight ratio of nalbuphine, or a pharmaceutically acceptable salt, solvate or ester thereof, to the sustained release delivery system in the second layer is about 1:3. In some embodiments, the ratio of nalbuphine, or a pharmaceutically acceptable salt, solvate or ester thereof, to the sustained release delivery system in the second layer is about 1:2.

When the sustained release delivery system is present in the first layer (e.g., immediate release layer), it is generally present in an amount ranging from about 0 mg to about 50 mg. In some embodiments, the sustained release delivery system is present in the first layer in an amount ranging from about 5 mg to about 25 mg or from about 5 mg to about 15 mg. In some embodiments, the sustained release delivery system is present in the first layer in an amount of about 3 mg to about 9 mg. In some embodiments, the sustained release delivery system is present in the first layer in an amount of about 4 mg to about 6 mg. In some embodiments, the sustained release delivery system is present in the first layer in an amount of about 2 mg, about 4 mg, about 6 mg, about 8 mg, about 10 mg, about 12 mg, about 14 mg, about 15 mg, about 16 mg, about 18 mg, about 20 mg about 25 mg, about 30 mg, about 35 mg, about 40 mg, about 45 mg or about 50 mg. In some embodiments, the sustained release delivery system is present in the first layer in an amount of about 6 mg.

In some embodiments, nalbuphine, or a pharmaceutically acceptable salt, solvate or ester thereof, is generally present in the first layer (e.g., immediate release layer) in an amount ranging from about 5 mg to about 180 mg. In some embodiments, nalbuphine, or a pharmaceutically acceptable salt, solvate or ester thereof, is present in the first layer in an amount ranging from about 5 mg to about 25 mg or from about 10 mg to about 20 mg. In some embodiments, the nalbuphine, or a pharmaceutically acceptable salt, solvate or ester thereof, is present in the first layer in an amount of about 5 mg, about 10 mg, about 11 mg, about 12 mg, about 13 mg, about 14 mg, about 15 mg, about 16 mg, about 17 mg, about 18 mg, about 19 mg, about 20 mg, about 25 mg, about 30 mg, about 35 mg, about 40 mg, about 45 mg or about 50 mg. In some embodiments, nalbuphine, or a pharmaceutically acceptable salt, solvate or ester thereof, is present in the first layer in an amount of about 15 mg, about 30 mg, about 60 mg, about 90 mg, about 120 mg, or about 180 mg.

In some embodiments, when the first layer includes a sustained release delivery system, the ratio of nalbuphine, or pharmaceutically acceptable salt, solvate or ester thereof, to the sustained release delivery system in the first layer is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, about 2:1 to about 1:2. In some embodiments, the ratio of nalbuphine, or pharmaceutically acceptable salt, solvate or ester thereof, to the sustained release delivery system in the first layer is about 2:1 to about 4:1. In some embodiments, the ratio of nalbuphine, or pharmaceutically acceptable salt, solvate or ester thereof, to the sustained release delivery system in the first layer is about 5:1, about 4.5:1, about 4:1, about 3.5:1, about 3:1, about 2.5:1, about 2:1, about 1.5:1, or about 1:1. In some embodiments, the ratio of nalbuphine, or pharmaceutically acceptable salt, solvate or ester thereof, to the sustained release delivery system in the first layer is about 2.5:1. In some embodiments, the ratio of nalbuphine, or pharmaceutically acceptable salt, solvate or ester thereof, to the sustained release delivery system in the first layer is about 3:1.

In some embodiments, the multilayer dosage form further includes a pharmaceutical disintegrant. The disintegrant promotes the dissolution and absorption of nalbuphine, or a pharmaceutically acceptable salt, solvate or ester thereof, from the immediate release layer. Nonlimiting examples of pharmaceutical disintegrants include croscarmellose sodium, starch glycolate, crospovidone, and unmodified starch. In some embodiments, the disintegrant is in the first layer (i.e., the immediate release layer), of the dosage form. The disintegrant is generally present in the layer in an amount of about 1.5 mg to about 4.5 mg. In some embodiments, the disintegrant is present in an amount of about 3 mg. In some embodiments, the disintegrant is present in the layer in an amount of about 2-10% by weight. In some embodiments, the disintegrant is present in the layer in an amount of about 5% by weight. When the layer contains a sustained release delivery system, the weight ratio of the sustained release delivery system to the disintegrant is in a range of about 5:1 to about 1:5. In some embodiments, the ratio of the sustained release delivery system to the disintegrant is in a range of about 1:1 to about 3:1. In some embodiments, the ratio of the sustained release delivery system to the disintegrant is in a range of about 2:1.

In some embodiments, the multilayer tablets are prepared by first preparing the immediate release layer and extended release layer blends separately. The extended release layer is prepared as described above. The wet granulation of the extended release layer is then dried and milled to an appropriate size. Magnesium stearate is added and mixed with the milled granulation. The immediate release layer is prepared by first mixing the nalbuphine, or the pharmaceutically acceptable salt, solvate or ester thereof, with one or more diluents (e.g., microcrystalline cellulose). This mix is then optionally mixed with one or more disintegrants. The blend is mixed with magnesium stearate. Finally, the immediate release layer blend and the extended release layer blend are compressed into multi-layer (e.g., bi-layer) tablets.

In some embodiments, the chemistry of certain of the components of the formulation, such as the hydrophilic compound (e.g., xanthan gum), is such that the components are considered to be self-buffering agents which are substantially insensitive to the solubility of the nalbuphine and the pH changes along the length of the gastrointestinal tract. Moreover, the chemistry of the components is believed to be similar to certain known muco-adhesive substances, such as polycarbophil. Muco-adhesive properties are desirable for buccal delivery systems. Thus, the sustained release formulation can loosely interact with the mucin in the gastrointestinal tract and thereby provide another mode by which a constant rate of delivery of the nalbuphine is achieved.

The phenomenon discussed above (muco-adhesive properties) is a mechanism by which the sustained release formulations can interact with the mucin and fluids of the gastrointestinal tract and provide a constant rate of delivery of the nalbuphine.

When measured by USP Procedure Drug Release General Chapter <711> Dissolution, (incorporated by reference herein in its entirety), the sustained release formulations employed in the present methods generally exhibit an in vitro dissolution of about 15% to about 50% by weight nalbuphine after 1 hour, about 45% to about 80% by weight nalbuphine after 4 hours, or at least about 80% by weight nalbuphine after 10 hours. In some embodiments, the in vitro and in vivo release characteristics of the sustained release formulations are modified using mixtures of one or more different water insoluble and/or water soluble compounds, using different plasticizers, varying the thickness of the sustained release film, including providing release-modifying compounds in the coating, and/or by providing passageways through the coating. In some embodiments, the dissolution rate is determined using apparatus USP Type 111/250 mL at pH 6.8, 37° C. and 15 dpm. In some embodiments, the dissolution rate is determined using apparatus USP Type 111/250 mL performed in pH change (0-1 hours pH 1.2, after hour 1 pH 4.5, after hour 2 pH 6.8) at 37° C. and 15 dpm.

In some embodiments, the sustained release formulation has an in vitro dissolution of about 50% to about 100% by weight nalbuphine after about 6 hours. In some embodiments, the sustained release formulation has an in vitro dissolution of about 75% to about 100% by weight nalbuphine after about 6 hours. In some embodiments, the sustained release formulation has an in vitro dissolution of about 75% to about 100% by weight nalbuphine from about 6 hours to about 8 hours. In further embodiments, the sustained release formulation has an in vitro dissolution of about 80% to about 100% by weight nalbuphine after about 12 hours. In still some embodiments, the sustained release formulation has an in vitro dissolution of about 80% to about 100% by weight nalbuphine from about 12 hours to about 24 hours. In some embodiments, the sustained release formulation has an in vitro dissolution of about 80% to about 100% after about 8 hours to about 12 hours. In some embodiments, the sustained release formulation has an in vitro dissolution of about 15% to about 75% by weight nalbuphine after about 1 hour. In still further embodiments, the sustained release formulation has an in vitro dissolution of about 50% by weight nalbuphine after about 1 hour. In some embodiments, the sustained release formulation has an in vitro dissolution of about 50% by weight nalbuphine after about 1 hour and about 75% to about 100% by weight nalbuphine from about 6 hours to about 8 hours. In some embodiments, the sustained release formulation has an in vitro dissolution of about 50% by weight nalbuphine after about 1 hour and about 75% to about 100% by weight nalbuphine from about 8 hours to about 12 hours. In some embodiments, the sustained release formulation has an in vitro dissolution of about 50% by weight nalbuphine after about 1 hour and about 75% to about 100% by weight nalbuphine from about 12 hours to about 24 hours. In some embodiments, the sustained release formulation has an in vitro dissolution of about 50% by weight nalbuphine after about 1 hour and about 80% to about 100% by weight nalbuphine after about 12 hours.

Where the tablet is a multilayer dosage form having a first extended release layer and a second, immediate release, layer, the sustained release formulation has an in vitro dissolution of about 25% to about 75% by weight nalbuphine after about 1 hour. In some embodiments, the multilayer dosage form has an in vitro dissolution of about 25% by weight nalbuphine after about 1 hour. In some embodiments, the multilayer dosage form has an in vitro dissolution of about 50% by weight nalbuphine after about 1 hour. In some embodiments, the multilayer dosage form has an in vitro dissolution of about 75% to about 100% nalbuphine after about 6-8 hours. In some embodiments, the multilayer dosage form has an in vitro dissolution of about 75% to about 100% nalbuphine after about 8-12 hours. In some embodiments, the multilayer dosage form has an in vitro dissolution of about 75% to about 100% nalbuphine after about 12-24 hours. In some embodiments, the multilayer dosage form has an in vitro dissolution of about 75% to about 100% nalbuphine after about 12 hours.

In some embodiments, when administered orally to patients having either normal or impaired (e.g., reduced) kidney function, the sustained release formulations described herein exhibit the following in vivo characteristics: (a) a peak plasma level of nalbuphine occurs within about 4 hours to about 6 hours, e.g., for patients with uremic pruritus or renal impairment, or about 3 hours to about 5 hours, e.g., for patients without renal impairment after administration; (b) onset of the nalbuphine therapeutic effect from about 30 minutes of dosing to within about 6 hours of dosing; (c) duration of the nalbuphine therapeutic effect is about 2 to about 24 hours; and (d) the relative nalbuphine bioavailability is about 0.5, about 1, about 1.5 or between about 0.5 to about 1.5 compared to an orally administered aqueous solution of nalbuphine. The time of onset for a therapeutic effect can depend on at least on dosing and the severity of the patient's symptoms (e.g., pruritic symptoms). In some embodiments, the duration of the nalbuphine therapeutic effect is at least about 8 hours. In some embodiments, the duration of the nalbuphine therapeutic effect is at least about 9 hours. In some embodiments, the duration of the nalbuphine therapeutic effect is at least about 10 hours. In some embodiments, the duration of the nalbuphine therapeutic effect is at least about 11 hours. In some embodiments, the duration of the nalbuphine therapeutic effect is at least about 12 hours. In some embodiments, the duration of nalbuphine therapeutic effect is about 6, hours, 8 hours, 10 hours, 12 hours, 15 hours, or 18 hours. In some embodiments, the relative nalbuphine bioavailability is about 0.94 compared to an orally administered aqueous solution of nalbuphine. In some embodiments, the relative nalbuphine bioavailability is about 1.35 compared to an orally administered aqueous solution of nalbuphine.

In some embodiments, the sustained release nalbuphine formulations provide an oral unit dosage form including nalbuphine, or a pharmaceutically acceptable salt, solvate or ester thereof. The oral dosage form provides therapeutic effect (e.g., reduced pruritus) over a period of at least about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours or about 24 hours. In some embodiments, the oral dosage form provides a therapeutic effect over a period of about 6-18 hours, about 8-16 hours, about 8-12 hours, about 8 to about 24 hours, about 12 to about 24 hours, about 18 to about 24 hours, or about 8-10 hours. The oral dosage form provides a therapeutic effect over a period of about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours or about 24 hours.

In some embodiments, the oral dosage form provides an anti-pruritic effect as well as breaking the cycle effect, e.g., the itchy sensation does not return after certain treatment period.

In some embodiments, the oral dosage form provides a blood plasma level of nalbuphine characterized by one or more peaks followed by a plateau region. The plateau region is characterized as having a relatively consistent blood plasma level of nalbuphine (e.g., the blood plasma level of nalbuphine does not consistently increase or decrease from time point to time point). In some embodiments, the plateau region is characterized as having a consistent average blood plasma level of nalbuphine. The plateau region is contrasted with the region following the plateau region, in which the blood plasma level of nalbuphine generally decreases from one time point to the next. In some embodiments, the plateau region has a duration of at least about 1 hour, about 2 hours, about 3 hours, about 4 hours, about 5 hours, about 6 hours, about 7 hours, about 8 hours, about 9 hours, about 10 hours, about 11 hours or about 12 hours. In some embodiments, the plateau region has a duration from about 1 hour to about 12 hours, from about 2 hours to about 10 hours, from about 2 hours to about 8 hours, from about 2 hours to about 7 hours or from about 4 hours to about 10 hours, from about 4 hours to about 8 hours, or from about 4 hours to about 6 hours. In some embodiments, the blood plasma level of nalbuphine at each time point in the plateau region ranges from about 75% to about 125% of the mean blood plasma level in the plateau region. In some embodiments, the blood plasma level of nalbuphine at each time point in the plateau region ranges from about 80% to about 120% of the mean blood plasma level in the plateau region. In some embodiments, the blood plasma level of nalbuphine at each time point in the plateau region ranges from about 85% to about 115% of the mean blood plasma level in the plateau region. In some embodiments, the blood plasma level of nalbuphine at each time point in the plateau region ranges from about 90% to about 110% of the mean blood plasma level in the plateau region.

In some embodiments, the minimum blood plasma level of nalbuphine observed during the plateau region is not more than about 25% below the mean blood plasma level for all time points in the plateau region. In some embodiments, the minimum blood plasma level of nalbuphine observed during the plateau region is not more than about 20% below the mean blood plasma level in the plateau region. In some embodiments, the minimum blood plasma level of nalbuphine observed during the plateau region is not more than about 15% below the mean blood plasma level in the plateau region. In some embodiments, the minimum blood plasma level of nalbuphine observed during the plateau region ranges from about 75% to about 100% of the mean blood plasma level in the plateau region. In some embodiments, the minimum blood plasma level of nalbuphine observed during the plateau region ranges from about 80% to about 100% of the mean blood plasma level in the plateau region. In some embodiments, the minimum blood plasma level of nalbuphine observed during the plateau region ranges from about 85% to about 100% of the mean blood plasma level in the plateau region. In some embodiments, the minimum blood plasma level of nalbuphine observed during the plateau region ranges from about 80% to about 95% of the mean blood plasma level in the plateau region.

Dosing

The present disclosure provides methods for treating a nalbuphine-treatable disorder in a patient with a Child Pugh score of A, B, or C by administering an effective amount of nalbuphine, or a pharmaceutically acceptable salt, solvate or ester thereof. An effective amount is an amount sufficient to eliminate or significantly reduce symptoms associated with a nalbuphine-treatable disorder or to alleviate those symptoms. Formulations employed in the present methods can incorporate nalbuphine, or a pharmaceutically acceptable salt, or ester thereof, in a sustained release formulation such that the formulation provides therapeutically effective blood plasma levels of nalbuphine for the treatment of a nalbuphine-treatable disorder in a patient with a Child Pugh score of A, B, or C.

According to some embodiments of the present disclosure, administering of nalbuphine, or a pharmaceutically acceptable salt, solvate or ester thereof, provides statistically significant therapeutic effect. In some embodiments, the statistically significant therapeutic effect is determined based on one or more standards or criteria provided by one or more regulatory agencies in the United States, e.g., FDA or other countries. In some embodiments, the statistically significant therapeutic effect is determined based on results obtained from regulatory agency approved clinical trial set up and/or procedure.

In some embodiments, the statistically significant therapeutic effect is determined based on a patient population of at least 20, 50, 60, 100, 200, 300, 400, 500, 600, 700, 800, 900, 1000 or 2000. In some embodiments, the statistically significant therapeutic effect is determined based on data obtained from randomized and double blinded clinical trial set up. In some embodiments, the statistically significant therapeutic effect is determined based on data with a p value of less than or equal to about 0.05, 0.04, 0.03, 0.02 or 0.01. In some embodiments, the statistically significant therapeutic effect is determined based on data with a confidence interval greater than or equal to 95%, 96%, 97%, 98% or 99%. In some embodiments, the statistically significant therapeutic effect is determined on approval of Phase III clinical trial of the methods provided by the present disclosure, e.g., by FDA in the US.

In some embodiments, the statistically significant therapeutic effect is determined by a randomized double blind clinical trial of patients treated with nalbuphine, or a pharmaceutically acceptable salt, solvate or ester thereof, and optionally in combination with standard care. In some embodiment, the statistically significant therapeutic effect is determined by a randomized clinical trial and using Numerical Rating Scale (NRS) as primary efficacy parameter and optionally in combination with any other commonly accepted criteria for pruritus assessment.

In general, statistical analysis can include any suitable method permitted by a regulatory agency, e.g., FDA in the US or Europe or any other country. In some embodiments, statistical analysis includes non-stratified analysis, log-rank analysis, e.g., from Kaplan-Meier, Jacobson-Truax, Gulliken-Lord-Novick, Edwards-Nunnally, Hageman-Arrindel and Hierarchical Linear Modeling (HLM) and Cox regression analysis.

In some embodiments, methods for treating (e.g. safely treating) hepatically impaired patients with a Child-Pugh score of A comprises administering a daily dose from about 14 mg to about 324 mg of an Equivalent Amount of Nalbuphine Free Base. In some embodiments, about 14 mg of the Equivalent Amount of Nalbuphine Free Base is administered once a day. In some embodiments, about 28 mg of the Equivalent Amount of Nalbuphine Free Base is administered once a day. In some embodiments, about 54 mg of the Equivalent Amount of Nalbuphine Free Base is administered once a day. In some embodiments, about 81 mg of the Equivalent Amount of Nalbuphine Free Base is administered once a day. In some embodiments, about 108 mg of the Equivalent Amount of Nalbuphine Free Base is administered once a day. In some embodiments, about 162 mg of the Equivalent Amount of Nalbuphine Free Base is administered once a day. In some embodiments, about 324 mg of the Equivalent Amount of Nalbuphine Free Base is administered once a day. In some embodiments, about 14 mg of the Equivalent Amount of Nalbuphine Free Base is administered twice a day. In some embodiments, about 28 mg of the Equivalent Amount of Nalbuphine Free Base is administered twice a day. In some embodiments, about 54 mg of the Equivalent Amount of Nalbuphine Free Base is administered twice a day. In some embodiments, about 81 mg of the Equivalent Amount of Nalbuphine Free Base is administered twice a day. In some embodiments, about 108 mg of the Equivalent Amount of Nalbuphine Free Base is administered twice a day. In some embodiments, about 162 mg of the Equivalent Amount of Nalbuphine Free Base thereof is administered twice a day.

In some embodiments, methods for treating a nalbuphine-treatable disorder in a patient with a Child-Pugh score of A comprises administering a daily dose from about 15 mg to about 360 mg of the nalbuphine, or a pharmaceutically acceptable salt thereof. In some embodiments, about 15 mg of nalbuphine, or a pharmaceutically acceptable salt or ester thereof, is administered once a day. In some embodiments, about 30 mg of nalbuphine, or a pharmaceutically acceptable salt or ester thereof, is administered once a day. In some embodiments, about 60 mg of nalbuphine, or a pharmaceutically acceptable salt or ester thereof, is administered once a day. In some embodiments, about 90 mg of nalbuphine, or a pharmaceutically acceptable salt or ester thereof, is administered once a day. In some embodiments, about 120 mg of nalbuphine, or a pharmaceutically acceptable salt or ester thereof, is administered once a day. In some embodiments, about 180 mg of nalbuphine, or a pharmaceutically acceptable salt or ester thereof, is administered once a day. In some embodiments, about 360 mg of nalbuphine, or a pharmaceutically acceptable salt or ester thereof, is administered once a day. In some embodiments, about 30 mg of nalbuphine, or a pharmaceutically acceptable salt or ester thereof, is administered twice a day. In some embodiments, about 60 mg of nalbuphine, or a pharmaceutically acceptable salt or ester thereof, is administered twice a day. In some embodiments, about 90 mg of nalbuphine, or a pharmaceutically acceptable salt or ester thereof, is administered twice a day. In some embodiments, about 120 mg of nalbuphine, or a pharmaceutically acceptable salt or ester thereof, is administered twice a day. In some embodiments, about 180 mg of nalbuphine, or a pharmaceutically acceptable salt or ester thereof, is administered twice a day.

In some embodiments, the methods of treating a nalbuphine-treatable disorder in a patient with a Child Pugh score of A, B, or C described herein further includes a step of titrating the dose of nalbuphine, or a pharmaceutically acceptable salt thereof, for at least about one week until a steady state is achieved in the patient. In some embodiments, the titration is conducted for about 2 weeks until a steady state is achieved in the patient. In some embodiments, the titration is conducted for about 7 days to about 30 days until a steady state is achieved in the patient. In some embodiments, the titration is conducted for about 12 days to about 20 days until a steady state is achieved in the patient.

In some embodiments, the methods of treating a nalbuphine-treatable disorder in a patient with a Child Pugh score of A, B, or C described herein further includes a step of titrating the dose of an Equivalent Amount of Nalbuphine Free Base for at least about one week until a steady state is achieved in the patient. In some embodiments, the titration is conducted for about 2 weeks until a steady state is achieved in the patient. In some embodiments, the titration is conducted for about 7 days to about 30 days until a steady state is achieved in the patient. In some embodiments, the titration is conducted for about 12 days to about 20 days until a steady state is achieved in the patient. In some embodiments, the titration is conducted until a tolerable and therapeutically effective dose of an Equivalent Amount of Nalbuphine Free Base is achieved in the patient. In some embodiments, the titration is conducted for at least about 1-14 days, including at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, or at least about 14 days, including all ranges and values therebetween. In some embodiments, the titration is conducted for at least about one week. In some embodiments, the titration is conducted for at least about two weeks.

Throughout the present disclosure, the dose titration schedules disclosed herein are generally expressed in terms of the fastest titration (i.e., the least number of days) to the maximum safe and tolerable dose. However, the present disclosure also contemplates embodiments wherein the rate of titration is slower than the rates disclosed in the titration schedules herein (for example, the number of days to the maximum safe and tolerable dose is increased by using smaller incremental increases in the dose escalation). For example, in some embodiments, the titration rate is about 30%, about 40%, about 50%, about 60%, about 70%, about 80%, about 90% or more, of the titration rate in a titration schedule disclosed herein. In some embodiments, the patient's dose may be titrated to the maximum dose of a titration schedule disclosed herein. In some embodiments, the patient may be titrated to a therapeutically effective dose that is less than the maximum dose of a disclosed titration schedule. For example, in some embodiments, the patient's titration period ends on Day 4, Day 5, Day 6, Day 7, Day 8, Day 9, Day 10, Day 11, Day 12, or Day 13 because the patient achieves a safe and effective dose.

In some embodiments, hepatically impaired patients with a Child-Pugh score of A are administered nalbuphine, or a pharmaceutically acceptable salt thereof according to the following titration schedule:

| Day | AM dosage (mg) | PM dosage (mg) |
| --- | --- | --- |
| Day 1 | 0 | 30 |
| Day 2 | 0 | 30 |
| Day 3 | 30 | 30 |
| Day 4 | 30 | 30 |
| Day 5 | 30 | 60 |
| Day 6 | 60 | 60 |
| Day 7 | 60 | 60 |
| Day 8 | 60 | 90 |
| Day 9 | 90 | 90 |
| Day 10 | 90 | 90 |
| Day 11 | 90 | 120 |
| Day 12 | 120 | 120 |
| Day 13 | 120 | 120 |
| Day 14 | 120 | 180 |

In some embodiments, hepatically impaired patients with a Child-Pugh score of A are administered an Equivalent Amount of Nalbuphine Free Base according to the following titration schedule:

| Day | AM dosage (mg) | PM dosage (mg) |
| --- | --- | --- |
| Day 1 | 0 | 28 |
| Day 2 | 0 | 28 |
| Day 3 | 28 | 28 |
| Day 4 | 28 | 28 |
| Day 5 | 28 | 54 |
| Day 6 | 54 | 54 |
| Day 7 | 54 | 54 |
| Day 8 | 54 | 81 |
| Day 9 | 81 | 81 |
| Day 10 | 81 | 81 |
| Day 11 | 81 | 108 |
| Day 12 | 108 | 108 |
| Day 13 | 108 | 108 |
| Day 14 | 108 | 162 |

In some embodiments, hepatically impaired patients with a Child-Pugh score of A are administered nalbuphine, or a pharmaceutically acceptable salt thereof for fourteen days according to the dose schedule provided in the following table:

| Day | AM dosage (mg) | PM dosage (mg) |
| --- | --- | --- |
| Day 1 | 0 | 30 |
| Day 2 | 0 | 30 |
| Day 3 | 30 | 30 |
| Day 4 | 30 | 30 |
| Day 5 | 30 | 60 |
| Day 6 | 60 | 60 |
| Day 7 | 60 | 60 |
| Day 8 | 60 | 90 |
| Day 9 | 90 | 90 |
| Day 10 | 90 | 90 |
| Day 11 | 90 | 120 |
| Day 12 | 120 | 120 |
| Day 13 | 120 | 120 |
| Day 14 | 120 | 120. |

In some embodiments, hepatically impaired patients with a Child-Pugh score of A are administered an Equivalent Amount of Nalbuphine Free Base, or a pharmaceutically acceptable salt thereof for fourteen days according to the dose schedule provided in the following table:

| Day | AM dosage (mg) | PM dosage (mg) |
| --- | --- | --- |
| Day 1 | 0 | 28 |
| Day 2 | 0 | 28 |
| Day 3 | 28 | 28 |
| Day 4 | 28 | 28 |
| Day 5 | 28 | 54 |
| Day 6 | 54 | 54 |
| Day 7 | 54 | 54 |
| Day 8 | 54 | 81 |
| Day 9 | 81 | 81 |
| Day 10 | 81 | 81 |
| Day 11 | 81 | 108 |
| Day 12 | 108 | 108 |
| Day 13 | 108 | 108 |
| Day 14 | 108 | 108. |

In some embodiments, hepatically impaired patients with a Child-Pugh score of A are administered nalbuphine, or a pharmaceutically acceptable salt thereof according to the following titration schedule:

| Day | AM dosage (mg) | PM dosage (mg) |
| --- | --- | --- |
| Day 1 | 0 | 30 |
| Day 2 | 0 | 30 |
| Day 3 | 30 | 30 |
| Day 4 | 30 | 30 |
| Day 5 | 30 | 60 |
| Day 6 | 60 | 60 |
| Day 7 | 60 | 60 |
| Day 8 | 60 | 60 |
| Day 9 | 60 | 120 |
| Day 10 | 120 | 120 |
| Day 11 | 120 | 120 |
| Day 12 | 120 | 120 |
| Day 13 | 120 | 120 |
| Day 14 | 120 | 120 |
| Day 15 | 120 | 120 |
| Day 16 | 120 | 180 |
| Day 17 | 180 | 180 |

In some embodiments, hepatically impaired patients with a Child-Pugh score of A are administered an Equivalent Amount of Nalbuphine Free Base according to the following titration schedule:

| Day | AM dosage (mg) | PM dosage (mg) |
| --- | --- | --- |
| Day 1 | 0 | 28 |
| Day 2 | 0 | 28 |
| Day 3 | 28 | 28 |
| Day 4 | 28 | 28 |
| Day 5 | 28 | 54 |
| Day 6 | 54 | 54 |
| Day 7 | 54 | 54 |
| Day 8 | 54 | 54 |
| Day 9 | 54 | 108 |
| Day 10 | 108 | 108 |
| Day 11 | 108 | 108 |
| Day 12 | 108 | 108 |
| Day 13 | 108 | 108 |
| Day 14 | 108 | 108 |
| Day 15 | 108 | 108 |
| Day 16 | 108 | 162 |
| Day 17 | 162 | 162. |

In various embodiments, the present disclosure provides for administering a lower dose of nalbuphine to a patient with a Child-Pugh score of B or C (i.e., a patient with moderate or severe hepatic impairment), in need of treatment for a nalbuphine-treatable disorder, compared to an otherwise physiologically identical patient with a Child-Pugh score of A (i.e., a patient with mild hepatic impairment). According to these embodiments, the lower dose is administered to Child Pugh B and C patients because, as shown in Example 2, these patients on average achieve a higher nalbuphine exposure (as determined by $C_{max}$, $AUC_{0-t}$, and $AUC_{0-inf}$) compared to a Child Pugh A patient administered the same nalbuphine dose. For example, in the Child Pugh A patients (mild hepatic impairment) in Cohort 4 (162 mg, Single Dose), mean $C_{max}$=19.9 ng/mL and mean $AUC_{0-t}$=375.27 h*ng/mL (Table 5A), whereas for Child Pugh B patients (moderate hepatic impairment) in Cohort 4, mean $C_{max}$=65.4 ng/mL and mean $AUC_{0-t}$=1233.95 h*ng/mL (Table 5B). For example, in the Child Pugh A patients (mild hepatic impairment) in Cohort 1 (27 mg, Single Dose), mean $C_{max}$=3.56 ng/mL and mean $AUC_{0-t}$=48.89 h*ng/mL (Table 2A), whereas for Child Pugh B patients (moderate hepatic impairment) in Cohort 1, mean $C_{max}$=14.6 ng/mL and mean $AUC_{0-t}$=244.03 h*ng/mL (Table 2B), whereas for Child Pugh C patients (Severe hepatic impairment) in Cohort 1, mean $C_{max}$=28.3 ng/mL and mean $AUC_{0-t}$=489.19 h*ng/mL (Table 2C).

In some embodiments, methods for treating a nalbuphine-treatable disorder in a patient with a Child-Pugh score of B or C comprises administering a daily dose from about 3 mg to about 108 mg of an Equivalent Amount of Nalbuphine Free Base. In some embodiments, about 6 mg of the Equivalent Amount of Nalbuphine Free Base is administered once a day. In some embodiments, about 9 mg of the Equivalent Amount of Nalbuphine Free Base is administered once a day. In some embodiments, about 14 mg of the Equivalent Amount of Nalbuphine Free Base is administered once a day. In some embodiments, about 18 mg of the Equivalent Amount of Nalbuphine Free Base is administered once a day. In some embodiments, about 28 mg of the Equivalent Amount of Nalbuphine Free Base is administered once a day. In some embodiments, about 36 mg of the Equivalent Amount of Nalbuphine Free Base is administered once a day. In some embodiments, about 54 mg of the Equivalent Amount of Nalbuphine Free Base is administered once a day. In some embodiments, about 6 mg of the Equivalent Amount of Nalbuphine Free Base is administered twice a day. In some embodiments, about 9 mg of the Equivalent Amount of Nalbuphine Free Base is administered twice a day. In some embodiments, about 14 mg of the Equivalent Amount of Nalbuphine Free Base is administered twice a day. In some embodiments, about 18 mg of the Equivalent Amount of Nalbuphine Free Base is administered twice a day. In some embodiments, about 28 mg of the Equivalent Amount of Nalbuphine Free Base is administered twice a day. In some embodiments, about 36 mg of the Equivalent Amount of Nalbuphine Free Base is administered twice a day. In some embodiments, about 54 mg of the Equivalent Amount of Nalbuphine Free Base is administered twice a day.

In some embodiments, methods for treating a nalbuphine-treatable disorder in a patient with a Child-Pugh score of B (i.e. a patient with moderate hepatic impairment) comprises administering a daily dose from about 3 mg to about 108 mg of an Equivalent Amount of Nalbuphine Free Base. In some embodiments, about 6 mg of the Equivalent Amount of Nalbuphine Free Base is administered once a day. In some embodiments, about 9 mg of the Equivalent Amount of Nalbuphine Free Base is administered once a day. In some embodiments, about 14 mg of the Equivalent Amount of Nalbuphine Free Base is administered once a day. In some embodiments, about 18 mg of the Equivalent Amount of Nalbuphine Free Base is administered once a day. In some embodiments, about 28 mg of the Equivalent Amount of Nalbuphine Free Base is administered once a day. In some embodiments, about 36 mg of the Equivalent Amount of Nalbuphine Free Base is administered once a day. In some embodiments, about 54 mg of the Equivalent Amount of Nalbuphine Free Base is administered once a day. In some embodiments, about 6 mg of the Equivalent Amount of Nalbuphine Free Base is administered twice a day. In some embodiments, about 9 mg of the Equivalent Amount of Nalbuphine Free Base is administered twice a day. In some embodiments, about 14 mg of the Equivalent Amount of Nalbuphine Free Base is administered twice a day. In some embodiments, about 18 mg of the Equivalent Amount of Nalbuphine Free Base is administered twice a day. In some embodiments, about 28 mg of the Equivalent Amount of Nalbuphine Free Base is administered twice a day. In some embodiments, about 36 mg of the Equivalent Amount of Nalbuphine Free Base is administered twice a day. In some embodiments, about 54 mg of the Equivalent Amount of Nalbuphine Free Base is administered twice a day.

In some embodiments, methods for treating a nalbuphine-treatable disorder in a patient with a Child-Pugh score of C (i.e. a patient with severe hepatic impairment) comprises administering a daily dose from about 2 mg to about 108 mg, or from about 3 mg to about 108 mg of an Equivalent Amount of Nalbuphine Free Base. In some embodiments, about 6 mg of the Equivalent Amount of Nalbuphine Free Base is administered once a day. In some embodiments, about 9 mg of the Equivalent Amount of Nalbuphine Free Base is administered once a day. In some embodiments, about 14 mg of the Equivalent Amount of Nalbuphine Free Base is administered once a day. In some embodiments, about 18 mg of the Equivalent Amount of Nalbuphine Free Base is administered once a day. In some embodiments, about 28 mg of the Equivalent Amount of Nalbuphine Free Base is administered once a day. In some embodiments, about 36 mg of the Equivalent Amount of Nalbuphine Free Base is administered once a day. In some embodiments, about 54 mg of the Equivalent Amount of Nalbuphine Free Base is administered once a day. In some embodiments, about 6 mg of the Equivalent Amount of Nalbuphine Free Base is administered twice a day. In some embodiments, about 9 mg of the Equivalent Amount of Nalbuphine Free Base is administered twice a day. In some embodiments, about 14 mg of the Equivalent Amount of Nalbuphine Free Base is administered twice a day. In some embodiments, about 18 mg of the Equivalent Amount of Nalbuphine Free Base is administered twice a day. In some embodiments, about 28 mg of the Equivalent Amount of Nalbuphine Free Base is administered twice a day. In some embodiments, about 36 mg of the Equivalent Amount of Nalbuphine Free Base is administered twice a day. In some embodiments, about 54 mg of the Equivalent Amount of Nalbuphine Free Base is administered twice a day.

In some embodiments, methods for treating a nalbuphine-treatable disorder in a patient with a Child-Pugh score of C comprises administering a daily dose from about 2 mg to about 54 mg of an Equivalent Amount of Nalbuphine Free Base. In some embodiments, the daily dose is from about 2 mg to about 41 of an Equivalent Amount of Nalbuphine Free Base. In some embodiments, from about 2 mg to about 7 mg of the Equivalent Amount of Nalbuphine Free Base is administered once a day. In some embodiments, from about 5 mg to about 10 mg of the Equivalent Amount of Nalbuphine Free Base is administered once a day. In some embodiments, about 6 mg of the Equivalent Amount of Nalbuphine Free Base is administered once a day. In some embodiments, about 7 mg of the Equivalent Amount of Nalbuphine Free Base is administered once a day. In some embodiments, from about 9 mg to about 14 mg of the Equivalent Amount of Nalbuphine Free Base is administered once a day. In some embodiments, from about 10 mg to about 15 mg of the Equivalent Amount of Nalbuphine Free Base is administered once a day. In some embodiments, about 9 mg of the Equivalent Amount of Nalbuphine Free Base is administered once a day. In some embodiments, about 14 mg of the Equivalent Amount of Nalbuphine Free Base is administered once a day. In some embodiments, from about 18 mg to about 21 mg of the Equivalent Amount of Nalbuphine Free Base is administered once a day. In some embodiments, from about 18 mg to about 27 mg of the Equivalent Amount of Nalbuphine Free Base is administered once a day. In some embodiments, from about 20 mg to about 27 mg of the Equivalent Amount of Nalbuphine Free Base is administered once a day. In some embodiments, from about 22 mg to about 27 mg of the Equivalent Amount of Nalbuphine Free Base is administered once a day. In some embodiments, about 18 mg of the Equivalent Amount of Nalbuphine Free Base is administered once a day. In some embodiments, about 27 mg of the Equivalent Amount of Nalbuphine Free Base is administered once a day. In some embodiments, about 36 mg of the Equivalent Amount of Nalbuphine Free Base is administered once a day. In some embodiments, about 54 mg of the Equivalent Amount of Nalbuphine Free Base is administered once a day. In some embodiments, from about 2 mg to about 7 mg of the Equivalent Amount of Nalbuphine Free Base is administered twice a day. In some embodiments, from about 5 mg to about 10 mg of the Equivalent Amount of Nalbuphine Free Base is administered twice a day. In some embodiments, about 6 mg of the Equivalent Amount of Nalbuphine Free Base is administered twice a day. In some embodiments, about 7 mg of the Equivalent Amount of Nalbuphine Free Base is administered twice a day. In some embodiments, from about 9 mg to about 14 mg of the Equivalent Amount of Nalbuphine Free Base is administered twice a day. In some embodiments, from about 10 mg to about 15 mg of the Equivalent Amount of Nalbuphine Free Base is administered twice a day. In some embodiments, about 9 mg of the Equivalent Amount of Nalbuphine Free Base is administered twice a day. In some embodiments, about 14 mg of the Equivalent Amount of Nalbuphine Free Base is administered twice a day. In some embodiments, from about 18 mg to about 21 mg of the Equivalent Amount of Nalbuphine Free Base is administered twice a day. In some embodiments, from about 18 mg to about 27 mg of the Equivalent Amount of Nalbuphine Free Base is administered twice a day. In some embodiments, from about 20 mg to about 27 mg of the Equivalent Amount of Nalbuphine Free Base is administered twice a day. In some embodiments, from about 22 mg to about 27 mg of the Equivalent Amount of Nalbuphine Free Base is administered twice a day. In some embodiments, about 18 mg of the Equivalent Amount of Nalbuphine Free Base is administered twice a day. In some embodiments, about 27 mg of the Equivalent Amount of Nalbuphine Free Base is administered twice a day.

In some embodiments, methods for treating a nalbuphine-treatable disorder in a patient with a Child-Pugh score of B or C comprises administering a daily dose from about 4 mg to about 120 mg of the nalbuphine, or a pharmaceutically acceptable salt thereof. In some embodiments, about 4 mg of the Nalbuphine, or a pharmaceutically acceptable salt thereof, is administered once a day. In some embodiments, about 7 mg of the Nalbuphine, or a pharmaceutically acceptable salt thereof, is administered once a day. In some embodiments, about 10 mg of the Nalbuphine, or a pharmaceutically acceptable salt thereof, is administered once a day. In some embodiments, about 15 mg of the Nalbuphine, or a pharmaceutically acceptable salt thereof, is administered once a day. In some embodiments, about 20 mg of the Nalbuphine, or a pharmaceutically acceptable salt thereof, is administered once a day. In some embodiments, about 31 mg of the Nalbuphine, or a pharmaceutically acceptable salt thereof, is administered once a day. In some embodiments, about 40 mg of the Nalbuphine, or a pharmaceutically acceptable salt thereof, is administered once a day. In some embodiments, about 60 mg of the Nalbuphine, or a pharmaceutically acceptable salt thereof, is administered once a day. In some embodiments, about 7 mg of the Nalbuphine, or a pharmaceutically acceptable salt thereof, is administered twice a day. In some embodiments, about 10 mg of the Nalbuphine, or a pharmaceutically acceptable salt thereof, is administered twice a day. In some embodiments, about 15 mg of the Nalbuphine, or a pharmaceutically acceptable salt thereof, is administered twice a day. In some embodiments, about 20 mg of the Nalbuphine, or a pharmaceutically acceptable salt thereof, is administered twice a day. In some embodiments, about 31 mg of the Nalbuphine, or a pharmaceutically acceptable salt thereof, is administered twice a day. In some embodiments, about 40 mg of the Nalbuphine, or a pharmaceutically acceptable salt thereof, is administered twice a day. In some embodiments, about 60 mg of the Nalbuphine, or a pharmaceutically acceptable salt thereof, is administered twice a day. In some embodiments, the dosing scheme in moderately impaired hepatic subjects (Child Pugh B) is in the NAL ER 4-5 mg-14 mg range at the lower end to NAL ER 41-54 mg range at the upper end of dosing scheme. In some embodiments, the dosing scheme in subjects with severe hepatic impairment (Child Pugh C) is in the NAL ER 3-5 mg-14 mg range at the lower end to NAL ER 41-54 mg range at the upper end of dosing scheme.

In some embodiments, methods for treating a nalbuphine-treatable disorder in a patient with a Child-Pugh score of B (i.e. a patient with moderate hepatic impairment) comprises administering a daily dose from about 4 mg to about 120 mg of the nalbuphine, or a pharmaceutically acceptable salt thereof. In some embodiments, about 4 mg of the Nalbuphine, or a pharmaceutically acceptable salt thereof, is administered once a day. In some embodiments, about 7 mg of the Nalbuphine, or a pharmaceutically acceptable salt thereof, is administered once a day. In some embodiments, about 10 mg of the Nalbuphine, or a pharmaceutically acceptable salt thereof, is administered once a day. In some embodiments, about 15 mg of the Nalbuphine, or a pharmaceutically acceptable salt thereof, is administered once a day. In some embodiments, about 20 mg of the Nalbuphine, or a pharmaceutically acceptable salt thereof, is administered once a day. In some embodiments, about 31 mg of the Nalbuphine, or a pharmaceutically acceptable salt thereof, is administered once a day. In some embodiments, about 40 mg of the Nalbuphine, or a pharmaceutically acceptable salt thereof, is administered once a day. In some embodiments, about 60 mg of the Nalbuphine, or a pharmaceutically acceptable salt thereof, is administered once a day. In some embodiments, about 7 mg of the Nalbuphine, or a pharmaceutically acceptable salt thereof, is administered twice a day. In some embodiments, wherein about 10 mg of the Nalbuphine, or a pharmaceutically acceptable salt thereof, is administered twice a day. In some embodiments, about 15 mg of the Nalbuphine, or a pharmaceutically acceptable salt thereof, is administered twice a day. In some embodiments, about 20 mg of the Nalbuphine, or a pharmaceutically acceptable salt thereof, is administered twice a day. In some embodiments, about 31 mg of the Nalbuphine, or a pharmaceutically acceptable salt thereof, is administered twice a day. In some embodiments, about 40 mg of the Nalbuphine, or a pharmaceutically acceptable salt thereof, is administered twice a day. In some embodiments, about 60 mg of the Nalbuphine, or a pharmaceutically acceptable salt thereof, is administered twice a day.

In some embodiments, methods for treating a nalbuphine-treatable disorder in a patient with a Child-Pugh score of C (i.e. a patient with severe hepatic impairment) comprises administering a daily dose from about 4 mg to about 120 mg of the nalbuphine, or a pharmaceutically acceptable salt thereof. In some embodiments, about 4 mg of the Nalbuphine, or a pharmaceutically acceptable salt thereof, is administered once a day. In some embodiments, about 7 mg of the Nalbuphine, or a pharmaceutically acceptable salt thereof, is administered once a day. In some embodiments, about 10 mg of the Nalbuphine, or a pharmaceutically acceptable salt thereof, is administered once a day. In some embodiments, about 15 mg of the Nalbuphine, or a pharmaceutically acceptable salt thereof, is administered once a day. In some embodiments, about 20 mg of the Nalbuphine, or a pharmaceutically acceptable salt thereof, is administered once a day. In some embodiments, about 31 mg of the Nalbuphine, or a pharmaceutically acceptable salt thereof, is administered once a day. In some embodiments, about 40 mg of the Nalbuphine, or a pharmaceutically acceptable salt thereof, is administered once a day. In some embodiments, about 60 mg of the Nalbuphine, or a pharmaceutically acceptable salt thereof, is administered once a day. In some embodiments, about 7 mg of the Nalbuphine, or a pharmaceutically acceptable salt thereof, is administered twice a day. In some embodiments, wherein about 10 mg of the Nalbuphine, or a pharmaceutically acceptable salt thereof, is administered twice a day. In some embodiments, about 15 mg of the Nalbuphine, or a pharmaceutically acceptable salt thereof, is administered twice a day. In some embodiments, about 20 mg of the Nalbuphine, or a pharmaceutically acceptable salt thereof, is administered twice a day In some embodiments, about 31 mg of the Nalbuphine, or a pharmaceutically acceptable salt thereof, is administered twice a day. In some embodiments, about 40 mg of the Nalbuphine, or a pharmaceutically acceptable salt thereof, is administered twice a day. In some embodiments, about 60 mg of the Nalbuphine, or a pharmaceutically acceptable salt thereof, is administered twice a day.

In some embodiments, methods for treating a nalbuphine-treatable disorder in a patient with a Child-Pugh score of C (i.e. a patient with severe hepatic impairment) comprises administering a daily dose from about 2 mg to about 54 mg of the nalbuphine, or a pharmaceutically acceptable salt thereof. In some embodiments, the daily dose is from about 2 mg to about 45 mg of the nalbuphine, or a pharmaceutically acceptable salt thereof. In some embodiments, about 2 mg of the Nalbuphine, or a pharmaceutically acceptable salt thereof, is administered once a day. In some embodiments, about 4-7 mg of the Nalbuphine, or a pharmaceutically acceptable salt thereof, is administered once a day. In some embodiments, about 4 mg of the Nalbuphine, or a pharmaceutically acceptable salt thereof, is administered once a day. In some embodiments, about 5-8 mg of the Nalbuphine, or a pharmaceutically acceptable salt thereof, is administered once a day. In some embodiments, about 5 mg of the Nalbuphine, or a pharmaceutically acceptable salt thereof, is administered once a day. In some embodiments, about 7 mg of the Nalbuphine, or a pharmaceutically acceptable salt thereof, is administered once a day. In some embodiments, about 9-14 mg of the Nalbuphine, or a pharmaceutically acceptable salt thereof, is administered once a day. In some embodiments, about 10-15 mg of the Nalbuphine, or a pharmaceutically acceptable salt thereof, is administered once a day. In some embodiments, about 10 mg of the Nalbuphine, or a pharmaceutically acceptable salt thereof, is administered once a day. In some embodiments, about 15 mg of the Nalbuphine, or a pharmaceutically acceptable salt thereof, is administered once a day. In some embodiments, about 18-27 mg of the Nalbuphine, or a pharmaceutically acceptable salt thereof, is administered once a day. In some embodiments, about 20-27 mg of the Nalbuphine, or a pharmaceutically acceptable salt thereof, is administered once a day. In some embodiments, about 22-27 mg of the Nalbuphine, or a pharmaceutically acceptable salt thereof, is administered once a day. In some embodiments, about 22-30 mg of the Nalbuphine, or a pharmaceutically acceptable salt thereof, is administered once a day. In some embodiments, about 20 mg of the Nalbuphine, or a pharmaceutically acceptable salt thereof, is administered once a day. In some embodiments, about 30 mg of the Nalbuphine, or a pharmaceutically acceptable salt thereof, is administered once a day. In some embodiments, about 40 mg of the Nalbuphine, or a pharmaceutically acceptable salt thereof, is administered once a day. In some embodiments, about 2 mg of the Nalbuphine, or a pharmaceutically acceptable salt thereof, is administered twice a day. In some embodiments, about 4-7 mg of the Nalbuphine, or a pharmaceutically acceptable salt thereof, is administered twice a day. In some embodiments, about 4 mg of the Nalbuphine, or a pharmaceutically acceptable salt thereof, is administered twice a day. In some embodiments, about 5-8 mg of the Nalbuphine, or a pharmaceutically acceptable salt thereof, is administered twice a day. In some embodiments, about 5 mg of the Nalbuphine, or a pharmaceutically acceptable salt thereof, is administered twice a day. In some embodiments, about 7 mg of the Nalbuphine, or a pharmaceutically acceptable salt thereof, is administered twice a day. In some embodiments, about 9-14 mg of the Nalbuphine, or a pharmaceutically acceptable salt thereof, is administered twice a day. In some embodiments, about 10-15 mg of the Nalbuphine, or a pharmaceutically acceptable salt thereof, is administered twice a day. In some embodiments, wherein about 10 mg of the Nalbuphine, or a pharmaceutically acceptable salt thereof, is administered twice a day. In some embodiments, about 15 mg of the Nalbuphine, or a pharmaceutically acceptable salt thereof, is administered twice a day. In some embodiments, about 18-27 mg of the Nalbuphine, or a pharmaceutically acceptable salt thereof, is administered twice a day. In some embodiments, about 20-27 mg of the Nalbuphine, or a pharmaceutically acceptable salt thereof, is administered twice a day. In some embodiments, about 22-27 mg of the Nalbuphine, or a pharmaceutically acceptable salt thereof, is administered twice a day. In some embodiments, about 22-30 mg of the Nalbuphine, or a pharmaceutically acceptable salt thereof, is administered twice a day. In some embodiments, about 20 mg of the Nalbuphine, or a pharmaceutically acceptable salt thereof, is administered twice a day. In some embodiments, about 30 mg of the Nalbuphine, or a pharmaceutically acceptable salt thereof, is administered twice a day. In some embodiments, the daily dose is from about 41-54 mg of the Nalbuphine, or a pharmaceutically acceptable salt thereof at the upper end of dosing scheme.

In some embodiments, hepatically impaired patients with a Child-Pugh score of B or C, and in particular embodiments a Child-Pugh score of B, are administered nalbuphine, or a pharmaceutically acceptable salt thereof according to the following titration schedule:

| Day | AM dosage (mg) | PM dosage (mg) |
| --- | --- | --- |
| Day 1 | 0 | 10-15 |
| Day 2 | 0 | 10-15 |
| Day 3 | 0 | 10-15 |
| Day 4 | 10-15 | 10-15 |
| Day 5 | 10-15 | 10-15 |
| Day 6 | 10-15 | 20-31 |
| Day 7 | 20-31 | 20-31 |
| Day 8 | 20-31 | 20-31 |
| Day 9 | 20-31 | 20-31 |
| Day 10 | 20-31 | 40-60 |
| Day 11 | 60 | 60 |

In some embodiments, hepatically impaired patients with a Child-Pugh score of B or C, and in particular embodiments a Child-Pugh score of B, are administered an Equivalent Amount of Nalbuphine Free Base according to the following titration schedule:

| Day    | AM dosage (mg) | PM dosage (mg) |
|--------|----------------|----------------|
| Day 1  | 0              | 9-14           |
| Day 2  | 0              | 9-14           |
| Day 3  | 0              | 9-14           |
| Day 4  | 9-14           | 9-14           |
| Day 5  | 9-14           | 9-14           |
| Day 6  | 9-14           | 18-28          |
| Day 7  | 18-28          | 18-28          |
| Day 8  | 18-28          | 18-28          |
| Day 9  | 18-28          | 18-28          |
| Day 10 | 18-28          | 36-54          |
| Day 11 | 54             | 54             |

In some embodiments, hepatically impaired patients with a Child-Pugh score of B or C, and in particular embodiments a Child-Pugh score of B, are administered an Equivalent Amount of Nalbuphine Free Base for eleven days according to the dose schedule provided in the following table:

| Day    | AM dosage (mg) | PM dosage (mg) |
|--------|----------------|----------------|
| Day 1  | 0              | 9              |
| Day 2  | 0              | 9              |
| Day 3  | 0              | 9              |
| Day 4  | 9              | 9              |
| Day 5  | 9              | 9              |
| Day 6  | 9              | 18             |
| Day 7  | 18             | 18             |
| Day 8  | 18             | 18             |
| Day 9  | 18             | 18             |
| Day 10 | 18             | 36             |
| Day 11 | 54             | 54             |

In some embodiments, hepatically impaired patients with a Child-Pugh score of B or C, and in particular embodiments a Child-Pugh score of B, are administered nalbuphine, or a pharmaceutically acceptable salt thereof for eleven days according to the dose schedule provided in the following table:

| Day    | AM dosage (mg) | PM dosage (mg) |
|--------|----------------|----------------|
| Day 1  | 0              | 10             |
| Day 2  | 0              | 10             |
| Day 3  | 0              | 10             |
| Day 4  | 10             | 10             |
| Day 5  | 10             | 10             |
| Day 6  | 10             | 20             |
| Day 7  | 20             | 20             |
| Day 8  | 20             | 20             |
| Day 9  | 20             | 20             |
| Day 10 | 20             | 40             |
| Day 11 | 60             | 60             |

In some embodiments, hepatically impaired patients with a Child-Pugh score of B or C, and in particular embodiments a Child-Pugh score of B, are administered an Equivalent Amount of Nalbuphine Free Base according to the following titration schedule:

| Day    | AM dosage (mg) | PM dosage (mg) |
|--------|----------------|----------------|
| Day 1  | 0              | 14             |
| Day 2  | 0              | 14             |
| Day 3  | 0              | 14             |
| Day 4  | 14             | 14             |
| Day 5  | 14             | 14             |
| Day 6  | 14             | 28             |
| Day 7  | 28             | 28             |
| Day 8  | 28             | 28             |
| Day 9  | 28             | 28             |
| Day 10 | 28             | 54             |
| Day 11 | 54             | 54             |

In some embodiments, hepatically impaired patients with a Child-Pugh score of B or C, and in particular embodiments a Child-Pugh score of B, are administered nalbuphine, or a pharmaceutically acceptable salt thereof according to the following titration schedule:

| Day    | AM dosage (mg) | PM dosage (mg) |
|--------|----------------|----------------|
| Day 1  | 0              | 15             |
| Day 2  | 0              | 15             |
| Day 3  | 0              | 15             |
| Day 4  | 15             | 15             |
| Day 5  | 15             | 15             |
| Day 6  | 15             | 31             |
| Day 7  | 31             | 31             |
| Day 8  | 31             | 31             |
| Day 9  | 31             | 31             |
| Day 10 | 31             | 60             |
| Day 11 | 60             | 60             |

In some embodiments, hepatically impaired patients with a Child-Pugh score of B or C, and in particular embodiments a Child-Pugh score of B, are administered an Equivalent Amount of Nalbuphine Free Base according to the following titration schedule:

| Day   | AM dosage (mg) | PM dosage (mg) |
|-------|----------------|----------------|
| Day 1 | 0              | 9-14           |
| Day 2 | 9-14           | 9-14           |
| Day 3 | 9-14           | 9-14           |
| Day 4 | 9-14           | 18-28          |
| Day 5 | 18-28          | 18-28          |
| Day 6 | 18-28          | 18-28          |
| Day 7 | 18-28          | 36-54          |
| Day 8 | 54             | 54             |

In some embodiments, hepatically impaired patients with a Child-Pugh score of B or C, and in particular embodiments a Child-Pugh score of B, are administered nalbuphine, or a pharmaceutically acceptable salt thereof according to the following titration schedule:

| Day   | AM dosage (mg) | PM dosage (mg) |
|-------|----------------|----------------|
| Day 1 | 0              | 10-15          |
| Day 2 | 10-15          | 10-15          |
| Day 3 | 10-15          | 10-15          |
| Day 4 | 10-15          | 20-31          |
| Day 5 | 20-31          | 20-31          |
| Day 6 | 20-31          | 20-31          |
| Day 7 | 20-31          | 40-60          |
| Day 8 | 60             | 60             |

In some embodiments, hepatically impaired patients with a Child-Pugh score of B or C, and in particular embodiments a Child-Pugh score of B, are administered an Equivalent Amount of Nalbuphine Free Base according to the following titration schedule:

| Day | AM dosage (mg) | PM dosage (mg) |
| --- | --- | --- |
| Day 1 | 0 | 9 |
| Day 2 | 9 | 9 |
| Day 3 | 9 | 9 |
| Day 4 | 9 | 18 |
| Day 5 | 18 | 18 |
| Day 6 | 18 | 18 |
| Day 7 | 18 | 36 |
| Day 8 | 54 | 54 |

In some embodiments, hepatically impaired patients with a Child-Pugh score of B or C, and in particular embodiments a Child-Pugh score of B, are administered nalbuphine, or a pharmaceutically acceptable salt thereof according to the following titration schedule:

| Day | AM dosage (mg) | PM dosage (mg) |
| --- | --- | --- |
| Day 1 | 0 | 10 |
| Day 2 | 10 | 10 |
| Day 3 | 10 | 10 |
| Day 4 | 10 | 20 |
| Day 5 | 20 | 20 |
| Day 6 | 20 | 20 |
| Day 7 | 20 | 40 |
| Day 8 | 60 | 60 |

In some embodiments, hepatically impaired patients with a Child-Pugh score of B or C, and in particular embodiments a Child-Pugh score of B, are administered an Equivalent Amount of Nalbuphine Free Base according to the following titration schedule:

| Day | AM dosage (mg) | PM dosage (mg) |
| --- | --- | --- |
| Day 1 | 0 | 14 |
| Day 2 | 14 | 14 |
| Day 3 | 14 | 14 |
| Day 4 | 14 | 28 |
| Day 5 | 28 | 28 |
| Day 6 | 28 | 28 |
| Day 7 | 28 | 54 |
| Day 8 | 54 | 54 |

In some embodiments, hepatically impaired patients with a Child-Pugh score of B or C, and in particular embodiments a Child-Pugh score of B, are administered nalbuphine, or a pharmaceutically acceptable salt thereof according to the following titration schedule:

| Day | AM dosage (mg) | PM dosage (mg) |
| --- | --- | --- |
| Day 1 | 0 | 15 |
| Day 2 | 15 | 15 |
| Day 3 | 15 | 15 |
| Day 4 | 15 | 31 |
| Day 5 | 31 | 31 |
| Day 6 | 31 | 31 |
| Day 7 | 31 | 60 |
| Day 8 | 60 | 60 |

In some embodiments, hepatically impaired patients with a Child-Pugh score of B are administered nalbuphine, or a pharmaceutically acceptable salt thereof according to the titration schedules specified in the previous embodiments.

In some embodiments, hepatically impaired patients with a Child-Pugh score of C are administered nalbuphine, or a pharmaceutically acceptable salt thereof according to the following titration schedule:

| Day | AM dosage (mg) | PM dosage (mg) |
| --- | --- | --- |
| Day 1 | 0 | 5-8 |
| Day 2 | 0 | 5-8 |
| Day 3 | 0 | 5-8 |
| Day 4 | 5-8 | 5-8 |
| Day 5 | 5-8 | 5-8 |
| Day 6 | 5-8 | 10-15 |
| Day 7 | 10-15 | 10-15 |
| Day 8 | 10-15 | 10-15 |
| Day 9 | 10-15 | 10-15 |
| Day 10 | 10-15 | 20-27 |
| Day 11 | 20-27 | 20-27 |

In some embodiments, hepatically impaired patients with a Child-Pugh score of C are administered an Equivalent Amount of Nalbuphine Free Base according to the following titration schedule:

| Day | AM dosage (mg) | PM dosage (mg) |
| --- | --- | --- |
| Day 1 | 0 | 2-7 |
| Day 2 | 0 | 2-7 |
| Day 3 | 0 | 2-7 |
| Day 4 | 2-7 | 2-7 |
| Day 5 | 2-7 | 2-7 |
| Day 6 | 2-7 | 9-14 |
| Day 7 | 9-14 | 9-14 |
| Day 8 | 9-14 | 9-14 |
| Day 9 | 9-14 | 9-14 |
| Day 10 | 9-14 | 20-27 |
| Day 11 | 20-27 | 20-27 |

In some embodiments, hepatically impaired patients with a Child-Pugh score of C are administered nalbuphine, or a pharmaceutically acceptable salt thereof for eleven days according to the dose schedule provided in the following table:

| Day | AM dosage (mg) | PM dosage (mg) |
| --- | --- | --- |
| Day 1 | 0 | 5 |
| Day 2 | 0 | 5 |
| Day 3 | 0 | 5 |
| Day 4 | 10 | 5 |
| Day 5 | 10 | 5 |
| Day 6 | 10 | 10 |
| Day 7 | 10 | 10 |
| Day 8 | 10 | 10 |
| Day 9 | 10 | 10 |
| Day 10 | 10 | 22-27 |
| Day 11 | 22-27 | 22-27 |

In some embodiments, hepatically impaired patients with a Child-Pugh score of C are administered an Equivalent Amount of Nalbuphine Free Base according to the following titration schedule:

| Day | AM dosage (mg) | PM dosage (mg) |
| --- | --- | --- |
| Day 1 | 0 | 7 |
| Day 2 | 0 | 7 |
| Day 3 | 0 | 7 |
| Day 4 | 7 | 7 |
| Day 5 | 7 | 7 |

| Day | AM dosage (mg) | PM dosage (mg) |
| --- | --- | --- |
| Day 6 | 7 | 14 |
| Day 7 | 14 | 14 |
| Day 8 | 14 | 14 |
| Day 9 | 14 | 14 |
| Day 10 | 14 | 22-27 |
| Day 11 | 22-27 | 22-27 |

In some embodiments, hepatically impaired patients with a Child-Pugh score of C are administered nalbuphine, or a pharmaceutically acceptable salt thereof according to the following titration schedule:

| Day | AM dosage (mg) | PM dosage (mg) |
| --- | --- | --- |
| Day 1 | 0 | 7 |
| Day 2 | 0 | 7 |
| Day 3 | 0 | 7 |
| Day 4 | 7 | 7 |
| Day 5 | 7 | 7 |
| Day 6 | 7 | 15 |
| Day 7 | 15 | 15 |
| Day 8 | 15 | 15 |
| Day 9 | 15 | 15 |
| Day 10 | 15 | 22-27 |
| Day 11 | 22-27 | 22-27 |

In some embodiments, hepatically impaired patients with a Child-Pugh score of C are administered an Equivalent Amount of Nalbuphine Free Base according to the following titration schedule:

| Day | AM dosage (mg) | PM dosage (mg) |
| --- | --- | --- |
| Day 1 | 0 | 5-10 |
| Day 2 | 5-10 | 5-10 |
| Day 3 | 5-10 | 5-10 |
| Day 4 | 5-10 | 10-15 |
| Day 5 | 10-15 | 10-15 |
| Day 6 | 10-15 | 10-15 |
| Day 7 | 10-15 | 20-27 |
| Day 8 | 20-27 | 20-27 |

In some embodiments, hepatically impaired patients with a Child-Pugh score of C are administered nalbuphine, or a pharmaceutically acceptable salt thereof according to the following titration schedule:

| Day | AM dosage (mg) | PM dosage (mg) |
| --- | --- | --- |
| Day 1 | 0 | 4-7 |
| Day 2 | 4-7 | 4-7 |
| Day 3 | 4-7 | 4-7 |
| Day 4 | 4-7 | 9-14 |
| Day 5 | 9-14 | 9-14 |
| Day 6 | 9-14 | 9-14 |
| Day 7 | 9-14 | 18-27 |
| Day 8 | 18-27 | 18-27 |

In some embodiments, the dose of nalbuphine, or a pharmaceutically acceptable salt thereof is not titrated in a patient with Child-Pugh B. In some embodiments, the dose of nalbuphine, or a pharmaceutically acceptable salt thereof is not titrated in a patient with Child-Pugh C.

In some embodiments, nalbuphine, or a pharmaceutically acceptable salt thereof is not administered to a patient with a Child-Pugh Score of B. In some embodiments, nalbuphine, or a pharmaceutically acceptable salt or ester thereof is not administered to a patient a Child-Pugh Score of C.

According to the present disclosure, nalbuphine, or a pharmaceutically acceptable salt or ester thereof, is administered on a once or twice a day basis. In some embodiments, a total daily dose of about 15 mg, about 30 mg, about 60 mg, about 90 mg, about 120 mg, about 180 mg, about 240 mg, or about 360 mg.

According to the present disclosure, an Equivalent Amount of Nalbuphine Free Base is administered on a once or twice a day basis. In some embodiments, a total daily dose of about 14 mg, about 28 mg, about 54 mg, about 81 mg, about 108 mg, about 162 mg, or about 324 mg administered.

In some embodiments, the total daily dose of nalbuphine can be at least about 15 mg a day for the treatment of nalbuphine-treatable disorders in a hepatically impaired patient. In some embodiments, the total daily dose of nalbuphine can be at least about 30 mg a day for the treatment a nalbuphine-treatable disorder in a hepatically impaired patient. In some embodiments, the total daily dose of nalbuphine can be at least about 60 mg a day for the treatment of a nalbuphine-treatable disorder in a hepatically impaired patient. In some embodiments, the total daily dose of nalbuphine can be at least about 90 mg a day for the treatment of a nalbuphine-treatable disorder in a hepatically impaired patient. In some embodiments, the total daily dose of nalbuphine can be at least about 120 mg a day for the treatment of a nalbuphine-treatable disorder in a hepatically impaired patient. In some embodiments, the total daily dose of nalbuphine can be at least about 180 mg a day for the treatment of a nalbuphine-treatable disorder in a hepatically impaired patient. In some embodiments, the total daily dose of can be at least about 240 mg a day for the treatment of a nalbuphine-treatable disorder in a hepatically impaired patient. In some embodiments, the total daily dose of nalbuphine can be at least about 360 mg a day for the treatment of a nalbuphine-treatable disorder in a hepatically impaired patient. In some embodiments, the hepatically impaired patient has a Child-Pugh score of A. In some embodiments, the hepatically impaired patient has a Child-Pugh score of B. In some embodiments, the hepatically impaired patient has a Child-Pugh score of C.

In some embodiments, the total daily dose of nalbuphine can be about 15 mg a day for the treatment of a nalbuphine-treatable disorder in a hepatically impaired patient. In some embodiments, the total daily dose of nalbuphine can be about 30 mg a day for the treatment of a nalbuphine-treatable disorder in a hepatically impaired patient. In some embodiments, the total daily dose of nalbuphine can be about 60 mg a day for the treatment of a nalbuphine-treatable disorder in a hepatically impaired patient. In some embodiments, the total daily dose of nalbuphine can be about 90 mg a day for the treatment of a nalbuphine-treatable disorder in a hepatically impaired patient. In some embodiments, the total daily dose of nalbuphine can be about 120 mg a day for the treatment of a nalbuphine-treatable disorder in a hepatically impaired patient. In some embodiments, the total daily dose of nalbuphine can be about 180 mg a day for the treatment of a nalbuphine-treatable disorder in a hepatically impaired patient. In some embodiments, the total daily dose of nalbuphine can be about 240 mg a day for the treatment of a nalbuphine-treatable disorder in a hepatically impaired patient. In some embodiments, the total daily dose of nalbuphine can be about 360 mg a day for the treatment of a nalbuphine-treatable disorder in a hepatically impaired patient. In some embodiments, the hepatically impaired patient has a Child- Pugh score of A. In some embodiments, the hepatically impaired patient has a Child-Pugh score of B. In some embodiments, the hepatically impaired patient has a Child-Pugh score of C.

In some embodiments, the amount of nalbuphine administered to a patient in need thereof is in the form of a pharmaceutically acceptable salt and is expressed in terms of the Equivalent Amount of Nalbuphine Free Base provided to said patient.

In some embodiments, the total daily dose of the Equivalent Amount of Nalbuphine Free Base can be at least about 14 mg a day for the treatment of a nalbuphine-treatable disorder in a hepatically impaired patient. In some embodiments, the total daily dose of the Equivalent Amount of Nalbuphine Free Base can be at least about 27 mg a day for the treatment of a nalbuphine-treatable disorder in a hepatically impaired patient. In some embodiments, the total daily dose of the Equivalent Amount of Nalbuphine Free Base can be at least about 54 mg a day for the treatment of a nalbuphine-treatable disorder in a hepatically impaired patient. In some embodiments, the total daily dose of the Equivalent Amount of Nalbuphine Free Base can be at least about 81 mg a day for the treatment of a nalbuphine-treatable disorder in a hepatically impaired patient. In some embodiments, the total daily dose of the Equivalent Amount of Nalbuphine Free Base can be at least about 108 mg a day for the treatment of a nalbuphine-treatable disorder in a hepatically impaired patient. In some embodiments, the total daily dose of the Equivalent Amount of Nalbuphine Free Base can be at least about 162 mg a day for the treatment of a nalbuphine-treatable disorder in a hepatically impaired patient. In some embodiments, the total daily dose of the Equivalent Amount of Nalbuphine Free Base can be at least about 216 mg a day for the treatment of a nalbuphine-treatable disorder in a hepatically impaired patient. In some embodiments, the hepatically impaired patient has a Child-Pugh score of A. In some embodiments, the hepatically impaired patient has a Child-Pugh score of B. In some embodiments, the hepatically impaired patient has a Child-Pugh score of C.

In some embodiments, the total daily dose of the Equivalent Amount of Nalbuphine Free Base can be about 14 mg a day for the treatment of a nalbuphine-treatable disorder in a hepatically impaired patient. In some embodiments, the total daily dose of the Equivalent Amount of Nalbuphine Free Base can be about 27 mg a day for the treatment of a nalbuphine-treatable disorder in a hepatically impaired patient. In some embodiments, the total daily dose of the Equivalent Amount of Nalbuphine Free Base can be about 54 mg a day for the treatment of a nalbuphine-treatable disorder in a hepatically impaired patient. In some embodiments, the total daily dose of the Equivalent Amount of Nalbuphine Free Base can be about 81 mg a day for the treatment of a nalbuphine-treatable disorder in a hepatically impaired patient. In some embodiments, the total daily dose of the Equivalent Amount of Nalbuphine Free Base can be about 108 mg a day for the treatment of a nalbuphine-treatable disorder in a hepatically impaired patient. In some embodiments, the total daily dose of the Equivalent Amount of Nalbuphine Free Base can be about 162 mg a day for the treatment of a nalbuphine-treatable disorder in a hepatically impaired patient. In some embodiments, the total daily dose of the Equivalent Amount of Nalbuphine Free Base can be about 216 mg a day for the treatment of a nalbuphine-treatable disorder in a hepatically impaired patient. In some embodiments, the hepatically impaired patient has a Child-Pugh score of A. In some embodiments, the hepatically impaired patient has a Child-Pugh score of B. In some embodiments, the hepatically impaired patient has a Child-Pugh score of C.

Reduction of itch in patients with pruritic conditions can be determined by various methods. In some embodiments, the effectiveness of a dosage regimen can be determined by evaluation via a Pruritus Visual Analog Scale (VAS) test, such as the worst-itch VAS. In some embodiments, the effectiveness of a dosage regimen can be determined by evaluation via a worst or average itching intensity Numerical Rating Scale (NRS). In some embodiments, the effectiveness of a dosage regimen can be determined by evaluation via a worst or average itching intensity Numerical Rating Scale (NRS), a Patient Global index scale, a Global Physician index scale, Patient Benefit Index-pruritus version (PBI-P), itchy Verbal Rating Scale (VRS) score, ItchyQoL™ (Emory University; http://emoryott.technologypublisher.com/tech?title=ItchyQol%3a_A_Pruritus-Specific_Quality_of_Life_Instrument) or any combination thereof. In still some embodiments, the effectiveness of a dosage regimen can be determined by evaluation via a worst or average itching intensity NRS as a primary efficacy endpoint in association with secondary efficacy endpoints such as the PROMIS Sleep Disturbance Short Form 8a questionnaire, a PROMIS Item Bank v1.0 Fatigue Short Form 7a Scale, PROMIS Item Bank v1.0 PROMIS Sleep Disturbance-Short Form 8a questionnaire, a Patient-Rated Global Assessment of Treatment scale, a Physician-Rated Global Assessment of Treatment scale, Patient Benefit Index-pruritus version (PBI-P), itchy Verbal Rating Scale (VRS) score, the ItchyQoL™ scale or any combination thereof.

In some embodiments, the dosing frequency and dose amount per administration of nalbuphine, or a pharmaceutically acceptable salt thereof, are selected to provide therapeutic effects for the treatment of pruritus. In some embodiments, the dosing frequency and dose amount per administration of nalbuphine, or a pharmaceutically acceptable salt thereof are selected to provide therapeutic effects for the treatment of prurigo nodularis. In some embodiments, the dosing frequency and dose amount per administration of nalbuphine of a pharmaceutically acceptable salt thereof are selected to provide therapeutic effects for the treatment of uremic pruritus. Methods of treating prurigo nodularis and methods of treating uremic pruritus by administering nalbuphine to a patient in need thereof are described in U.S. Pat. Nos. 8,987,289; 8,637,538; 8,940,753 and 10,238,646 and U.S. Publication Nos. 2018/0125840 and 2018/0008592, the contents of which are hereby incorporated by reference in their entireties for all purposes.

According to some embodiments of the present disclosure, the dosing frequency and dose amount per administration of nalbuphine, or a pharmaceutically acceptable salt thereof, are selected to provide therapeutic effects for the treatment of cough (such chronic cough), breathlessness, or dyspnea (such as cough, breathlessness or dyspnea associated with IPF). Methods of treating cough (such chronic cough), breathlessness, or dyspnea (such as cough, breathlessness or dyspnea associated with IPF) by administering nalbuphine to a patient in need thereof are described in U.S. Publication No. 2020/0022974, the contents of which are hereby incorporated by reference in their entireties for all purposes.

According to some embodiments of the present disclosure, the dosing frequency and dose amount per administration of nalbuphine, or a pharmaceutically acceptable salt thereof, are selected to provide therapeutic effects for the treatment of dyskinesia. In some embodiments, the dosing frequency and dose amount per administration of nalbuphine, or a pharmaceutically acceptable salt thereof, are selected to provide therapeutic effects for the treatment of levodopa-induced dyskinesia (LID). In some embodiments, the dosing frequency and dose amount per administration of nalbuphine, or a pharmaceutically acceptable salt thereof, are selected to provide therapeutic effects for the treatment of tardive dyskinesia. In some embodiments, the dosing frequency and dose amount per administration of nalbuphine, or a pharmaceutically acceptable salt thereof, are selected to provide therapeutic effects for the treatment of Huntington's disease. Methods of treating dyskinesias (including LID in Parkinson's patients) by administering nalbuphine to a patient in need thereof are described in U.S. Pat. Nos. 9,289,423; 9,918,980; and 10,736,889, the contents of which are hereby incorporated by reference in their entireties for all purposes.

According to some embodiments of the present disclosure, the dosing frequency and dose amount per administration of nalbuphine, or a pharmaceutically acceptable salt thereof, are selected to provide therapeutic effects for the treatment of pruritus associated obstructive cholestasis secondary to bile duct obstruction due to non-hepatic tissue disease (for example, pruritus associated with pancreatic cancer, pancreatitis, congenital or acquired biliary strictures, lymph node obstruction such as from lymphomas or bile duct stones). Methods of treating pruritus associated with hepatic diseases or disorders by administering nalbuphine to a patient in need thereof are described in U.S. Publication No. 2020/0016150, the contents of which are hereby incorporated by reference in their entireties for all purposes.

According to some embodiments of the present disclosure, the dosing frequency and dose amount per administration of nalbuphine, or a pharmaceutically acceptable salt, solvate or ester thereof, selected to provide therapeutic effects for the treatment of pruritus associated with liver disease (for example, pruritus associated with primary sclerosing cholangitis, primary biliary cholangitis, etc.).

According to some embodiments of the present disclosure, the dosing frequency and dose amount per administration nalbuphine, or a pharmaceutically acceptable salt, solvate or ester thereof, is selected to provide therapeutic effects for the treatment of pruritus associated with liver disease selected from cholestatic liver disease, infectious hepatitis; cirrhotic liver disease, drug-induced liver disease, idiopathic portal hypertension, congenital malformations or genetic diseases affecting liver function, sarcoidosis, primary or metastatic neoplasm involvement of the liver and autoimmune hepatitis-cholangitis (Overlap syndrome).

According to some embodiments of the present disclosure, the dosing frequency and dose amount per administration of nalbuphine, or a pharmaceutically acceptable salt, solvate or ester thereof, selected to provide therapeutic effects for the treatment of pruritus associated with liver disease that is refractory to other treatments. In some embodiments, the dosing frequency and dose amount per administration of nalbuphine, or a pharmaceutically acceptable salt thereof, are selected to provide therapeutic effects for the treatment of pruritus associated with liver disease that is refractory to treatment with other anti-pruritus agents, refractory to treatment with bile sequestrants or refractory to treatment with rifampicin.

In some embodiments, nalbuphine, or a pharmaceutically acceptable salt, solvate or ester thereof, is administered on a once-a-day or twice-a-day basis for at least a week, for example, about a week, about 2 weeks, about 3 weeks, about 4 weeks, about 5 weeks, about 6 weeks, about 7 weeks, about 8 weeks, about 9 weeks, about 10 weeks, about 12 weeks, about 18 weeks, about 24 weeks, and about 50 weeks.

In some embodiments, at least about 15 mg or about 15 mg of nalbuphine, or a pharmaceutically acceptable salt, solvate or ester thereof, is administered on a once-a-day or twice-a-day basis for at least a week. In some embodiments, at least about 30 mg or about 30 mg of nalbuphine, or a pharmaceutically acceptable salt, solvate or ester thereof, is administered on a once-a-day or twice-a-day basis for at least a week. In some embodiments, at least about 60 mg or about 60 mg of nalbuphine, or a pharmaceutically acceptable salt, solvate or ester thereof, is administered on a once-a-day or twice-a-day basis for at least a week. In some embodiments, at least about 90 mg or about 90 mg of nalbuphine, or a pharmaceutically acceptable salt, solvate or ester thereof, is administered on a once-a-day or twice-a-day basis for at least a week. In some embodiments, at least about 120 mg or about 120 mg of nalbuphine, or a pharmaceutically acceptable salt, solvate or ester thereof, is administered on a once-a-day or twice-a-day basis for at least a week. In some embodiments, at least about 180 mg or about 180 mg of nalbuphine, or a pharmaceutically acceptable salt, solvate or ester thereof, is administered on a once-a-day or twice-a-day basis for at least a week. In some embodiments, at least about 240 mg or about 240 mg of nalbuphine, or a pharmaceutically acceptable salt, solvate or ester thereof, is administered on a once-a-day or twice-a-day basis for at least a week. In some embodiments, at least about 360 mg or about 360 mg of nalbuphine, or a pharmaceutically acceptable salt, solvate or ester thereof, is administered on a once-a-day or twice-a-day basis for at least a week.

According to some embodiments, the substantial reduction in itch provided by the methods of the present disclosure requires treatment for a specified time interval (e.g., at least one week) before the patient experiences substantial reduction of itch (i.e., there is an induction period before the patient experiences a substantial reduction in itch). In some embodiments, after treatment for at least one week, at least two weeks, at least three weeks, at least four weeks, at least five weeks, at least six weeks, at least seven weeks or at least eight weeks, the patient experiences a substantial reduction of itch compared to prior to the treatment. In some embodiments, after treatment for at least one week the patient experiences a substantial reduction of itch compared to prior to the treatment. According to this embodiment, the substantial reduction in itch may be expressed using any of the methods described herein (for example, decline in worst or average itching intensity Numerical Rating Scale value compared to prior to the treatment, improvement in the ItchyQoL™ scale compared to prior to the treatment, etc.).

In some embodiments, the daily dose of nalbuphine, or a pharmaceutically acceptable salt or ester thereof, is in a once or twice daily dose, and then titrated upward until the patient experiences a therapeutic effect. The daily dose can be titrated in increments ranging from about 5 mg to about 60 mg, or about 15 mg to about 60 mg (e.g., about 5 mg, about 10 mg, about 15 mg, about 30 mg or about 60 mg). The daily dose can be titrated in one or more steps. The daily dosage can be titrated by increasing a single daily dosage, or each dose of a twice-daily dosing regimen. The amount a dosage is stepped, where there are multiple titration steps, can be the same, or can be different.

In some embodiments, the titration may be initiated with about 15 mg, about 30 mg or about 60 mg of nalbuphine, or a pharmaceutically acceptable salt or ester thereof, once or twice daily. In some embodiments, doses can be adjusted in 30 mg increments every 1 to 4 days. Hepatically impaired patients can self-titrate to effect over from about 7 days to about 30 days (for example, from about 12 days to about 20 days) to a dose that provides adequate relief from itch and minimizes adverse reactions. In some embodiments, the titration is conducted for at least about one week, about 2 weeks, about 3 weeks, about 4 weeks or about 5 weeks until a steady state is achieved in the patient.

In some embodiments, the titration may be initiated with from about 1 mg to about 10 mg of nalbuphine, or a pharmaceutically acceptable salt or ester thereof, once or twice daily including, from about 1 mg, about 2 mg, about 3 mg, about 4 mg, about 5 mg, about 6 mg, about 7 mg, about 8 mg, about 9 mg, to about 10 mg including all ranges and values therebetween of nalbuphine, or a pharmaceutically acceptable salt or ester thereof, once or twice daily. In some embodiments, the dose can be adjusted in from about 2 mg to about 10 mg increments, including form about 2 mg increments, about 3 mg increments, about 4 mg increments, about 5 mg increments, about 6 mg increments, 7 mg increments, about 8 mg increments, about 9 mg increments, to about 10 mg increments, including all ranges and values therebetween. In some embodiments, the dose is adjusted every 1-4 days (for example, every day, every 2 days, every 3 days, or every 4 days). In some embodiments, the dose is adjusted every 3-4 days. In some embodiments, hepatically impaired patients can self-titrate to effect over from about 5 days to about 30 days (for example, from about 5 days to about 12 days) to a dose that provides adequate relief from itch and minimizes adverse reactions. In some embodiments, the titration is conducted for about or at least about 4 to 14 days (for example about or at least about 4 days, 5 days, 6 days, 7 days, 8 days, 9 days, 10 days, 11 days, 12 days, 13 days, or 14 days). In some embodiments, a hepatically impaired patient can self-titrate up to from about 9 to about 54 mg of nalbuphine, or a pharmaceutically acceptable salt or ester thereof once or twice daily, including from about 9 mg, about 10 mg, about 15 mg, about 20 mg, about 25 mg, about 30 mg, about 35 mg, about 40 mg, about 45, about 50 mg to about 54 mg including all ranges and values therebetween of nalbuphine, or a pharmaceutically acceptable salt or ester thereof once or twice daily. In some embodiments, a hepatically impaired patient can be provided with initially about 1-10 mg of nalbuphine, or a pharmaceutically acceptable salt or ester thereof once or twice daily, and titrate up to from about 20-27 mg once or twice daily. In some embodiments, the hepatically impaired patient has a Child-Pugh score of B. In some embodiments, the hepatically impaired patient has a Child-Pugh score of C.

In some embodiments, a hepatically impaired patient can be provided initially with 15 mg, 30 mg or 60 mg tablets to self-titrate to effect up to about 60 mg, about 90 mg, about 120 mg, about 180 mg, about 240 mg, about 360 mg, or about 480 mg once or twice a day. In some embodiments, the titration dose is started with about 15 mg or about 30 mg, and then gradually increased to about 60 mg or 120 mg twice a day, e.g., for a hepatically impaired patient with a nalbuphine-treatable disorder. In some embodiments, the titration dose is started with about 15 mg or about 30 mg, and then gradually increased to about 60 mg or 120 mg once a day, e.g., for a hepatically impaired patient with a nalbuphine-treatable disorder. In some embodiments, the titration dose is started with about 15 mg or about 30 mg, and then gradually increased to about 120 mg or 240 mg twice a day, e.g., for a hepatically impaired patient with a nalbuphine-treatable disorder. In some embodiments, the titration dose is started with about 15 mg or about 30 mg, and then gradually increased to about 120 mg or 240 mg once a day, e.g., for a hepatically impaired patient with a nalbuphine-treatable disorder. In some embodiments, the hepatically impaired patient has a Child-Pugh score of A. In some embodiments, the hepatically impaired patient has a Child-Pugh score of B. In some embodiments, the hepatically impaired patient has a Child-Pugh score of C.

According to some embodiments of the present disclosure, the methods of the present disclosure provide therapeutically effective blood plasma levels of nalbuphine for treating a hepatically impaired patient with a nalbuphine-treatable disorder. Blood plasma levels of nalbuphine may be expressed using pharmacokinetic parameters that are known to those skilled in the art, such as steady state plasma levels, AUC, $C_{max}$ and $C_{min}$. Blood plasma levels of nalbuphine are described in U.S. Publication Nos. 2014/0171459, 2014/0350042, 2015/0359789, and 2017/0216277, which are incorporated by reference herein in their entirety.

In some embodiments, the present methods provide steady state plasma levels of nalbuphine that correlate to one or more statistically significant therapeutic effects. In some embodiments, the therapeutically effective steady state plasma levels of nalbuphine provided by the methods of the present disclosure range from about 10 ng/mL to about 80 ng/mL, including about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL and about 80 ng/mL, including all ranges there between. In some embodiments, the steady state plasma levels of nalbuphine provided by the methods of the present disclosure range from about 20 and 80 ng/mL. In some embodiments, the steady state plasma levels of nalbuphine provided by the methods of the present disclosure range from about 30 and 70 ng/mL. In some embodiments, the therapeutically effective steady state plasma levels of nalbuphine is provided by administering a daily dose of nalbuphine, or a pharmaceutically acceptable salt or ester thereof, is about 360 mg. In further embodiments, the therapeutically effective steady state plasma levels of nalbuphine is provided by administering about 180 mg of nalbuphine, or a pharmaceutically acceptable salt or ester thereof, twice a day.

In some embodiments, the present methods provide a mean Cmax of from about 1 ng/mL to about 90 ng/mL, from about 5 ng/mL to about 85 ng/mL, from about 5 ng/mL to about 45 ng/mL, from about 25 ng/mL to about 72 ng/mL, or from about 13 ng/mL to about 28 ng/mL. In some embodiments, the present methods provide a mean $C_{max}$ of from about 5 ng/mL to about 45 ng/mL. In some embodiments, the present methods provide a mean $C_{max}$ of from about 1 ng/mL to about 70 ng/mL. In some embodiments, the present methods provide a mean $C_{max}$ of from about 24 ng/mL to about 71 ng/mL. In some embodiments, the present methods provide a mean $C_{max}$ from about 24.78 ng/mL to about 70.33 ng/mL. In some embodiments, the present methods provide a mean $C_{max}$ of from about 6.28 ng/mL to about 82.78 ng/mL.

In some embodiments, the present methods provide mean steady state $AUC_{0-24h}$ (expressed in terms of ng*hr/mL) levels of nalbuphine that correlate to one or more statistically significant therapeutic effects. In some embodiments, the therapeutically effective mean steady state $AUC_{0-24h}$ levels of nalbuphine provided by the methods of the present disclosure range from about 200 ng*hr/mL to about 1600 ng*hr/mL, including about 300 ng*hr/mL, about 400 ng*hr/ mL, about 500 ng*hr/mL, about 600 ng*hr/mL, about 700 ng*hr/mL, about 800 ng*hr/mL, about 900 ng*hr/mL, about 1000 ng*hr/mL, about 1100 ng*hr/mL, about 1200 ng*hr/mL, about 1300 ng*hr/mL, about 1400 ng*hr/mL, and about 1500 ng*hr/mL, including all ranges there between. In some embodiments, the therapeutically effective mean steady state $AUC_{0-24h}$ levels of nalbuphine is provided by administering a daily dose of nalbuphine, or a pharmaceutically acceptable salt or ester thereof, is about 360 mg. In further embodiments, the therapeutically effective mean steady state $AUC_{0-24h}$ levels of nalbuphine is provided by administering about 180 mg of nalbuphine, or a pharmaceutically acceptable salt or ester thereof, twice a day.

In some embodiments, the present methods provide a mean $AUC_{0-24h}$ from about 40 ng·hr/mL to about 1600 ng·hr/mL. In some embodiments, the present methods provide a mean $AUC_{0-24h}$ from about 80 ng·hr/mL to about 1600 ng·hr/mL. In some embodiments, the present methods provide a mean $AUC_{0-24h}$ from about 80 ng·hr/mL to about 400 ng·hr/mL. In some embodiments, the present methods provide a mean $AUC_{0-24h}$ from about 360 ng·hr/mL to about 620 ng·hr/mL. In some embodiments, the present methods provide a mean $AUC_{0-24h}$ from about 200 ng·hr/mL to about 800 ng·hr/mL. In some embodiments, the present methods provide a mean $AUC_{0-24h}$ from about 400 ng·hr/mL to about 1000 ng·hr/mL. In some embodiments, the present methods provide a mean $AUC_{0-24h}$ from about 600 ng·hr/mL to about 1200 ng·hr/mL. In some embodiments, the present methods provide a mean $AUC_{0-24h}$ from about 800 ng·hr/mL to about 1400 ng·hr/mL. In some embodiments, the present methods provide a mean $AUC_{0-24h}$ from about 1000 ng·hr/mL to about 1600 ng·hr/mL. In some embodiments, the present methods provide a mean $AUC_{0-24h}$ from about 200 ng·hr/mL to about 600 ng·hr/mL. In some embodiments, the present methods provide a mean $AUC_{0-24h}$ from about 400 ng·hr/mL to about 800 ng·hr/mL. In some embodiments, the present methods provide a mean $AUC_{0-24h}$ from about 600 ng·hr/mL to about 1000 ng·hr/mL. In some embodiments, the present methods provide a mean $AUC_{0-24h}$ from about 800 ng·hr/mL to about 1200 ng·hr/mL. In some embodiments, the present methods provide a mean $AUC_{0-24h}$ from about 1000 ng·hr/mL to about 1400 ng·hr/mL. In some embodiments, the present methods provide a mean $AUC_{0-24h}$ from about 1200 ng·hr/mL to about 1600 ng·hr/mL. In some embodiments, the present methods provide a mean $AUC_{0-24h}$ from about 85 ng·hr/mL to about 1600 ng·hr/mL. In some embodiments, the present methods provide a mean $AUC_{0-24h}$ from about 440 ng·hr/mL to about 1245 ng·hr/mL. In some embodiments, the present methods provide a mean $AUC_{0-24h}$ from about 80 h*ng/mL to about 1600 h*ng/mL.

In some embodiments, the present methods provide a mean $AUC_{tau}$ from about 20 ng·hr/mL to about 800 ng·hr/mL In some embodiments, the present methods provide a mean $AUC_{tau}$ from about 40 ng·hr/mL to about 800 ng·hr/mL. In some embodiments, the present methods provide a mean $AUC_{tau}$ from about 40 ng·hr/mL to about 200 ng·hr/mL. In some embodiments, the present methods provide a mean $AUC_{tau}$ from about 180 ng·hr/mL to about 320 ng·hr/mL In some embodiments, the present methods provide a mean $AUC_{tau}$ from about 180 ng·hr/mL to about 320 ng·hr/mL. In some embodiments, the present methods provide a mean $AUC_{tau}$ from about 100 ng·hr/mL to about 400 ng·hr/mL. In some embodiments, the present methods provide a mean $AUC_{tau}$ from about 200 ng·hr/mL to about 500 ng·hr/mL. In some embodiments, the present methods provide a mean $AUC_{tau}$ from about 300 ng·hr/mL to about 600 ng·hr/mL. In some embodiments, the present methods provide a mean $AUC_{tau}$ from about 400 ng·hr/mL to about 700 ng·hr/mL. In some embodiments, the present methods provide a mean $AUC_{tau}$ from about 500 ng·hr/mL to about 800 ng·hr/mL. In some embodiments, the present methods provide a mean $AUC_{tau}$ from about 100 ng·hr/mL to about 300 ng·hr/mL. In some embodiments, the present methods provide a mean $AUC_{tau}$ from about 200 ng·hr/mL to about 400 ng·hr/mL. In some embodiments, the present methods provide a mean $AUC_{tau}$ from about 300 ng·hr/mL to about 500 ng·hr/mL. In some embodiments, the present methods provide a mean $AUC_{tau}$ from about 400 ng·hr/mL to about 600 ng·hr/mL. In some embodiments, the present methods provide a mean $AUC_{tau}$ from about 500 ng·hr/mL to about 700 ng·hr/mL. In some embodiments, the present methods provide a mean $AUC_{tau}$ from about 600 ng·hr/mL to about 800 ng·hr/mL. In some embodiments, the present methods provide a mean $AUC_{tau}$ from about 43.2 h*ng/mL to about 769.99 h*ng/mL. In some embodiments, the present methods provide a mean $AUC_{tau}$ from about 221.68 h*ng/mL to about 621.79 h*ng/mL. In some embodiments, the present methods provide a mean $AUC_{tau}$ from about 40 h*ng/mL to about 800 h*ng/mL.

In some embodiments, the methods of the present disclosure, comprise administering a tolerable and therapeutically effective dose of nalbuphine to a patient with a Child-Pugh score of A, wherein the administration provides in the subject with a Child-Pugh score of A, a PK release profile with the characteristics of a) a mean $C_{max}$ of about 24 ng/mL and b) a mean $AUC_{0-24h}$ of at least about 840 ng*hr/mL. In some embodiments, the mean $AUC_{0-24h}$ is about 840 ng*hr/mL. In some embodiments, the dose is about 180 mg BID of nalbuphine.

In some embodiments, the methods of the present disclosure, comprise administering a tolerable and therapeutically effective dose of nalbuphine to a patient with a Child-Pugh score of B, wherein the administration provides in the subject with a Child-Pugh score B a PK release profile with the characteristics of a) a mean $C_{max}$ of about 24 ng/mL and b) a mean $AUC_{0-24h}$ of about 840 ng*hr/mL. In some embodiments, the dose is from about 45 mg to about 150 mg of nalbuphine. In some embodiments, nalbuphine is administered once or twice daily. In some embodiments, nalbuphine is administered twice daily.

In some embodiments, the methods of the present disclosure comprise administering a tolerable and therapeutically effective dose of nalbuphine to a patient with a Child-Pugh score of C, wherein the administration provides in the subject with a Child-Pugh score B a PK release profile with the characteristics of a) a mean $C_{max}$ of about 24 ng/mL and b) a mean $AUC_{0-24h}$ of about 840 ng*hr/mL. In some embodiments, the dose is from about 20 mg to about 35 mg of nalbuphine. In some embodiments, nalbuphine is administered once or twice daily. In some embodiments, nalbuphine is administered twice daily.

In some embodiments, the nalbuphine metabolites include glucuronides (most likely on the phenol and cyclohexane rings), two hydroxylated nalbuphine metabolites (on the cyclobutane ring) and three ketones (hydroxylation of the cyclobutane ring, followed by oxidation to a carbonyl or followed by ring opening of the cyclobutane ring). In some embodiments, the nalbuphine metabolites include nalbuphine 3-glucuronide or 6-glucuronide. In some embodiments, the nalbuphine metabolites include triple hydroxylated nalbuphine, mono-hydroxylated nalbuphine, or mono-glucuronidated nalbuphine, or a combination thereof. In some embodiments, the one or more metabolites of nalbuphine do not have detectable anti-pruritus activity. In some embodiments, one or more of the metabolites of nalbuphine exhibit anti-pruritus activity.

In embodiments wherein one or more metabolites of nalbuphine exhibit anti-pruritus activity, the dosing regimen of nalbuphine may be adjusted and/or titrated as described hereinabove depending on the clearance rate of the one or more metabolites exhibiting anti-pruritic activity. Such dosage adjustment and/or titration of the dosage of nalbuphine can be performed to prevent accumulation of either the nalbuphine and/or one or more metabolites, which can also exhibit anti-pruritic activity, to avoid toxicity effects in a patient treated with the nalbuphine.

In some embodiments, nalbuphine is completely metabolized (e.g., about 100% metabolized). In some embodiments, nalbuphine is not completely metabolized (e.g., less than about 100% metabolized). For example, in some embodiments, the nalbuphine is about 100% metabolized, about 95% metabolized, about 90% metabolized, about 85% metabolized, about 80% metabolized, about 75% metabolized, about 70% metabolized, about 65% metabolized, about 60% metabolized, about 55% metabolized, about 50% metabolized, about 45% metabolized, about 40% metabolized, about 35% metabolized, about 25% metabolized, about 20% metabolized, about 15% metabolized, about 10% metabolized, about 5% metabolized, about 1% metabolized, or about 0% metabolized. In some embodiments, the amount of dialyzable agent can be measured or monitored by the level of accumulation, e.g., blood plasma level of nalbuphine, or one or more of its metabolites.

In some embodiments, the present disclosure provides kits for use in treating a nalbuphine treatable disorder (e.g., as described herein). Such kits comprise nalbuphine or a pharmaceutical composition comprising nalbuphine and a pharmaceutically acceptable carrier (e.g., as described herein). The kits of the present disclosure may be used for administering nalbuphine at different dosage intervals, or for titrating nalbuphine according to methods described herein. In some embodiments, the kits of the present disclosure may comprise directions for administration. For example, the kit can include instructions to administer nalbuphine in a suitable manner to perform the methods described herein, e.g., in a suitable dose, dosage form, dosing intervals (e.g., as described herein). In some embodiments, the informational material can include instructions to administer the nalbuphine to a suitable subject, e.g., a subject with impaired hepatic function (e.g., Child-Pugh A, B or C) as described herein.

The kit can include one or more containers for the compositions as described herein. In some embodiments, the kit contains separate containers, dividers or compartments for the composition and informational material. For example, the composition can be contained in a bottle, vial, or syringe. In some embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a composition described herein. For example, the kit can include a plurality of syringes, ampules, or foil packets each containing a single unit dose of a composition described herein. An example of such a kit is a blister pack, as typically used for the packaging of tablets, capsules and the like. The containers of the kits can be air tight, waterproof (e.g., impermeable to changes in moisture or evaporation), and/or light-tight.

In some embodiments, provided herein is a kit for treating a nalbuphine-treatable disorder (e.g., as described herein) in a hepatically impaired patient with a Child-Pugh score of A, comprising one or more AM and PM dosage units of about 15 mg to about 360 mg. In some embodiments, provided herein is a kit for treating a nalbuphine-treatable disorder (e.g., as described herein) in a hepatically impaired patient with a Child-Pugh score of A, comprising one or more AM and PM dosage units of nalbuphine or a pharmaceutically acceptable salt thereof selected from the group consisting of about 30 mg, about 60 mg, about 90 mg, about 120 mg, and about 180 mg. In some embodiments, the kit comprises one or more AM and PM dosage units of nalbuphine or a pharmaceutically acceptable salt thereof selected from the group consisting of about 30 mg, about 60 mg, about 90 mg, and about 120 mg. In some embodiments, provided herein is a kit for treating a nalbuphine-treatable disorder (e.g., as described herein) in a hepatically impaired patient with a Child-Pugh score of A, comprising one or more AM and PM dosage units of an the Equivalent Amount of Nalbuphine Free Base selected from the group consisting of about 27 mg, about 54 mg, about 108 mg, and about 162 mg.

In some embodiments, provided herein is a kit for treating a nalbuphine-treatable disorder (e.g., as described herein) in a hepatically impaired patient with a Child-Pugh score of B, comprising one or more AM and PM dosage units of about 4 mg to about 120 mg of nalbuphine, or a pharmaceutically acceptable salt thereof. In some embodiments, provided herein is a kit for treating a nalbuphine-treatable disorder (e.g., as described herein) in a hepatically impaired patient with a Child-Pugh score of B, comprising one or more AM and PM dosage units of nalbuphine or a pharmaceutically acceptable salt thereof selected from the group consisting of about 10-15 mg, about 20-31 mg, and about 40-60 mg. In some embodiments, the kit comprises one or more AM and PM dosage units of nalbuphine or a pharmaceutically acceptable salt thereof selected from the group consisting of about 10 mg, about 20 mg, about 40 mg, and about 60 mg. In some embodiments, the kit comprises one or more AM and PM dosage units of nalbuphine or a pharmaceutically acceptable salt thereof selected from the group consisting of about 15 mg, about 31 mg, and about 60 mg. In some embodiments, the kit comprises one or more AM and PM dosage units of nalbuphine or a pharmaceutically acceptable salt thereof selected from the group consisting of about 10-15 mg, about 20-31 mg, and about 40-60 mg. In some embodiments, the kit comprises one or more AM and PM dosage units of nalbuphine or a pharmaceutically acceptable salt thereof selected from the group consisting of about 10 mg, about 20 mg, about 40 mg, and about 60 mg. In some embodiments, the kit comprises one or more AM and PM dosage units of nalbuphine or a pharmaceutically acceptable salt thereof selected from the group consisting of about 15 mg, about 31 mg, and about 60 mg. In some embodiments, the kit comprises one or more AM and PM dosage units selected from the group consisting of about 30 mg, and about 60 mg of nalbuphine or a pharmaceutically acceptable salt thereof. In some embodiments, the kit comprises one or more AM and PM dosage units selected from the group consisting of about 27 mg, and about 54 mg of an Equivalent Amount of Nalbuphine Free Base.

In some embodiments, provided herein is a kit for treating a nalbuphine-treatable disorder (e.g., as described herein) in a hepatically impaired patient with a Child-Pugh score of C, comprising one or more AM and PM dosage units of nalbuphine or a pharmaceutically acceptable salt thereof wherein the dosage unit comprises from about 2 mg to about 45 mg of nalbuphine or a pharmaceutically acceptable salt thereof. In some embodiments, the kit comprises one or more AM and PM dosage units of nalbuphine or a pharmaceutically acceptable salt thereof of about 2-7 mg. In some embodiments, the kit comprises one or more AM and PM dosage units of nalbuphine or a pharmaceutically acceptable salt thereof selected from the group consisting of about 5-8 mg, about 10-15 mg, and about 20-27 mg. In some embodiments, the kit comprises one or more AM and PM dosage units of nalbuphine or a pharmaceutically acceptable salt thereof selected from the group consisting of about 5 mg, about 10 mg, and about 22-27 mg. In some embodiments, the kit comprises one or more AM and PM dosage units of nalbuphine or a pharmaceutically acceptable salt thereof selected from the group consisting of about 7 mg, about 15 mg, and about 22-27 mg. In some embodiments, the kit comprises one or more AM and PM dosage units of nalbuphine or a pharmaceutically acceptable salt thereof selected from the group consisting of about 4-7 mg, about 9-14 mg, and about 18-27 mg. In some embodiments, the kit comprises one or more AM and/or PM dosage units comprising 30 mg of nalbuphine or a pharmaceutically acceptable salt thereof. In some embodiments, the kit comprises one or more AM and PM dosage units comprising about 27 mg of an Equivalent Amount of Nalbuphine Free Base.

In some embodiments of the kits disclosed herein, the AM and PM dosage units are to be administered for about, or at least about 7 to about 30 days. In some embodiments, the AM and PM dosage units are to be administered for about, or at least about 17 days. In some embodiments, the AM and PM dosage units are to be administered for about, or at least about 14 days. In some embodiments, the AM and PM dosage units are to be administered for about 11 days. In some embodiments, the AM and PM dosage units are to be administered for about, or at least about 8 days. In some embodiments, the AM dosage unit is the same as the PM dosage unit. In some embodiments, the AM dosage unit is the different to the PM dosage unit.

In some embodiments, the present disclosure provides a kit for treating a nalbuphine-treatable disorder (e.g., as described herein) in a hepatically impaired patient with a Child-Pugh score of A, the kit comprising AM and PM dosage units of nalbuphine to be administered for 14 days to the patient, wherein the AM and PM dosage units are as shown in the following tables:

| Day | AM dosage (mg) | PM dosage (mg) |
|---|---|---|
| Day 1 | 0 | 30 |
| Day 2 | 0 | 30 |
| Day 3 | 30 | 30 |
| Day 4 | 30 | 30 |
| Day 5 | 30 | 60 |
| Day 6 | 60 | 60 |
| Day 7 | 60 | 60 |
| Day 8 | 60 | 90 |
| Day 9 | 90 | 90 |
| Day 10 | 90 | 90 |
| Day 11 | 90 | 120 |
| Day 12 | 120 | 120 |
| Day 13 | 120 | 120 |
| Day 14 | 120 | 180 |
| Day 1 | 0 | 30 |
| Day 2 | 0 | 30 |
| Day 3 | 30 | 30 |
| Day 4 | 30 | 30 |
| Day 5 | 30 | 60 |

-continued

| Day | AM dosage (mg) | PM dosage (mg) |
|---|---|---|
| Day 6 | 60 | 60 |
| Day 7 | 60 | 60 |
| Day 8 | 60 | 90 |
| Day 9 | 90 | 90 |
| Day 10 | 90 | 90 |
| Day 11 | 90 | 120 |
| Day 12 | 120 | 120 |
| Day 13 | 120 | 120 |
| Day 14 | 120 | 120 |

In some embodiments, the present disclosure provides a kit for treating a nalbuphine-treatable disorder (e.g., as described herein) in a hepatically impaired patient with a Child-Pugh score of A, the kit comprising: AM and PM dosage units of nalbuphine to be administered for 17 days to the patient, wherein the AM and PM dosage units are as shown in the following tables:

| Day | AM dosage (mg) | PM dosage (mg) |
|---|---|---|
| Day 1 | 0 | 30 |
| Day 2 | 0 | 30 |
| Day 3 | 30 | 30 |
| Day 4 | 30 | 30 |
| Day 5 | 30 | 60 |
| Day 6 | 60 | 60 |
| Day 7 | 60 | 60 |
| Day 8 | 60 | 60 |
| Day 9 | 60 | 120 |
| Day 10 | 120 | 120 |
| Day 11 | 120 | 120 |
| Day 12 | 120 | 120 |
| Day 13 | 120 | 120 |
| Day 14 | 120 | 120 |
| Day 15 | 120 | 120 |
| Day 16 | 120 | 180 |
| Day 17 | 180 | 180 |

In some embodiments, the present disclosure provides a kit for treating a nalbuphine-treatable disorder (e.g., as described herein) in a hepatically impaired patient with a Child-Pugh score of B, the kit comprising AM and PM dosage units of nalbuphine to be administered for 11 days to the patient, wherein the AM and PM dosage units are as shown in the following tables:

| Day | AM dosage (mg) | PM dosage (mg) |
|---|---|---|
| Day 1 | 0 | 10-15 |
| Day 2 | 0 | 10-15 |
| Day 3 | 0 | 10-15 |
| Day 4 | 10-15 | 10-15 |
| Day 5 | 10-15 | 10-15 |
| Day 6 | 10-15 | 20-31 |
| Day 7 | 20-31 | 20-31 |
| Day 8 | 20-31 | 20-31 |
| Day 9 | 20-31 | 20-31 |
| Day 10 | 20-31 | 40-60 |
| Day 11 | 60 | 60 |

| Day | AM dosage (mg) | PM dosage (mg) |
|---|---|---|
| Day 1 | 0 | 10 |
| Day 2 | 0 | 10 |
| Day 3 | 0 | 10 |
| Day 4 | 10 | 10 |

| Day | AM dosage (mg) | PM dosage (mg) |
| --- | --- | --- |
| Day 5 | 10 | 10 |
| Day 6 | 10 | 20 |
| Day 7 | 20 | 20 |
| Day 8 | 20 | 20 |
| Day 9 | 20 | 20 |
| Day 10 | 20 | 40 |
| Day 11 | 60 | 60 |

| Day | AM dosage (mg) | PM dosage (mg) |
| --- | --- | --- |
| Day 1 | 0 | 15 |
| Day 2 | 0 | 15 |
| Day 3 | 0 | 15 |
| Day 4 | 15 | 15 |
| Day 5 | 15 | 15 |
| Day 6 | 15 | 31 |
| Day 7 | 31 | 31 |
| Day 8 | 31 | 31 |
| Day 9 | 31 | 31 |
| Day 10 | 31 | 60 |
| Day 11 | 60 | 60 |

In some embodiments, the present disclosure provides a kit for treating a nalbuphine-treatable disorder (e.g., as described herein) in a hepatically impaired patient with a Child-Pugh score of B, the kit comprising: AM and PM dosage units of nalbuphine to be administered for 8 days to the patient, wherein the AM and PM dosage units are as shown in the following tables:

| Day | AM dosage (mg) | PM dosage (mg) |
| --- | --- | --- |
| Day 1 | 0 | 10-15 |
| Day 2 | 10-15 | 10-15 |
| Day 3 | 10-15 | 10-15 |
| Day 4 | 10-15 | 20-31 |
| Day 5 | 20-31 | 20-31 |
| Day 6 | 20-31 | 20-31 |
| Day 7 | 20-31 | 40-60 |
| Day 8 | 60 | 60 |

| Day | AM dosage (mg) | PM dosage (mg) |
| --- | --- | --- |
| Day 1 | 0 | 10 |
| Day 2 | 10 | 10 |
| Day 3 | 10 | 10 |
| Day 4 | 10 | 20 |
| Day 5 | 20 | 20 |
| Day 6 | 20 | 20 |
| Day 7 | 20 | 40 |
| Day 8 | 60 | 60 |

| Day | AM dosage (mg) | PM dosage (mg) |
| --- | --- | --- |
| Day 1 | 0 | 15 |
| Day 2 | 15 | 15 |
| Day 3 | 15 | 15 |
| Day 4 | 15 | 31 |
| Day 5 | 31 | 31 |
| Day 6 | 31 | 31 |
| Day 7 | 31 | 60 |
| Day 8 | 60 | 60 |

In some embodiments, the present disclosure provides a kit for treating a nalbuphine-treatable disorder (e.g., as described herein) in a hepatically impaired patient with a Child-Pugh score of C, the kit comprising: AM and PM dosage units of nalbuphine to be administered for 11 days to the patient, wherein the AM and PM dosage units are as shown in the following tables:

| Day | AM dosage (mg) | PM dosage (mg) |
| --- | --- | --- |
| Day 1 | 0 | 5-8 |
| Day 2 | 0 | 5-8 |
| Day 3 | 0 | 5-8 |
| Day 4 | 5-8 | 5-8 |
| Day 5 | 5-8 | 5-8 |
| Day 6 | 5-8 | 10-15 |
| Day 7 | 10-15 | 10-15 |
| Day 8 | 10-15 | 10-15 |
| Day 9 | 10-15 | 10-15 |
| Day 10 | 10-15 | 20-27 |
| Day 11 | 20-27 | 20-27 |

| Day | AM dosage (mg) | PM dosage (mg) |
| --- | --- | --- |
| Day 1 | 0 | 5 |
| Day 2 | 0 | 5 |
| Day 3 | 0 | 5 |
| Day 4 | 10 | 5 |
| Day 5 | 10 | 5 |
| Day 6 | 10 | 10 |
| Day 7 | 10 | 10 |
| Day 8 | 10 | 10 |
| Day 9 | 10 | 10 |
| Day 10 | 10 | 22-27 |
| Day 11 | 22-27 | 22-27 |

| Day | AM dosage (mg) | PM dosage (mg) |
| --- | --- | --- |
| Day 1 | 0 | 7 |
| Day 2 | 0 | 7 |
| Day 3 | 0 | 7 |
| Day 4 | 7 | 7 |
| Day 5 | 7 | 7 |
| Day 6 | 7 | 15 |
| Day 7 | 15 | 15 |
| Day 8 | 15 | 15 |
| Day 9 | 15 | 15 |
| Day 10 | 15 | 22-27 |
| Day 11 | 22-27 | 22-27 |

In some embodiments, the present disclosure provides a kit for treating a nalbuphine-treatable disorder (e.g., as described herein) in a hepatically impaired patient with a Child-Pugh score of C, the kit comprising: AM and PM dosage units of nalbuphine to be administered for 8 days to the patient, wherein the AM and PM dosage units are as shown in the following table:

| Day | AM dosage (mg) | PM dosage (mg) |
| --- | --- | --- |
| Day 1 | 0 | 4-7 |
| Day 2 | 4-7 | 4-7 |
| Day 3 | 4-7 | 4-7 |
| Day 4 | 4-7 | 9-14 |
| Day 5 | 9-14 | 9-14 |
| Day 6 | 9-14 | 9-14 |

-continued

| Day | AM dosage (mg) | PM dosage (mg) |
|---|---|---|
| Day 7 | 9-14 | 18-27 |
| Day 8 | 18-27 | 18-27 |

The embodiments described herein should be understood to be illustrative of the present disclosure, and should not be construed as limiting. On the contrary, the present disclosure embraces alternatives and equivalents thereof, as embodied by the appended claims. Each reference disclosed herein is incorporated by reference herein in its entirety.

The following non-limiting examples illustrate various aspects of the present disclosure.

EXAMPLES

Example 1

A 30 mg, 60 mg, 120 or 180 mg extended release (ER) nalbuphine tablet was prepared as follows: Nalbuphine HCl, mannitol, xanthan gum, locust bean gum and calcium sulfate dihydrate were added to a high shear mixer and dried mix at low speed. A granulating solution (water for injection or purified water) was introduced into the mixer at low speed. The wet granulation was granulated at high speed and dried in a fluid bed processor. The dried granules were milled and sized using a conventional mill. The milled granulation was transferred into a diffusion (tumble) mixer. Hydroxypropylcellulose and, when applicable, fumaric acid (180 mg formulations only) were added to the diffusion mixer and blended. Thereafter, magnesium stearate was added to the diffusion mixer and blended. The final blend was compressed using a rotary tablet press. Tablets may be coated with a non-functional Opadry white coating.

TABLE 1

30 mg, 60 mg, 120 mg and 180 mg Extended Release Nalbuphine Tablet

| Ingredient | mg/tablet |
|---|---|
| Nalbuphine HCl | 29.8 |
| Mannitol | 107.3 |
| Hydroxypropylcellulose | 34.7 |
| Locust bean gum | 32.2 |
| Xanthan gum | 21.4 |
| Calcium sulfate dehydrate | 17.9 |
| Magnesium stearate | 1.9 |
| Water for injection or Purified water | QS |
| Total: | 245.1 |
| Nalbuphine HCl | 59.5 |
| Mannitol | 71.5 |
| Hydroxypropylcellulose | 29.8 |
| Locust bean gum | 21.4 |
| Xanthan gum | 14.3 |
| Calcium sulfate dehydrate | 11.9 |
| Magnesium stearate | 1.6 |
| Water for injection or Purified water | QS |
| Total: | 210.0 |
| Nalbuphine HCl | 119.0 |
| Mannitol | 143.0 |
| Hydroxypropylcellulose | 59.6 |
| Locust bean gum | 42.9 |
| Xanthan gum | 28.6 |
| Calcium sulfate dehydrate | 23.8 |
| Magnesium stearate | 3.2 |
| Water for injection or Purified water | QS |
| Total: | 432.6 |
| Nalbuphine HCl | 178.5 |
| Mannitol | 160.8 |
| Hydroxypropylcellulose | 59.6 |
| Locust bean gum | 48.2 |
| Xanthan gum | 32.2 |
| Calcium sulfate dehydrate | 26.8 |
| Magnesium stearate | 4.0 |
| Fumaric acid | 24.8 |
| Water for injection or Purified water | QS |
| Total: | 246.9 |

The tablets were coated with a non-functional coat (Opadry II White).

TABLE 2

Nalbuphine HCl ER Tablets, 30 mg, 60 mg, or 180 mg Compositions

| Component | Tablet (mg/tablet) |
|---|---|
| Nalbuphine HCl | 30.0 |
| Mannitol | 108.0 |
| Hydroxypropylcellulose | 35.0 |
| Locust bean gum | 32.4 |
| Xanthan gum | 21.6 |
| Calcium sulfate dihydrate | 18.0 |
| Magnesium stearate | 1.9 |
| Opadry II White | 7.4 |
| Sterile water for irrigation | QS |
| Total | 254.3 |
| Nalbuphine HCl | 60.0 |
| Mannitol | 72.0 |
| Hydroxypropylcellulose | 30.0 |
| Locust bean gum | 21.6 |
| Xanthan gum | 14.4 |
| Calcium sulfate dihydrate | 12.0 |
| Magnesium stearate | 1.6 |
| Opadry II White | 6.355 |
| Sterile water for irrigation | QS |
| Total | 218 |
| Nalbuphine HCl | 180 |
| Mannitol | 160.8 |
| Hydroxypropylcellulose | 59.6 |
| Locust bean gum | 48.2 |
| Fumaric acid | 24.8 |
| Xanthan gum | 32.2 |
| Calcium sulfate dihydrate | 26.8 |
| Magnesium stearate | 4.0 |
| Sterile water for irrigation | QS |
| Total | 534.9 |

Example 2

Liver-impaired patients are treated with Nalbuphine extended release (ER) tablets, prepared according to the formulations described herein, in a single-ascending dose study to determine the effect of hepatic impairment on the pharmacokinetics at steady state as a function of dose. Healthy subjects receive a single dose of drug at the highest dose studied in the liver-impaired subjects in order to make relative comparison to the PK aspects of Nalbuphine extended release (ER). If the PK data demonstrates dose linearity across the dose range in both the mild and moderate hepatic impairment subjects, such that PK modeling can be predictive of steady state dosing levels.

Study Design

The study is an open label, single ascending dose (SAD) study and consists of five cohorts that each receive Nalbuphine ER tablets of the present disclosure. Cohort 1 consists of subjects with impaired hepatic function divided into three groups with some subjects in each of the mild Child-Pugh A category (Group 1), the moderate Child-Pugh B category (Group 2), and the severe Child-Pugh category C (Group 3). Cohort 2-4 consists of subjects with impaired hepatic function divided into two groups with some subjects in each of the mild Child-Pugh A category (Group 1), and the moderate Child-Pugh B category (Group 2). Cohort 5 consists of healthy control subjects who have been appropriately age-, body mass index (BMI), and gender-matched to subjects with mild and moderate hepatic impairment from Cohorts 1 to 4.

Part 1:

Dosing: Subjects receive a single ascending dose, under fasting condition, at the following dose levels:

| Cohort | Dose |
|---|---|
| 1 | 27 mg |
| 2 | 54 mg |
| 3 | 108 mg |
| 4 | 162 mg |
| 5 | 162 mg |

Each of the cohorts is dosed sequentially starting with the lowest dose. Subjects with mild or moderate hepatic impairment enrolled in Cohort 1 are optionally enrolled in Cohorts 2, 3, and 4. For each dose cohort, enrollment of subjects with mild or moderate hepatic impairment is done in parallel. An evaluation of safety and tolerability of the combined mild and moderate hepatic impairment subject data is done at each dose level before proceeding to the next dose level.

Subjects with severe impairment were enrolled only in Cohort 1 (single dose of 27 mg) following completion of the highest dose tested in subjects with mild or moderate impairment.

The drug kinetics in the hepatic impairment subject population is compared relative to the healthy subject population.

Blood is obtained for each cohort at designated times for PK and other analyses (see below). Standard safety assessments are measured during each treatment period.

Protocol:

Blood: Blood from the patients of each cohort is collected in $K_2$EDTA tubes. The plasma fractions are separated by centrifugation and stored frozen until analysis. Blood samples are collected at the following time points: 0 h (prior to the dose), 1.5, 3, 5, 7, 9, 12, 24, 36, 48, and 72 h after the dose.

Safety Assessments/Monitoring

Adverse events (AEs) are monitored throughout the duration of the study.

To monitor for possible adverse events, sitting blood pressure, heart rate, body temperature, clinical laboratory tests (hematology, chemistry, and urinalysis) and respiration rate are monitored and physical examination and 12-lead ECG is conducted during the study.

Statistical Analysis

Statistical analysis is conducted using statistical methods that are approved for use in FDA clinical trials.

The following pharmacokinetic parameters are calculated by standard non-compartmental methods for nalbuphine and metabolites (if required).

1) $AUC_{0-t}$: area under the concentration-time curve from time zero to the last non-zero concentration;
2) $AUC_{0-inf}$: area under the concentration-time curve from time zero to infinity (extrapolated);
3) $C_{max}$: maximum observed concentration;
4) $T_{max}$: time of observed $C_{max}$;
5) $T_{1/2\ el}$: elimination half-life;
6) Residual area: calculated as $100*(1-AUC_{0-t}/AUC_{0-inf})$;
7) $K_{el}$: elimination rate constant;
8) Cl/F: apparent total body clearance of the drug from plasma; and
9) Vd/F: apparent volume of distribution, calculated as $Dose/(K_{el} \times AUC_{0-inf})$.

Results

Figure 2:
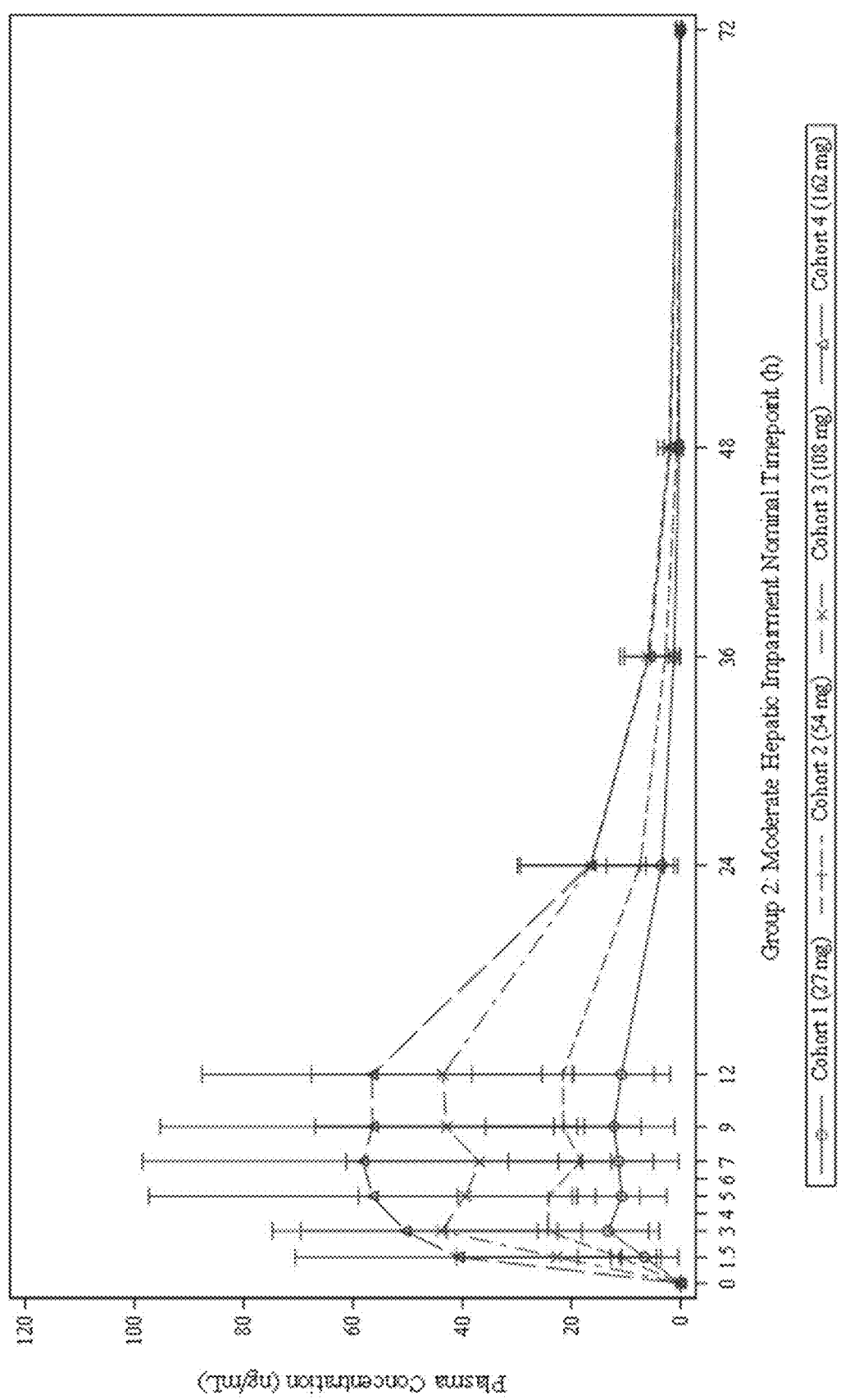
FIG. 2 shows the mean (±SD) plasma concentrations of nalbuphine in patients with moderate hepatic impairment (Child Pugh B); in Cohorts 1-4 in Example 2) following single dose administration of 27 mg, 54 mg, 108 mg and 162 mg Nalbuphine extended release tablet.
Figure 3:
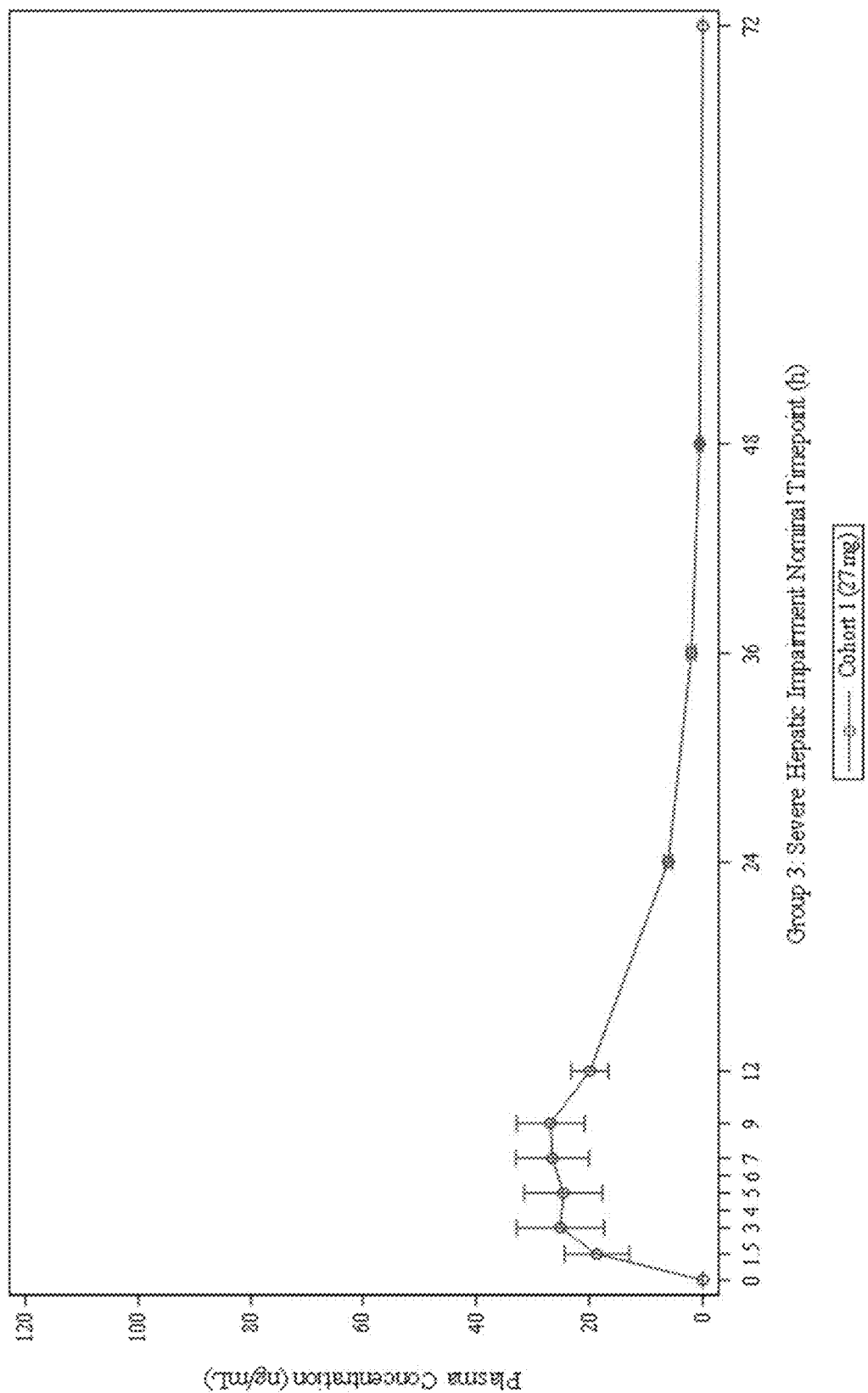
FIG. 3 shows the mean (±SD) plasma concentrations of nalbuphine in patients with severe hepatic impairment (Child Pugh C); in Cohort 1 in Example 2) following single dose administration of 27 mg of Nalbuphine extended release tablet.
Figure 4:
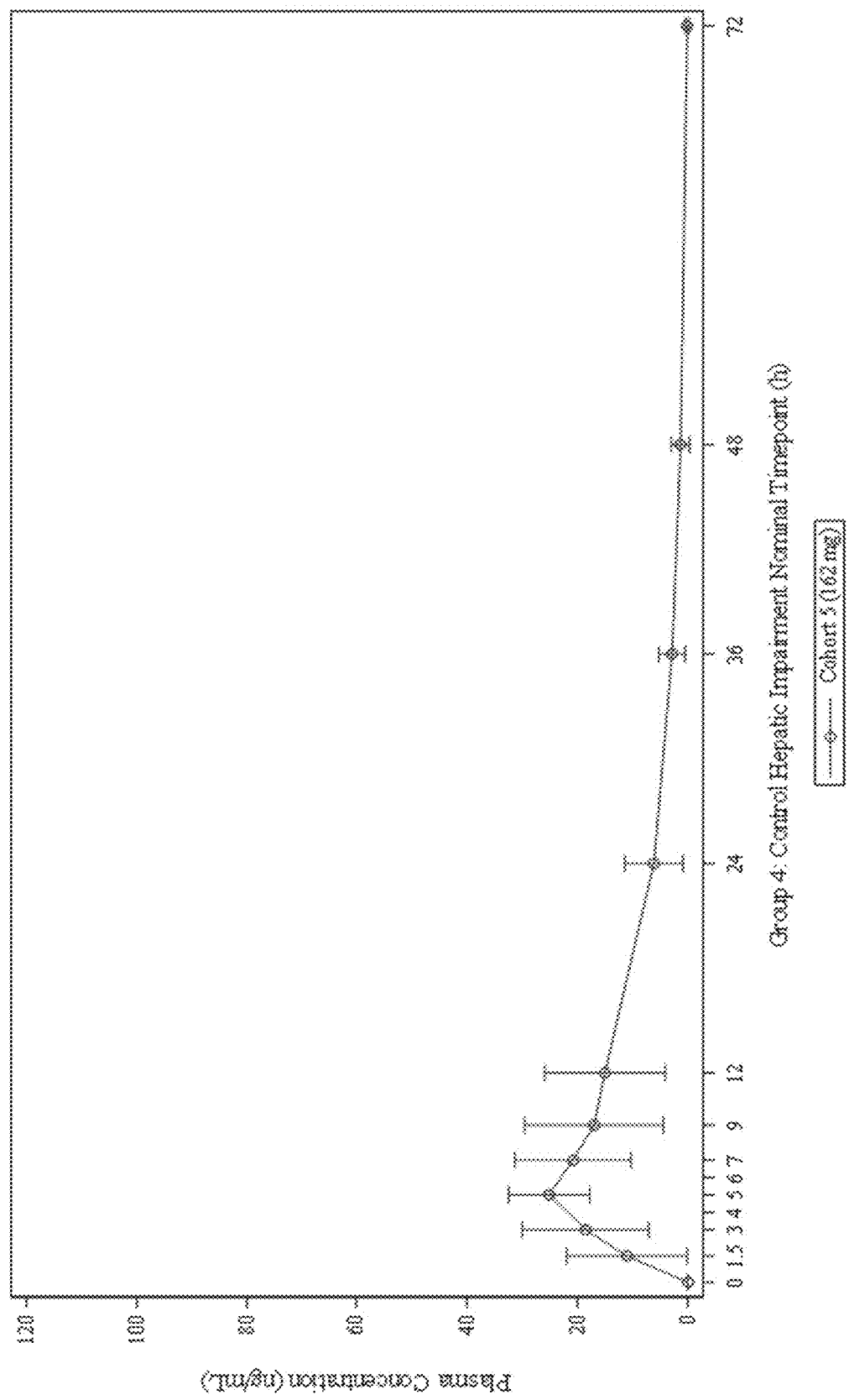
FIG. 4 shows the mean (±SD) plasma concentrations of nalbuphine in healthy control patients; in Cohort 5 in Example 2) following single dose administration of 162 mg of Nalbuphine extended release tablet.
Figure 5:
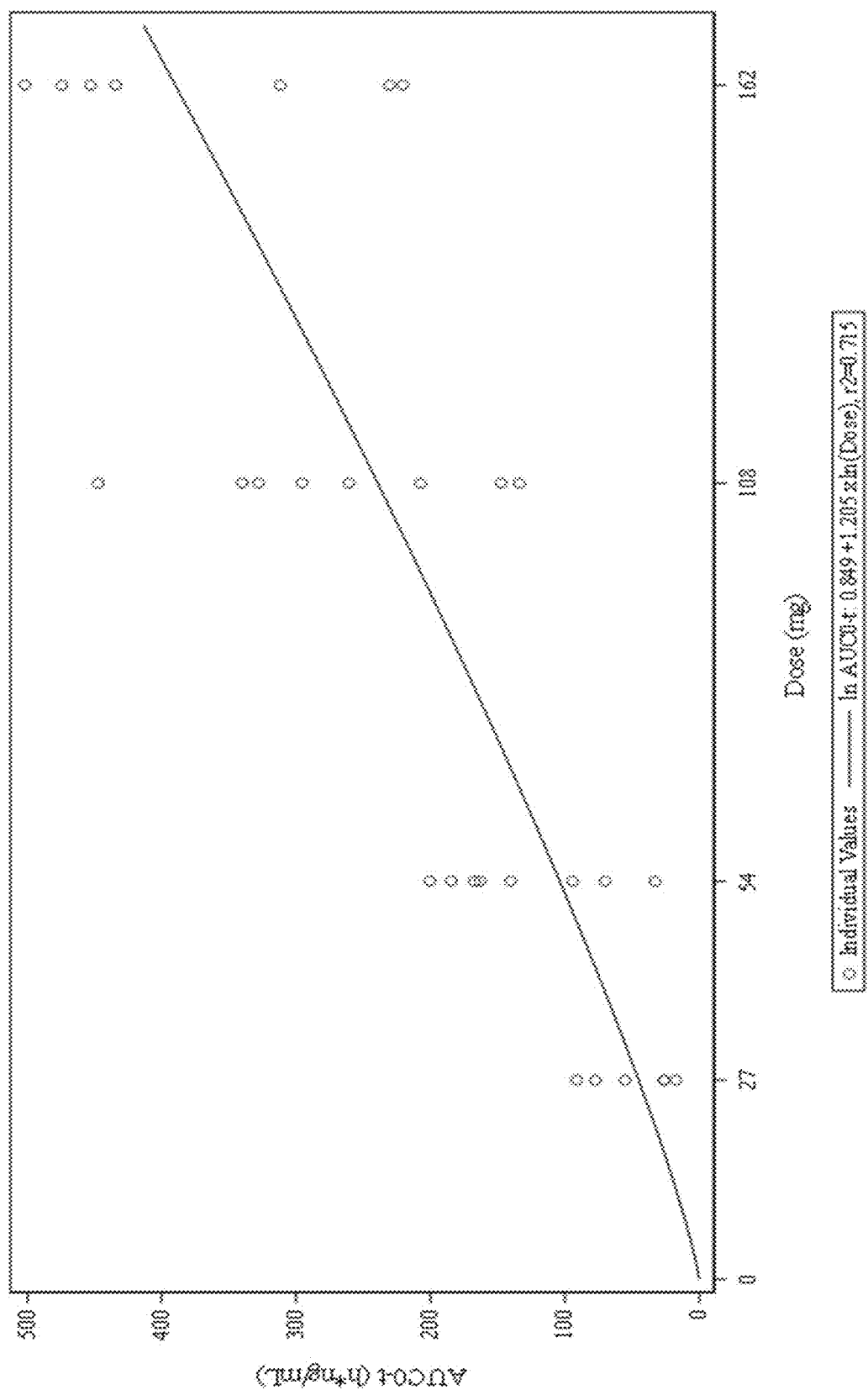
FIG. 5 shows nalbuphine mean $AUC_{0-t}$ versus dose for patients with mild hepatic impairment.
Figure 6:
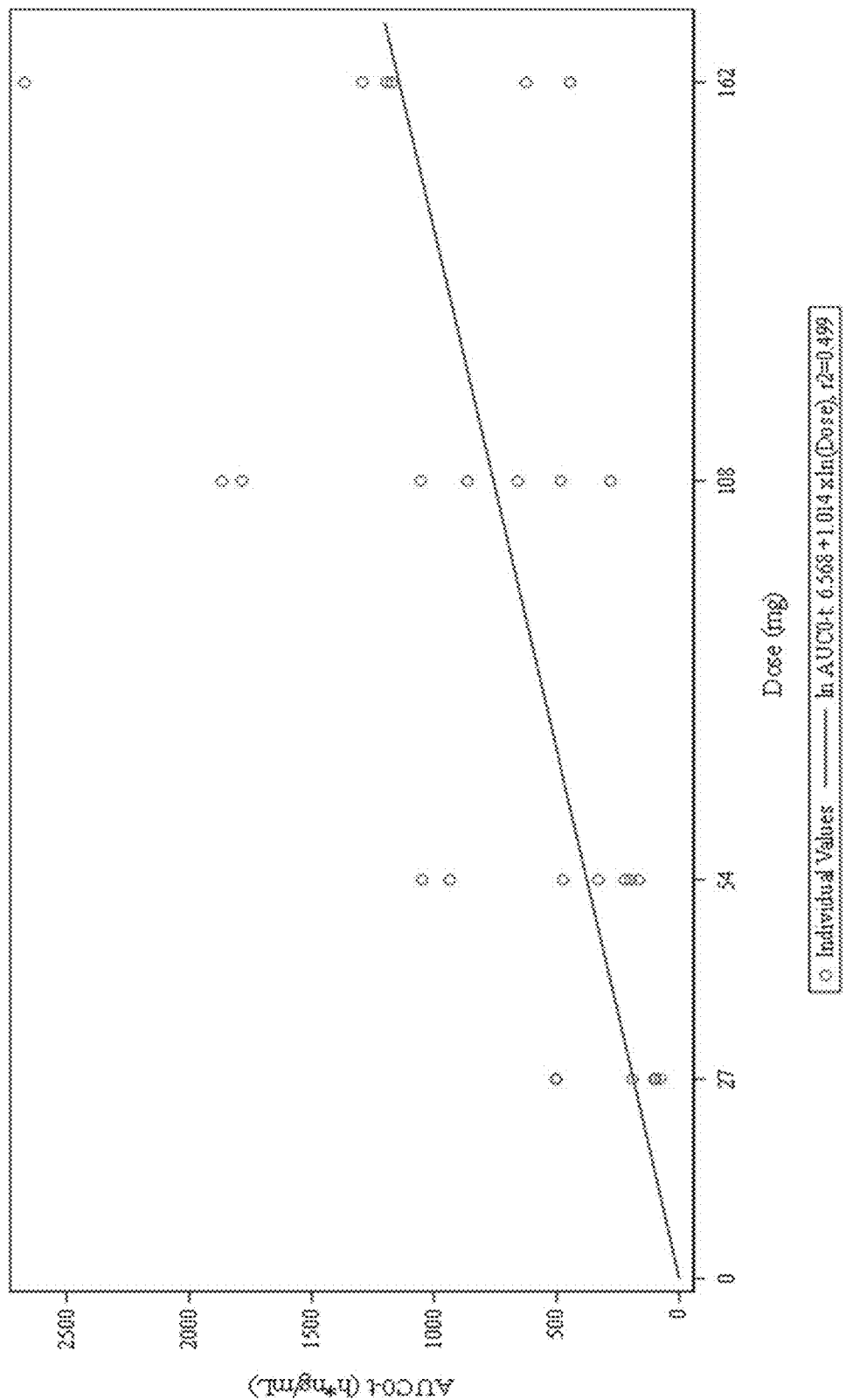
FIG. 6 shows nalbuphine mean $AUC_{0-t}$ versus dose for patients with moderate hepatic impairment.
Figure 7:
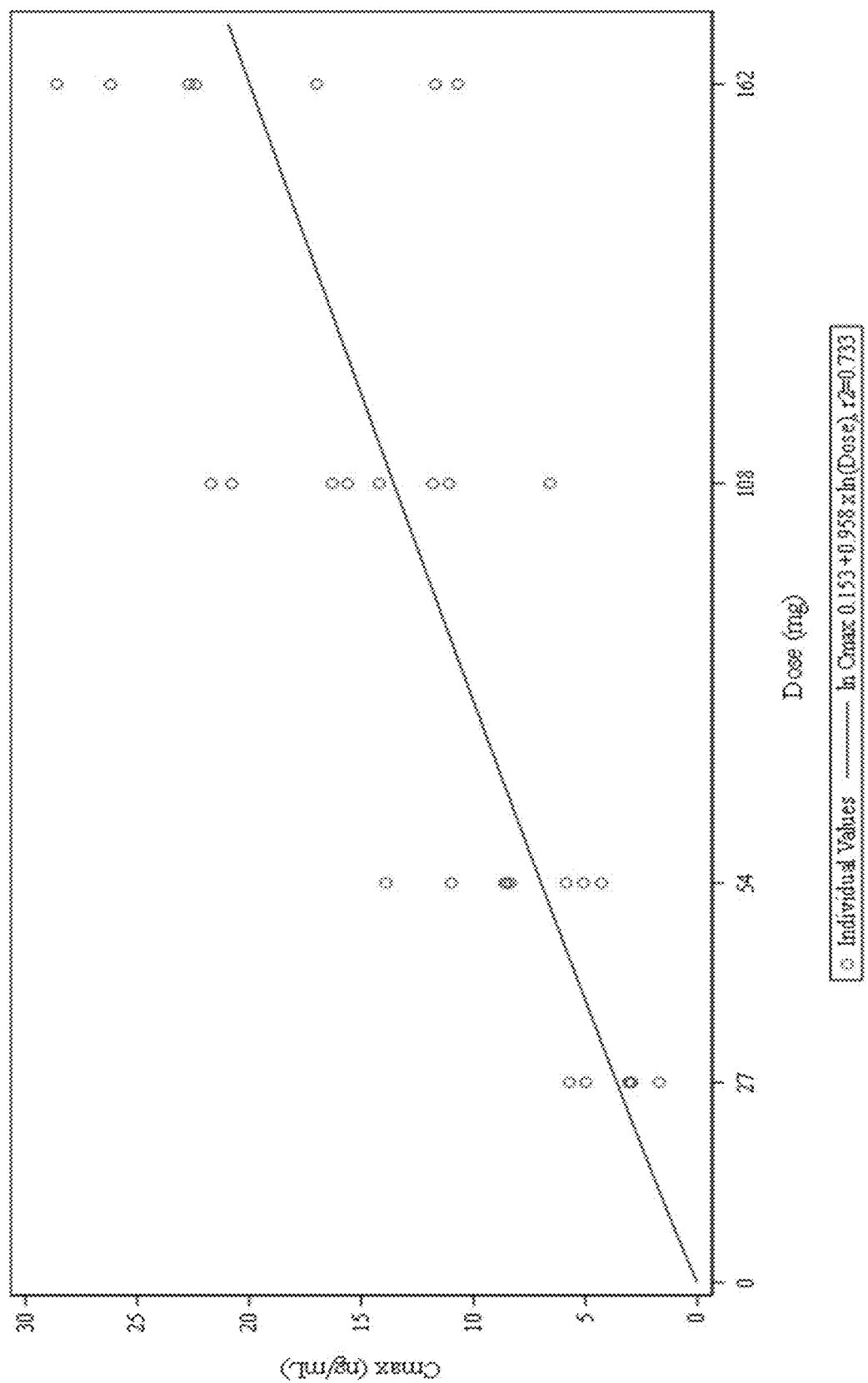
FIG. 7 shows nalbuphine mean $C_{max}$ versus dose for patients with mild hepatic impairment.
Figure 8:
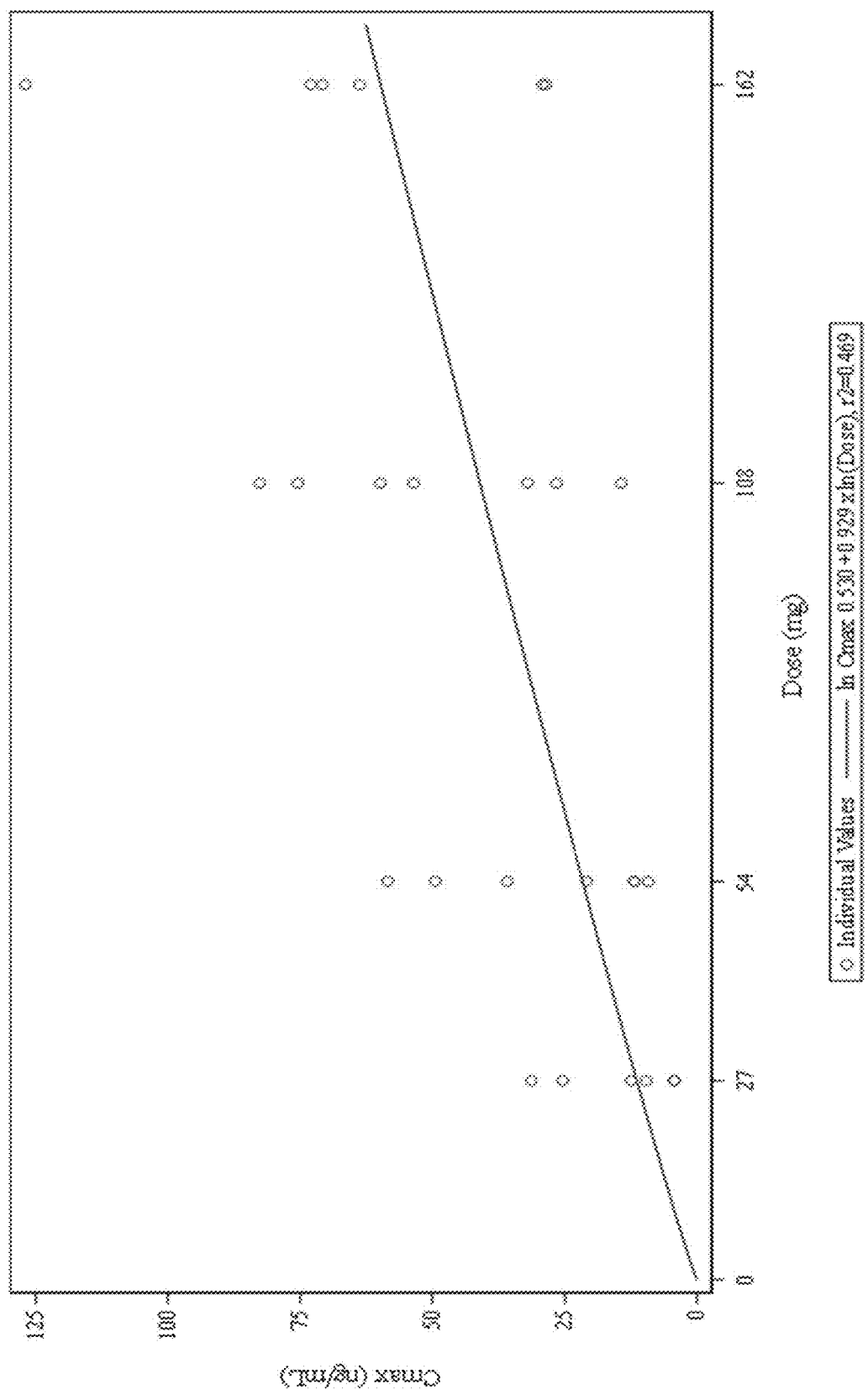
FIG. 8 shows nalbuphine mean $C_{max}$ versus dose for patients with moderate hepatic impairment.

The mean plasma concentrations of Nalbuphine in patients from cohorts 1-4 for each hepatic impairment group (i.e. mild, moderate, severe, hepatic impairment, and healthy controls) are depicted in FIGS. 1-4. As depicted in FIGS. 5-8, patients from Cohorts 1-4 with mild or moderate hepatic impairment demonstrated dose proportional nalbuphine plasma concentration-time profiles following single dose administration of Nalbuphine ER.

Table 2A below provides a summary of the observed plasma pharmacokinetic parameters for Nalbuphine following administration of Nalbuphine ER tablets (27 mg, Single Dose) in patients from Cohort 1 with mild hepatic impairment.

TABLE 2A

| Parameter (unit) | N | Mean | SD | CV % | Min | Median | Max | Geometric Mean |
|---|---|---|---|---|---|---|---|---|
| $AUC_{0-inf}$ (h*ng/mL) | 4 | 72.31 | 26.49 | 36.63 | 38.97 | 75.70 | 98.87 | 68.15 |
| $AUC_{0-t}$ (h*ng/mL) | 6 | 48.89 | 30.54 | 62.46 | 17.48 | 40.71 | 91.25 | 40.82 |
| Residual area (%) | 4 | 16.58 | 11.39 | 68.69 | 7.70 | 12.69 | 33.23 | 14.22 |
| $C_{max}$ (ng/mL) | 6 | 3.56 | 1.49 | 41.8 | 1.70 | 3.03 | 5.71 | 3.30 |
| $T_{max}$ (h) | 6 | 4.417 | 2.289 | 51.837 | 1.500 | 4.000 | 7.000 | 3.860 |
| $T_{1/2\ el}$ (h) | 4 | 8.60 | 2.71 | 31.53 | 6.46 | 7.83 | 12.27 | 8.30 |
| $K_{el}$ (/h) | 4 | 0.0862 | 0.0241 | 27.9590 | 0.0565 | 0.0906 | 0.1073 | 0.0835 |

TABLE 2A-continued

| Parameter (unit) | N | Mean | SD | CV % | Min | Median | Max | Geometric Mean |
|---|---|---|---|---|---|---|---|---|
| Cl/F (L/h) | 4 | 424.04 | 189.88 | 44.78 | 273.10 | 365.10 | 692.86 | 396.20 |
| $V_d$/F (L) | 4 | 5105.47 | 2181.17 | 42.72 | 2967.55 | 5004.85 | 7444.63 | 4744.89 |

N: number of observations;
SD: Standard deviation;
CV: Coefficient of Variation;
Min: minimum;
Max: Maximum;
'—': not calculated;
Group 1 = Subjects with mild hepatic impairment Table 2B below provides a summary of the observed plasma pharmacokinetic parameters for Nalbuphine following administration of Nalbuphine ER tablets (27 mg, Single Dose) in patients from Cohort 1 with moderate hepatic impairment.

TABLE 2B

| Parameter (unit) | N | Mean | SD | CV % | Min | Median | Max | Geometric Mean |
|---|---|---|---|---|---|---|---|---|
| $AUC_{0-inf}$ (h*ng/mL) | 6 | 254.39 | 203.03 | 79.81 | 86.69 | 154.89 | 514.54 | 194.12 |
| $AUC_{0-t}$ (h*ng/mL) | 6 | 244.03 | 203.18 | 83.26 | 75.65 | 144.77 | 503.02 | 180.63 |
| Residual area (%) | 6 | 6.81 | 5.51 | 80.90 | 1.82 | 4.70 | 14.65 | 5.05 |
| $C_{max}$ (ng/mL) | 6 | 14.6 | 11.3 | 77.9 | 4.20 | 11.0 | 31.4 | 10.9 |
| $T_{max}$ (h) | 6 | 4.667 | 2.658 | 56.964 | 3.000 | 3.000 | 9.000 | 4.149 |
| $T_{1/2\ el}$ (h) | 6 | 8.45 | 2.54 | 30.06 | 5.15 | 7.97 | 11.77 | 8.13 |
| $K_{el}$ (/h) | 6 | 0.0888 | 0.0279 | 31.4733 | 0.0589 | 0.0873 | 0.1346 | 0.0853 |
| Cl/F (L/h) | 6 | 174.70 | 109.99 | 62.96 | 52.47 | 188.41 | 311.47 | 139.09 |
| $V_d$/F (L) | 6 | 2247.23 | 1845.83 | 82.14 | 572.12 | 1617.16 | 4961.24 | 1631.11 |

N: number of observations;
SD: Standard deviation;
CV: Coefficient of Variation;
Min: minimum;
Max: Maximum;
'—': not calculated Table 2C below provides a summary of the observed plasma pharmacokinetic parameters for Nalbuphine following administration of Nalbuphine ER tablets (27 mg, Single Dose) in patients from Cohort 1 with severe hepatic impairment.

TABLE 2C

| Parameter (unit) | N | Mean | SD | CV % | Min | Median | Max | Geometric Mean |
|---|---|---|---|---|---|---|---|---|
| $AUC_{0-inf}$ (h*ng/mL) | 4 | 498.34 | 100.74 | 20.21 | 413.89 | 469.32 | 640.81 | 491.26 |
| $AUC_{0-t}$ (h*ng/mL) | 4 | 489.19 | 98.54 | 20.14 | 408.92 | 459.76 | 628.32 | 482.29 |
| Residual area (%) | 4 | 1.82 | 0.67 | 36.95 | 1.20 | 1.69 | 2.72 | 1.74 |
| $C_{max}$ (ng/mL) | 4 | 28.3 | 6.19 | 21.9 | 21.7 | 27.6 | 36.1 | 27.7 |
| $T_{max}$ (h) | 4 | 6.000 | 3.464 | 57.735 | 3.000 | 6.000 | 9.000 | 5.196 |
| $T_{1/2\ el}$ (h) | 4 | 7.17 | 0.85 | 11.78 | 6.24 | 7.22 | 8.02 | 7.14 |
| $K_{el}$ (/h) | 4 | 0.0976 | 0.0117 | 11.9455 | 0.0865 | 0.0965 | 0.1111 | 0.0971 |
| Cl/F (L/h) | 4 | 55.69 | 10.05 | 18.05 | 42.13 | 57.70 | 65.24 | 54.96 |
| $V_d$/F (L) | 4 | 568.73 | 64.68 | 11.37 | 487.27 | 578.64 | 630.39 | 565.90 |

N: number of observations;
SD: Standard deviation;
CV: Coefficient of Variation;
Min: minimum;
Max: Maximum;
'—': not calculated Table 3A below provides a summary of the observed plasma pharmacokinetic parameters for Nalbuphine following administration of Nalbuphine ER tablets (54 mg, Single Dose) in patients from Cohort 2 with mild hepatic impairment.

TABLE 3A

| Parameter (unit) | N | Mean | SD | CV % | Min | Median | Max | Geometric Mean |
|---|---|---|---|---|---|---|---|---|
| $AUC_{0-inf}$ (h*ng/mL) | 5 | 152.31 | 65.09 | 42.73 | 84.28 | 151.67 | 249.44 | 141.56 |
| $AUC_{0-t}$ (h*ng/mL) | 8 | 131.53 | 59.55 | 45.27 | 32.76 | 151.73 | 200.30 | 114.96 |
| Residual area (%) | 5 | 12.98 | 8.47 | 65.27 | 5.90 | 8.55 | 26.05 | 11.06 |
| $C_{max}$ (ng/mL) | 8 | 8.20 | 3.19 | 38.9 | 4.27 | 8.43 | 13.9 | 7.67 |
| $T_{max}$ (h) | 8 | 6.250 | 3.955 | 63.282 | 3.000 | 5.000 | 12.000 | 5.244 |
| $T_{1/2\ el}$ (h) | 5 | 11.36 | 2.68 | 23.58 | 7.94 | 11.92 | 14.08 | 11.09 |
| $K_{el}$ (/h) | 5 | 0.0641 | 0.0164 | 25.6070 | 0.0492 | 0.0582 | 0.0873 | 0.0625 |
| Cl/F (L/h) | 5 | 409.94 | 170.63 | 41.62 | 216.48 | 356.04 | 640.69 | 381.46 |
| $V_d$/F (L) | 5 | 6860.25 | 3826.34 | 55.78 | 3571.31 | 6977.86 | 13013.00 | 6103.33 |

N: number of observations;
SD: Standard deviation;
CV: Coefficient of Variation;
Min: minimum;
Max: Maximum;
'—': not calculated Table 3B below provides a summary of the observed plasma pharmacokinetic parameters for Nalbuphine following administration of Nalbuphine ER tablets (54 mg, Single Dose) in patients from Cohort 2 with moderate hepatic impairment.

TABLE 3B

| Parameter (unit) | N | Mean | SD | CV % | Min | Median | Max | Geometric Mean |
|---|---|---|---|---|---|---|---|---|
| $AUC_{0-inf}$ (h*ng/mL) | 7 | 499.30 | 372.97 | 74.70 | 177.40 | 345.07 | 1086.15 | 396.03 |
| $AUC_{0-t}$ (h*ng/mL) | 7 | 481.65 | 366.18 | 76.03 | 163.96 | 328.49 | 1050.66 | 377.56 |
| Residual area (%) | 7 | 4.64 | 2.31 | 49.80 | 2.00 | 4.81 | 7.58 | 4.11 |
| $C_{max}$ (ng/mL) | 7 | 28.2 | 19.9 | 70.7 | 9.20 | 20.8 | 58.5 | 22.3 |
| $T_{max}$ (h) | 7 | 6.010 | 3.337 | 55.526 | 3.000 | 5.000 | 12.067 | 5.330 |
| $T_{1/2\ el}$ (h) | 7 | 8.01 | 1.50 | 18.76 | 5.82 | 7.56 | 10.36 | 7.89 |
| $K_{el}$ (/h) | 7 | 0.0892 | 0.0171 | 19.1497 | 0.0669 | 0.0917 | 0.1190 | 0.0878 |
| Cl/F (L/h) | 7 | 166.24 | 99.67 | 59.95 | 49.72 | 156.49 | 304.39 | 136.35 |
| $V_d$/F (L) | 7 | 1976.26 | 1379.82 | 69.82 | 615.01 | 1622.34 | 3783.67 | 1552.78 |

N: number of observations;
SD: Standard deviation;
CV: Coefficient of Variation;
Min: minimum;
Max: Maximum;
'—': not calculated Table 4A below provides a summary of the observed plasma pharmacokinetic parameters for Nalbuphine following administration of Nalbuphine ER tablets (108 mg, Single Dose) in patients from Cohort 3 with mild hepatic impairment.

TABLE 4A

| Parameter (unit) | N | Mean | SD | CV % | Min | Median | Max | Geometric Mean |
|---|---|---|---|---|---|---|---|---|
| $AUC_{0-inf}$ (h*ng/mL) | 6 | 316.16 | 102.07 | 32.28 | 152.93 | 329.23 | 463.12 | 300.09 |
| $AUC_{0-t}$ (h*ng/mL) | 8 | 270.08 | 105.60 | 39.10 | 133.81 | 278.18 | 447.44 | 250.97 |
| Residual area (%) | 6 | 4.12 | 1.70 | 41.27 | 3.14 | 3.53 | 7.56 | 3.91 |
| $C_{max}$ (ng/mL) | 8 | 14.8 | 5.03 | 34.1 | 6.58 | 14.9 | 21.7 | 13.9 |
| $T_{max}$ (h) | 8 | 6.317 | 4.145 | 65.616 | 1.500 | 5.000 | 12.000 | 5.078 |
| $T_{1/2\ el}$ (h) | 6 | 8.54 | 2.37 | 27.74 | 4.95 | 8.80 | 12.05 | 8.25 |
| $K_{el}$ (/h) | 6 | 0.0874 | 0.0286 | 32.7472 | 0.0575 | 0.0788 | 0.1401 | 0.0840 |

TABLE 4A-continued

| Parameter (unit) | N | Mean | SD | CV % | Min | Median | Max | Geometric Mean |
|---|---|---|---|---|---|---|---|---|
| Cl/F (L/h) | 6 | 383.67 | 166.78 | 43.47 | 233.20 | 328.31 | 706.20 | 359.89 |
| $V_d$/F (L) | 6 | 4542.31 | 1758.30 | 38.71 | 2847.30 | 4045.84 | 7369.46 | 4282.18 |

N: number of observations;
SD: Standard deviation;
CV: Coefficient of Variation;
Min: minimum;
Max: Maximum;
'—': not calculated Table 4B below provides a summary of the observed plasma pharmacokinetic parameters for Nalbuphine following administration of Nalbuphine ER tablets (108 mg, Single Dose) in patients from Cohort 3 with moderate hepatic impairment.

TABLE 4B

| Parameter (unit) | N | Mean | SD | CV % | Min | Median | Max | Geometric Mean |
|---|---|---|---|---|---|---|---|---|
| $AUC_{0\text{-}inf}$ (h*ng/mL) | 7 | 1011.19 | 617.95 | 61.11 | 300.27 | 871.79 | 1888.98 | 846.41 |
| $AUC_{0\text{-}t}$ (h*ng/mL) | 7 | 999.43 | 618.03 | 61.84 | 279.97 | 864.71 | 1867.64 | 830.15 |
| Residual area (%) | 7 | 1.90 | 2.22 | 116.93 | 0.37 | 1.13 | 6.76 | 1.23 |
| $C_{max}$ (ng/mL) | 7 | 49.2 | 25.7 | 52.2 | 14.3 | 53.6 | 82.7 | 42.4 |
| $T_{max}$ (h) | 7 | 7.857 | 4.375 | 55.685 | 3.000 | 9.000 | 12.000 | 6.625 |
| $T_{1/2\ el}$ (h) | 7 | 8.35 | 2.25 | 26.90 | 5.92 | 7.81 | 11.63 | 8.10 |
| $K_{el}$ (/h) | 7 | 0.0879 | 0.0216 | 24.6125 | 0.0596 | 0.0888 | 0.1172 | 0.0855 |
| Cl/F (L/h) | 7 | 154.66 | 106.73 | 69.01 | 57.17 | 123.88 | 359.67 | 127.60 |
| $V_d$/F (L) | 7 | 1990.47 | 1901.37 | 95.52 | 678.91 | 1170.14 | 6034.79 | 1491.94 |

N: number of observations;
SD: Standard deviation;
CV: Coefficient of Variation;
Min: minimum;
Max: Maximum;
'—': not calculated Table 5A below provides a summary of the observed plasma pharmacokinetic parameters for Nalbuphine following administration of Nalbuphine ER tablets (162 mg, Single Dose) in patients from Cohort 4 with mild hepatic impairment.

TABLE 5A

| Parameter (unit) | N | Mean | SD | CV % | Min | Median | Max | Geometric Mean |
|---|---|---|---|---|---|---|---|---|
| $AUC_{0\text{-}inf}$ (h*ng/mL) | 6 | 375.54 | 128.29 | 34.16 | 227.15 | 387.28 | 527.65 | 356.12 |
| $AUC_{0\text{-}t}$ (h*ng/mL) | 7 | 375.27 | 118.47 | 31.57 | 220.71 | 434.22 | 501.79 | 357.32 |
| Residual area (%) | 6 | 3.54 | 1.53 | 43.07 | 2.08 | 3.19 | 5.80 | 3.28 |
| $C_{max}$ (ng/mL) | 7 | 19.9 | 6.95 | 34.9 | 10.7 | 22.4 | 28.6 | 18.7 |
| $T_{max}$ (h) | 7 | 9.786 | 7.233 | 73.917 | 3.000 | 7.000 | 24.000 | 7.882 |
| $T_{1/2\ el}$ (h) | 6 | 9.47 | 1.74 | 18.37 | 7.14 | 9.55 | 11.49 | 9.33 |
| $K_{el}$ (/h) | 6 | 0.0754 | 0.0144 | 19.1416 | 0.0603 | 0.0735 | 0.0970 | 0.0743 |
| Cl/F (L/h) | 6 | 481.08 | 177.65 | 36.93 | 307.02 | 427.29 | 713.18 | 454.90 |
| $V_d$/F (L) | 6 | 6320.94 | 1685.58 | 26.67 | 4069.34 | 6519.04 | 8518.44 | 6122.93 |

N: number of observations;
SD: Standard deviation;
CV: Coefficient of Variation;
Min: minimum;
Max: Maximum;
'—': not calculated Table 5B below provides a summary of the observed plasma pharmacokinetic parameters for Nalbuphine following administration of Nalbuphine ER tablets (162 mg, Single Dose) in patients from Cohort 4 with moderate hepatic impairment.

TABLE 5B

| Parameter (unit) | N | Mean | SD | CV % | Min | Median | Max | Geometric Mean |
|---|---|---|---|---|---|---|---|---|
| $AUC_{0-inf}$ (h*ng/mL) | 6 | 1251.90 | 751.89 | 62.46 | 472.00 | 1194.48 | 2689.95 | 1074.11 |
| $AUC_{0-t}$ (h*ng/mL) | 6 | 1233.95 | 784.14 | 63.55 | 443.76 | 1184.33 | 2672.96 | 1050.63 |
| Residual area (%) | 6 | 2.17 | 2.08 | 95.78 | 0.36 | 1.56 | 5.98 | 1.46 |
| $C_{max}$ (ng/mL) | 6 | 65.4 | 36.2 | 55.3 | 28.6 | 67.4 | 127 | 57.2 |
| $T_{max}$ (h) | 6 | 7.167 | 3.125 | 43.607 | 3.000 | 7.000 | 12.000 | 6.556 |
| $T_{1/2\ el}$ (h) | 6 | 8.70 | 2.75 | 31.64 | 5.48 | 8.25 | 13.69 | 8.37 |
| $K_{el}$ (/h) | 6 | 0.0559 | 0.0249 | 28.9590 | 0.0506 | 0.0841 | 0.1266 | 0.0828 |
| Cl/F (L/h) | 6 | 174.89 | 103.09 | 58.95 | 60.22 | 135.63 | 343.22 | 150.82 |
| $V_d$/F (L) | 6 | 2414.87 | 2255.28 | 93.39 | 793.44 | 1486.60 | 6779.04 | 1820.96 |

N: number of observations;
SD: Standard deviation;
CV: Coefficient of Variation;
Min: minimum;
Max: Maximum;
'—': not calculated As shown in FIGS. 5-8 pharmacokinetic parameters showed dose-proportional increases in exposure ($C_{max}$ and AUC) after the initial dose for patients with mild and moderate hepatic impairment. Patients with moderate hepatic impairment exhibit a ~2.5-3-fold higher exposure than patients with mild hepatic impairment. Terminal half-life ($T_{1/2}$) and Time to maximal concentration ($T_{max}$) do not appear to change for patients with mild and moderate hepatic impairment.

Table 6 below provides a summary of the observed plasma pharmacokinetic parameters for Nalbuphine following administration of Nalbuphine ER tablets (162 mg, Single Dose) in healthy control patients from Cohort 5.

TABLE 6

| Parameter (unit) | N | Mean | SD | CV % | Min | Median | Max | Geometric Mean |
|---|---|---|---|---|---|---|---|---|
| $AUC_{0-inf}$ (h*ng/mL) | 7 | 437.81 | 296.71 | 67.77 | 199.63 | 283.33 | 1047.93 | 374.83 |
| $AUC_{0-t}$ (h*ng/mL) | 7 | 417.78 | 293.31 | 70.21 | 181.96 | 272.15 | 1035.04 | 355.42 |
| Residual area (%) | 7 | 5.12 | 34.9 | 68.13 | 1.23 | 3.93 | 11.07 | 4.17 |
| $C_{max}$ (ng/mL) | 7 | 27.0 | 9.24 | 34.2 | 14.9 | 27.0 | 44.1 | 25.7 |
| $T_{max}$ (h) | 7 | 5.567 | 1.904 | 34.206 | 2.983 | 5.000 | 9.000 | 5.298 |
| $T_{1/2\ el}$ (h) | 7 | 9.87 | 2.45 | 24.86 | 6.84 | 10.00 | 14.09 | 9.61 |
| $K_{el}$ (/h) | 7 | 0.0741 | 0.0185 | 24.9677 | 0.0492 | 0.0693 | 0.1014 | 0.0721 |
| Cl/F (L/h) | 7 | 486.82 | 224.27 | 46.07 | 154.59 | 571.78 | 811.50 | 432.20 |
| $V_d$/F (L) | 7 | 6564.55 | 2963.72 | 45.15 | 2486.18 | 5953.82 | 12154.74 | 5990.84 |

N: number of observations;
SD: Standard deviation;
CV: Coefficient of Variation;
Min: minimum;
Max: Maximum;
'—': not calculated The pharmacokinetic parameters in Table 6 was consistent with data obtained in healthy subjects in the cross-study comparison.

Table 7 depicts the results of a cross-study comparison evaluating the plasma PK parameters in patients from Cohorts 1-4 with Child Pugh A, Child Pugh B, or Child Pugh C liver impairment relative to other patients with normal liver function.

TABLE 7

| Dose | 27 mg | | | 54 mg | | 108 mg | | 162 mg | |
|---|---|---|---|---|---|---|---|---|---|
| Hepatic status | Mild | Moderate | Severe | Mild | Moderate | Mild | Moderate | Mild | Moderate |
| AUC | Similar[a] | 3.5X | 8X | 1.5X | 4X | 1.5X | 4X | Similar | 4X |
| $C_{max}$ | Similar | 2.5X | 6X | Similar | 3X | Similar | 4X | Similar | 3X |
| $T_{max}$ | Similar | Similar | Similar | Similar | Similar | Similar | Similar | Similar | Similar |
| $T_{1/2}$ | Similar | Similar | Similar | Similar | Similar | Similar | Similar | Similar | Similar |

[a]Similar refers to the PK being similar to healthy volunteers

As shown in Table 7, for patients with mild hepatic impairment, the effect on exposure (Cmax, or even AUC) is minimal ~1.5 fold across doses as compared to healthy subjects in the cross-study comparison. For subjects with moderate hepatic impairment, the exposure (AUC and Cmax) increase is ~3 to 4-fold across doses as compared to healthy subjects. For subjects with severe hepatic impairment, the exposure (AUC and Cmax) increase is ~6 to 8-fold at 27 mg dose as compared to healthy subjects. After multiple dosing, an accumulation similar to that of healthy subjects (×1.6) is expected based on the data from the cross-study comparison. However, concentrations could be ~4-fold higher than that seen after multiple dosing in healthy.

Significantly, the half-life of nalbuphine was similar across cohorts 1-4, indicating that no higher accumulation of nalbuphine is expected relative to healthy controls. Furthermore, since the half-life of nalbuphine is similar across cohorts 1-4, no changes to the dosing frequency following titration to the effective dose are expected relative to healthy controls.

Since the PK of the drug shows only 1.5 fold increase in AUC with similar Cmax findings in the cross-study comparison, no change in titrating liver impairment Childs Pugh A patients ("mild hepatic impairment") relative to other patients with normal liver function is recommended.

In Child Pugh B ("moderate hepatic impairment") patients, the AUC is 3.5-4 fold higher and the Cmax is anywhere from 2.5 fold higher (at the 27 mg NAL ER dose) to 4-fold higher (at the NAL ER 162 mg dose). When compared to patients with healthy liver function, initial doses will be initiated at lower values and titrate up to a maximal dose that is up to 4-fold lower than in patients with otherwise healthy liver function. Thus the maximal time spent in titration before reaching the upper dose limit of the drug is accomplished in a shorter time period (over approximately 7-10 days) assuming a typical titration rate of spending 3-4 days at a given titration dose prior to dose escalation. Since there is no alteration in half-life of the drug, BID will still be the dosing regimen following titration to the effective dose. Since AEs can be either Cmax related or AUC ("exposure") related there will be titration instructions that are different in Child Pugh B patients ("moderate hepatic impairment").

In Child Pugh C ("severe hepatic impairment") patients, the $C_{max}$ and $AUC_{inf}$ values for subjects with severe hepatic impairment following administration of 27 mg dose (See Table 2C) are ~6 to 8 fold higher than the $C_{max}$ range and $AUC_{inf}$ range observed in healthy volunteers at 162 mg dose. The $T_{max}$ range for the subjects with severe impairment is similar to that observed for other cohorts (between 3 and 9 hours). The $T_{1/2}$ values for the subjects with severe impairment of ~8 hours remains unchanged for these subjects as compared to other cohorts.

EMBODIMENTS

1. A method of treating a nalbuphine-treatable disorder in a hepatically impaired patient, comprising:
   (a) determining the patient's Child-Pugh score;
   (b) administering a daily dose of about 15 mg to about 360 mg of nalbuphine, or a pharmaceutically acceptable salt or ester thereof, to a patient with a Child-Pugh score of A; and
   (c) administering a daily dose of about 4 mg to about 120 mg of nalbuphine, or a pharmaceutically acceptable salt thereof, to a patient with a Child-Pugh score of B or C, wherein the nalbuphine-treatable disorder is selected from the group consisting of chronic cough, pruritus, prurigo nodularis, uremic pruritus, tardive dyskinesia, Huntington's disease, and levodopa-induced dyskinesia (LID).

2. The method of embodiment 1, wherein the patient's Child-Pugh score is A.

3. The method of embodiment 2, wherein the daily administered dose is from about 14 mg to about 324 mg of an Equivalent Amount of Nalbuphine Free Base.

4. The method of embodiment 2, wherein about 14 mg of the Equivalent Amount of Nalbuphine Free Base is administered once a day.

5. The method of embodiment 2, wherein about 14 mg of the Equivalent Amount of Nalbuphine Free Base is administered twice a day.

6. The method of embodiment 2, wherein about 28 mg of the Equivalent Amount of Nalbuphine Free Base is administered once a day.

7. The method of embodiment 2, wherein about 28 mg of the Equivalent Amount of Nalbuphine Free Base is administered twice a day.

8. The method of embodiment 2, wherein about 54 mg of the Equivalent Amount of Nalbuphine Free Base is administered once a day.

9. The method of embodiment 2, wherein about 54 mg of the Equivalent Amount of Nalbuphine Free Base is administered twice a day.

10. The method of embodiment 2, wherein about 81 mg of the Equivalent Amount of Nalbuphine Free Base is administered once a day.

11. The method of embodiment 2, wherein about 81 mg of the Equivalent Amount of Nalbuphine Free Base is administered twice a day.

12. The method of embodiment 2, wherein about 108 mg of the Equivalent Amount of Nalbuphine Free Base is administered once a day.

13. The method of embodiment 2, wherein about 108 mg of the Equivalent Amount of Nalbuphine Free Base is administered twice a day.

14. The method of embodiment 2, wherein about 162 mg of the Equivalent Amount of Nalbuphine Free Base is administered once a day.

15. The method of embodiment 2, wherein about 162 mg of the Equivalent Amount of Nalbuphine Free Base thereof is administered twice a day.

16. The method of embodiment 2, wherein about 324 mg of the Equivalent Amount of Nalbuphine Free Base is administered once a day.

17. The method of embodiment 2, wherein the daily administered dose is from about 15 mg to about 360 mg of the nalbuphine, or a pharmaceutically acceptable salt thereof.

18. The method of embodiment 17, wherein about 15 mg of nalbuphine, or a pharmaceutically acceptable salt or ester thereof, is administered once a day.

19. The method of embodiment 17, wherein about 15 mg of nalbuphine, or a pharmaceutically acceptable salt or ester thereof, is administered twice a day.

20. The method of embodiment 17, wherein about 30 mg of nalbuphine, or a pharmaceutically acceptable salt or ester thereof, is administered once a day.

21. The method of embodiment 17, wherein about 30 mg of nalbuphine, or a pharmaceutically acceptable salt or ester thereof, is administered twice a day.

22. The method of embodiment 17, wherein about 60 mg of nalbuphine, or a pharmaceutically acceptable salt or ester thereof, is administered once a day.

23. The method of embodiment 17, wherein about 60 mg of nalbuphine, or a pharmaceutically acceptable salt or ester thereof, is administered twice a day.

24. The method of embodiment 17, wherein about 90 mg of nalbuphine, or a pharmaceutically acceptable salt or ester thereof, is administered once a day.

25. The method of embodiment 17, wherein about 90 mg of nalbuphine, or a pharmaceutically acceptable salt or ester thereof, is administered twice a day.

26. The method of embodiment 17, wherein about 120 mg of nalbuphine, or a pharmaceutically acceptable salt or ester thereof, is administered once a day.

27. The method of embodiment 17, wherein about 120 mg of nalbuphine, or a pharmaceutically acceptable salt or ester thereof, is administered twice a day.

28. The method of embodiment 17, wherein about 180 mg of nalbuphine, or a pharmaceutically acceptable salt or ester thereof, is administered once a day.

29. The method of embodiment 17, wherein about 180 mg of nalbuphine, or a pharmaceutically acceptable salt or ester thereof, is administered twice a day.

30. The method of embodiment 17, wherein about 360 mg of nalbuphine, or a pharmaceutically acceptable salt or ester thereof, is administered once a day.

31. The method of any one of embodiments 1-30, further comprising titrating the dose for about 7 to 30 days.

32. The method of any one of embodiments 1-30, further comprising titrating the dose for about 7 to 14 days.

33. The method of any one of embodiments 31-32, wherein the titration comprises administration of nalbuphine, or a pharmaceutically acceptable salt thereof, to the following schedule:

| Day | AM dosage (mg) | PM dosage (mg) |
|---|---|---|
| Day 1 | 0 | 30 |
| Day 2 | 0 | 30 |
| Day 3 | 30 | 30 |
| Day 4 | 30 | 30 |
| Day 5 | 30 | 60 |
| Day 6 | 60 | 60 |
| Day 7 | 60 | 60 |
| Day 8 | 60 | 90 |
| Day 9 | 90 | 90 |
| Day 10 | 90 | 90 |
| Day 11 | 90 | 120 |
| Day 12 | 120 | 120 |
| Day 13 | 120 | 120 |
| Day 14 | 120 | 180 |

34. The method of any one of embodiments 31-32, wherein the titration comprises administration of an Equivalent Amount of Nalbuphine Free Base according to the following schedule:

| Day | AM dosage (mg) | PM dosage (mg) |
|---|---|---|
| Day 1 | 0 | 28 |
| Day 2 | 0 | 28 |
| Day 3 | 28 | 28 |
| Day 4 | 28 | 28 |
| Day 5 | 28 | 54 |
| Day 6 | 54 | 54 |
| Day 7 | 54 | 54 |
| Day 8 | 54 | 81 |
| Day 9 | 81 | 81 |
| Day 10 | 81 | 81 |
| Day 11 | 81 | 108 |
| Day 12 | 108 | 108 |
| Day 13 | 108 | 108 |
| Day 14 | 108 | 162. |

35. The method of any one of embodiments 31-32, wherein the titration comprises administration of nalbuphine, or a pharmaceutically acceptable salt thereof, to the following schedule:

| Day | AM dosage (mg) | PM dosage (mg) |
|---|---|---|
| Day 1 | 0 | 30 |
| Day 2 | 0 | 30 |
| Day 3 | 30 | 30 |
| Day 4 | 30 | 30 |
| Day 5 | 30 | 60 |
| Day 6 | 60 | 60 |
| Day 7 | 60 | 60 |
| Day 8 | 60 | 90 |
| Day 9 | 90 | 90 |
| Day 10 | 90 | 90 |
| Day 11 | 90 | 120 |
| Day 12 | 120 | 120 |
| Day 13 | 120 | 120 |
| Day 14 | 120 | 120 |

36. The method of any one of embodiments 31-32, wherein the titration comprises administration of an Equivalent Amount of Nalbuphine Free Base according to the following schedule:

| Day | AM dosage (mg) | PM dosage (mg) |
|---|---|---|
| Day 1 | 0 | 28 |
| Day 2 | 0 | 28 |
| Day 3 | 28 | 28 |
| Day 4 | 28 | 28 |
| Day 5 | 28 | 54 |
| Day 6 | 54 | 54 |
| Day 7 | 54 | 54 |
| Day 8 | 54 | 81 |

-continued

| Day | AM dosage (mg) | PM dosage (mg) |
| --- | --- | --- |
| Day 9 | 81 | 81 |
| Day 10 | 81 | 81 |
| Day 11 | 81 | 108 |
| Day 12 | 108 | 108 |
| Day 13 | 108 | 108 |
| Day 14 | 108 | 108. |

37. The method of any one of embodiments 31-32, wherein the titration comprises administration of nalbuphine, or a pharmaceutically acceptable salt thereof, according to the following schedule:

| Day | AM dosage (mg) | PM dosage (mg) |
| --- | --- | --- |
| Day 1 | 0 | 30 |
| Day 2 | 0 | 30 |
| Day 3 | 30 | 30 |
| Day 4 | 30 | 30 |
| Day 5 | 30 | 60 |
| Day 6 | 60 | 60 |
| Day 7 | 60 | 60 |
| Day 8 | 60 | 60 |
| Day 9 | 60 | 120 |
| Day 10 | 120 | 120 |
| Day 11 | 120 | 120 |
| Day 12 | 120 | 120 |
| Day 13 | 120 | 120 |
| Day 14 | 120 | 120 |
| Day 15 | 120 | 120 |
| Day 16 | 120 | 180 |
| Day 17 | 180 | 180 |

38. The method of any one of embodiments 31-32, wherein the titration comprises administration of an Equivalent Amount of Nalbuphine Free Base according to the following schedule:

| Day | AM dosage (mg) | PM dosage (mg) |
| --- | --- | --- |
| Day 1 | 0 | 28 |
| Day 2 | 0 | 28 |
| Day 3 | 28 | 28 |
| Day 4 | 28 | 28 |
| Day 5 | 28 | 54 |
| Day 6 | 54 | 54 |
| Day 7 | 54 | 54 |
| Day 8 | 54 | 54 |
| Day 9 | 54 | 108 |
| Day 10 | 108 | 108 |
| Day 11 | 108 | 108 |
| Day 12 | 108 | 108 |
| Day 13 | 108 | 108 |
| Day 14 | 108 | 108 |
| Day 15 | 108 | 108 |
| Day 16 | 108 | 162 |
| Day 17 | 162 | 162. |

39. The method of embodiment 1, wherein the patient's Child-Pugh score is B.

40. The method of embodiment 1, wherein the patient's Child-Pugh score is C.

41. The method of any one of embodiments 39-40, wherein the daily administered dose is from about 3 mg to about 108 mg of an Equivalent Amount of Nalbuphine Free Base.

42. The method of any one of embodiments 39-40, wherein about 6 mg of the Equivalent Amount of Nalbuphine Free Base is administered once a day.

43. The method of any one of embodiments 39-40, wherein about 6 mg of the Equivalent Amount of Nalbuphine Free Base is administered twice a day.

44. The method of any one of embodiments 39-40, wherein about 9 mg of the Equivalent Amount of Nalbuphine Free Base is administered once a day.

45. The method of any one of embodiments 39-40, wherein about 9 mg of the Equivalent Amount of Nalbuphine Free Base is administered twice a day.

46. The method of any one of embodiments 39-40, wherein about 14 mg of the Equivalent Amount of Nalbuphine Free Base is administered once a day.

47. The method of any one of embodiments 39-40, wherein about 14 mg of the Equivalent Amount of Nalbuphine Free Base is administered twice a day.

48. The method of any one of embodiments 39-40, wherein about 18 mg of the Equivalent Amount of Nalbuphine Free Base is administered once a day.

49. The method of any one of embodiments 39-40, wherein about 18 mg of the Equivalent Amount of Nalbuphine Free Base is administered twice a day.

50. The method of any one of embodiments 39-40, wherein about 28 mg of the Equivalent Amount of Nalbuphine Free Base is administered once a day.

51. The method of any one of embodiments 39-40, wherein about 28 mg of the Equivalent Amount of Nalbuphine Free Base is administered twice a day.

52. The method of any one of embodiments 39-40, wherein about 36 mg of the Equivalent Amount of Nalbuphine Free Base is administered once a day.

53. The method of any one of embodiments 39-40, wherein about 36 mg of the Equivalent Amount of Nalbuphine Free Base is administered twice a day.

54. The method of any one of embodiments 39-40, wherein about 54 mg of the Equivalent Amount of Nalbuphine Free Base is administered once a day.

55. The method of any one of embodiments 39-40, wherein about 54 mg of the Equivalent Amount of Nalbuphine Free Base is administered twice a day.

56. The method of any one of embodiments 39-40, wherein the daily administered dose is from about 7 mg to about 120 mg of the nalbuphine, or a pharmaceutically acceptable salt thereof.

57. The method of any one of embodiments 39-40, wherein about 7 mg of the Nalbuphine, or a pharmaceutically acceptable salt thereof, is administered once a day.

58. The method of any one of embodiments 39-40, wherein about 7 mg of the Nalbuphine, or a pharmaceutically acceptable salt thereof, is administered twice a day.

59. The method of any one of embodiments 39-40, wherein about 10 mg of the Nalbuphine, or a pharmaceutically acceptable salt thereof, is administered once a day.

60. The method of any one of embodiments 39-40, wherein about 10 mg of the Nalbuphine, or a pharmaceutically acceptable salt thereof, is administered twice a day.

61. The method of any one of embodiments 39-40, wherein about 15 mg of the Nalbuphine, or a pharmaceutically acceptable salt thereof, is administered once a day.

62. The method of any one of embodiments 39-40, wherein about 15 mg of the Nalbuphine, or a pharmaceutically acceptable salt thereof, is administered twice a day.

63. The method of any one of embodiments 39-40, wherein about 20 mg of the Nalbuphine, or a pharmaceutically acceptable salt thereof, is administered once a day.

64. The method of any one of embodiments 39-40, wherein about 20 mg of the Nalbuphine, or a pharmaceutically acceptable salt thereof, is administered twice a day.

65. The method of any one of embodiments 39-40, wherein about 31 mg of the Nalbuphine, or a pharmaceutically acceptable salt thereof, is administered once a day.

66. The method of any one of embodiments 39-40, wherein about 31 mg of the Nalbuphine, or a pharmaceutically acceptable salt thereof, is administered twice a day.

67. The method of any one of embodiments 39-40, wherein about 40 mg of the Nalbuphine, or a pharmaceutically acceptable salt thereof, is administered once a day.

68. The method of any one of embodiments 39-40, wherein about 40 mg of the Nalbuphine, or a pharmaceutically acceptable salt thereof, is administered twice a day.

69. The method of any one of embodiments 39-40, wherein about 60 mg of the Nalbuphine, or a pharmaceutically acceptable salt thereof, is administered once a day.

70. The method of any one of embodiments 39-40, wherein about 60 mg of the Nalbuphine, or a pharmaceutically acceptable salt thereof, is administered twice a day.

71. The method of any one of embodiments 39-70, further comprising titrating the dose for about 7 to 30 days.

72. The method of any one of embodiments 39-70, further comprising titrating the dose for about 7 to 14 days.

73. The method of embodiment 71, wherein the titration comprises administration of Equivalent Amount of Nalbuphine Free Base according to the following schedule:

| Day | AM dosage (mg) | PM dosage (mg) |
| --- | --- | --- |
| Day 1 | 0 | 9-14 |
| Day 2 | 0 | 9-14 |
| Day 3 | 0 | 9-14 |
| Day 4 | 9-14 | 9-14 |
| Day 5 | 9-14 | 9-14 |
| Day 6 | 9-14 | 18-28 |
| Day 7 | 18-28 | 18-28 |
| Day 8 | 18-28 | 18-28 |
| Day 9 | 18-28 | 18-28 |
| Day 10 | 18-28 | 36-54 |
| Day 11 | 54 | 54 |

74. The method of embodiment 71, wherein the titration comprises administration of nalbuphine, or a pharmaceutically acceptable salt thereof, according to the following

| Day | AM dosage (mg) | PM dosage (mg) |
| --- | --- | --- |
| Day 1 | 0 | 10-15 |
| Day 2 | 0 | 10-15 |
| Day 3 | 0 | 10-15 |
| Day 4 | 10-15 | 10-15 |
| Day 5 | 10-15 | 10-15 |
| Day 6 | 10-15 | 20-31 |
| Day 7 | 20-31 | 20-31 |
| Day 8 | 20-31 | 20-31 |
| Day 9 | 20-31 | 20-31 |
| Day 10 | 20-31 | 40-60 |
| Day 11 | 60 | 60 |

75. The method of embodiment 71, wherein the titration comprises administration of Equivalent Amount of Nalbuphine Free Base according to the following schedule:

| Day | AM dosage (mg) | PM dosage (mg) |
| --- | --- | --- |
| Day 1 | 0 | 9 |
| Day 2 | 0 | 9 |
| Day 3 | 0 | 9 |
| Day 4 | 9 | 9 |
| Day 5 | 9 | 9 |
| Day 6 | 9 | 18 |
| Day 7 | 18 | 18 |
| Day 8 | 18 | 18 |
| Day 9 | 18 | 18 |
| Day 10 | 18 | 36 |
| Day 11 | 54 | 54 |

76. The method of embodiment 71, wherein the titration comprises administration of nalbuphine, or a pharmaceutically acceptable salt thereof, according to the following schedule:

| Day | AM dosage (mg) | PM dosage (mg) |
| --- | --- | --- |
| Day 1 | 0 | 10 |
| Day 2 | 0 | 10 |
| Day 3 | 0 | 10 |
| Day 4 | 10 | 10 |
| Day 5 | 10 | 10 |
| Day 6 | 10 | 20 |
| Day 7 | 20 | 20 |
| Day 8 | 20 | 20 |
| Day 9 | 20 | 20 |
| Day 10 | 20 | 40 |
| Day 11 | 60 | 60 |

77. The method of embodiment 71, wherein the titration comprises administration of Equivalent Amount of Nalbuphine Free Base according to the following schedule:

| Day | AM dosage (mg) | PM dosage (mg) |
| --- | --- | --- |
| Day 1 | 0 | 14 |
| Day 2 | 0 | 14 |
| Day 3 | 0 | 14 |
| Day 4 | 14 | 14 |
| Day 5 | 14 | 14 |
| Day 6 | 14 | 28 |
| Day 7 | 28 | 28 |
| Day 8 | 28 | 28 |
| Day 9 | 28 | 28 |
| Day 10 | 28 | 54 |
| Day 11 | 54 | 54 |

78. The method of embodiment 71, wherein the titration comprises administration of nalbuphine, or a pharmaceutically acceptable salt thereof, according to the following schedule:

| Day | AM dosage (mg) | PM dosage (mg) |
| --- | --- | --- |
| Day 1 | 0 | 15 |
| Day 2 | 0 | 15 |
| Day 3 | 0 | 15 |
| Day 4 | 15 | 15 |
| Day 5 | 15 | 15 |
| Day 6 | 15 | 31 |
| Day 7 | 31 | 31 |
| Day 8 | 31 | 31 |
| Day 9 | 31 | 31 |
| Day 10 | 31 | 60 |
| Day 11 | 60 | 60 |

79. The method of embodiment 71, wherein the titration comprises administration of Equivalent Amount of Nalbuphine Free Base according to the following schedule:

| Day | AM dosage (mg) | PM dosage (mg) |
| --- | --- | --- |
| Day 1 | 0 | 9-14 |
| Day 2 | 9-14 | 9-14 |
| Day 3 | 9-14 | 9-14 |
| Day 4 | 9-14 | 18-28 |
| Day 5 | 18-28 | 18-28 |
| Day 6 | 18-28 | 18-28 |
| Day 7 | 18-28 | 36-54 |
| Day 8 | 54 | 54 |

80. The method of embodiment 71, wherein the titration comprises administration of nalbuphine, or a pharmaceutically acceptable salt thereof, according to the following schedule:

| Day | AM dosage (mg) | PM dosage (mg) |
| --- | --- | --- |
| Day 1 | 0 | 10-15 |
| Day 2 | 10-15 | 10-15 |
| Day 3 | 10-15 | 10-15 |
| Day 4 | 10-15 | 20-31 |
| Day 5 | 20-31 | 20-31 |
| Day 6 | 20-31 | 20-31 |
| Day 7 | 20-31 | 40-60 |
| Day 8 | 60 | 60 |

81. The method of embodiment 71, wherein the titration comprises administration of Equivalent Amount of Nalbuphine Free Base according to the following schedule:

| Day | AM dosage (mg) | PM dosage (mg) |
| --- | --- | --- |
| Day 1 | 0 | 9 |
| Day 2 | 9 | 9 |
| Day 3 | 9 | 9 |
| Day 4 | 9 | 18 |
| Day 5 | 18 | 18 |
| Day 6 | 18 | 18 |
| Day 7 | 18 | 36 |
| Day 8 | 54 | 54 |

82. The method of embodiment 71, wherein the titration comprises administration of nalbuphine, or a pharmaceutically acceptable salt thereof, according to the following schedule:

| Day | AM dosage (mg) | PM dosage (mg) |
| --- | --- | --- |
| Day 1 | 0 | 10 |
| Day 2 | 10 | 10 |
| Day 3 | 10 | 10 |
| Day 4 | 10 | 20 |
| Day 5 | 20 | 20 |
| Day 6 | 20 | 20 |
| Day 7 | 20 | 40 |
| Day 8 | 60 | 60 |

83. The method of embodiment 71, wherein the titration comprises administration of Equivalent Amount of Nalbuphine Free Base according to the following schedule:

| Day | AM dosage (mg) | PM dosage (mg) |
| --- | --- | --- |
| Day 1 | 0 | 14 |
| Day 2 | 14 | 14 |
| Day 3 | 14 | 14 |
| Day 4 | 14 | 28 |
| Day 5 | 28 | 28 |
| Day 6 | 28 | 28 |
| Day 7 | 28 | 54 |
| Day 8 | 54 | 54 |

84. The method of embodiment 71, wherein the titration comprises administration of nalbuphine, or a pharmaceutically acceptable salt thereof, according to the following schedule:

| Day | AM dosage (mg) | PM dosage (mg) |
| --- | --- | --- |
| Day 1 | 0 | 15 |
| Day 2 | 15 | 15 |
| Day 3 | 15 | 15 |
| Day 4 | 15 | 31 |
| Day 5 | 31 | 31 |
| Day 6 | 31 | 31 |
| Day 7 | 31 | 60 |
| Day 8 | 60 | 60 |

85. The method of any one of the preceding embodiments, wherein the nalbuphine is administered to treat pruritus associated with liver disease.

86. The method of any one of the preceding embodiments, wherein the nalbuphine is administered to treat prurigo nodularis.

87. The method of any one of the preceding embodiments, wherein the nalbuphine is administered to treat uremic pruritus.

88. The method of any one of the preceding embodiments, wherein the nalbuphine is administered to treat idiopathic pulmonary fibrosis (IPF) cough, breathlessness or dyspnea.

89. A method of treating pruritus in hepatically impaired patients comprising:
   (a) determining the patient's Child-Pugh score;
   (b) administering a daily dose of about 15 mg to about 360 mg of nalbuphine, or a pharmaceutically acceptable salt thereof to a patient with a Child-Pugh score of A 90. A method of treating pruritus in hepatically impaired patients comprising:
   (a) determining the patient's Child-Pugh score;
   (b) administering a daily dose of about 4 mg to about 120 mg of nalbuphine, or a pharmaceutically acceptable salt thereof to a patient with a Child-Pugh score of B or C.

91. A method of safely administering nalbuphine, or a pharmaceutically acceptable salt there, in a hepatically impaired patient comprising:
   (a) determining the patient's Child-Pugh score;
   (b) administering a daily dose of about 15 mg to about 360 mg of nalbuphine, or a pharmaceutically acceptable salt thereof to a patient with a Child-Pugh score of A; and
   (c) administering a daily dose of about 4 mg to about 120 mg of nalbuphine, or a pharmaceutically acceptable salt thereof to a patient with a Child-Pugh score of B or C.

92. A method of treating pruritus or idiopathic pulmonary fibrosis (IPF) cough, breathlessness or dyspnea in hepatically impaired patients comprising:
   (a) determining the patient's Child-Pugh score;
   (b) administering a daily dose of about 15 mg to about 360 mg of nalbuphine, or a pharmaceutically acceptable salt thereof to a patient with a Child-Pugh score of A; and (c) administering a daily dose of about 4 mg to about 120 mg of nalbuphine, or a pharmaceutically acceptable salt thereof to a patient with a Child-Pugh score of B or C;

93. A method of treating a nalbuphine-treatable disorder in a hepatically impaired patient, comprising:
(a) determining the patient's Child-Pugh score;
(b) administering a daily dose of about 15 mg to about 360 mg of nalbuphine, or a pharmaceutically acceptable salt or ester thereof, to a patient with a Child-Pugh score of A;
(c) administering a daily dose of about 4 mg to about 120 mg of nalbuphine, or a pharmaceutically acceptable salt thereof to a patient with a Child-Pugh score of B; and
(d) administering a daily dose of about 2 mg to about 45 mg of nalbuphine, or a pharmaceutically acceptable salt thereof to a patient with a Child-Pugh score of C;

94. A method of treating pruritus in hepatically impaired patients comprising:
(a) determining the patient's Child-Pugh score;
(b) administering a daily dose of about 4 mg to about 120 mg of nalbuphine, or a pharmaceutically acceptable salt thereof to a patient with a Child-Pugh score of B; and
(d) administering a daily dose of about 2 mg to about 45 mg of nalbuphine, or a pharmaceutically acceptable salt thereof to a patient with a Child-Pugh score of C.

95. A method of safely administering nalbuphine, or a pharmaceutically acceptable salt thereof, in a hepatically impaired patient comprising:
(a) determining the patient's Child-Pugh score;
(b) administering a daily dose of about 15 mg to about 360 mg of nalbuphine, or a pharmaceutically acceptable salt thereof to a patient with a Child-Pugh score of A;
(c) administering a daily dose of about 4 mg to about 120 mg of nalbuphine, or a pharmaceutically acceptable salt thereof to a patient with a Child-Pugh score of B; and
(d) administering a daily dose of about 2 mg to about 45 mg of nalbuphine, or a pharmaceutically acceptable salt thereof to a patient with a Child-Pugh score of C.

96. method of treating pruritus or idiopathic pulmonary fibrosis (IPF) cough, breathlessness or dyspnea in hepatically impaired patients comprising:
(a) determining the patient's Child-Pugh score;
(b) administering a daily dose of about 15 mg to about 360 mg of nalbuphine, or a pharmaceutically acceptable salt thereof to a patient with a Child-Pugh score of A;
(c) administering a daily dose of about 4 mg to about 120 mg of nalbuphine, or a pharmaceutically acceptable salt thereof to a patient with a Child-Pugh score of B; and
(d) administering a daily dose of about 2 mg to about 45 mg of nalbuphine, or a pharmaceutically acceptable salt thereof to a patient with a Child-Pugh score of C.

97. The method of embodiment 94, wherein from about 18 mg to about 27 mg of the Equivalent Amount of Nalbuphine Free Base is administered once a day.

What is claimed is:

1. A method of treating idiopathic pulmonary fibrosis (IPF) cough in a hepatically impaired patient, comprising:
(a) determining whether a patient is hepatically impaired; and
(b) orally administering a daily dose of about 9 mg to about 54 mg of an Equivalent Amount of Nalbuphine Free Base to a patient with severe hepatic impairment.

2. The method of claim 1, wherein the patient's hepatic impairment is determined using the patient's Child-Pugh score.

3. The method of claim 1, wherein the administration provides in the patient a mean $AUC_{tau}$ from about 40 ng·hr/mL to about 200 ng·hr/mL.

4. The method of claim 1, wherein the administration provides in the patient a mean $C_{max}$ of from about 5 ng/ml to about 85 ng/mL.

5. The method of claim 1, wherein the daily administered dose is from about 9 mg to about 41 mg of an Equivalent Amount of Nalbuphine Free Base.

6. The method of claim 1, wherein the daily administered dose is from about 9 mg to about 14 mg of an Equivalent Amount of Nalbuphine Free Base.

7. The method of claim 1, wherein the daily administered dose is from about 18 mg to about 27 mg of an Equivalent Amount of Nalbuphine Free Base.

8. The method of claim 1, wherein about 27 mg of an Equivalent Amount of Nalbuphine Free Base is administered once a day.

9. The method of claim 1, wherein the nalbuphine is administered to the patient twice daily.

10. The method of claim 1, wherein the nalbuphine is administered to the patient once daily.

11. The method of claim 1, further comprising titrating the dose for about 7 to 14 days.

12. A method of treating idiopathic pulmonary fibrosis (IPF) cough in a hepatically impaired patient, comprising:
(a) determining whether a patient is hepatically impaired; and
(b) orally administering a daily dose of about 27 mg to about 108 mg of an Equivalent Amount of Nalbuphine Free Base to a patient with moderate hepatic impairment.

13. The method of claim 12, wherein the patient's hepatic impairment is determined using the patient's Child-Pugh score.

14. The method of claim 12, wherein the administration provides in the patient a mean $AUC_{tau}$ from about 40 ng·hr/mL to about 200 ng·hr/mL.

15. The method of claim 12, wherein the administration provides in the patient a mean $C_{max}$ of from about 5 ng/ml to about 85 ng/ml.

16. The method of claim 12, wherein the daily administered dose is about 27 mg of an Equivalent Amount of Nalbuphine Free Base.

17. The method of claim 12, wherein the daily administered dose is about 54 mg of an Equivalent Amount of Nalbuphine Free Base.

18. The method of claim 12, wherein the daily administered dose is about 108 mg of an Equivalent Amount of Nalbuphine Free Base.

19. The method of claim 12, wherein the nalbuphine is administered to the patient twice daily.

20. The method of claim 12, wherein the nalbuphine is administered to the patient once daily.

21. The method of claim 12, further comprising titrating the dose for about 7 to 14 days.

22. A method of treating idiopathic pulmonary fibrosis (IPF) cough in a hepatically impaired patient, comprising:
(a) determining whether a patient is hepatically impaired; and
(b) orally administering a daily dose of about 27 mg to about 324 mg of an Equivalent Amount of Nalbuphine Free Base to a patient with mild hepatic impairment.

23. The method of claim 22, wherein the patient's hepatic impairment is determined using the patient's Child-Pugh score.

24. The method of claim 22, wherein the administration provides in the patient a mean $AUC_{tau}$ from about 40 ng·hr/mL to about 200 ng·hr/mL.

25. The method of claim 22, wherein the administration provides in the patient a mean $C_{max}$ of from about 5 ng/mL to about 85 ng/mL.

26. The method of claim 22, wherein the daily administered dose is about 108 mg of an Equivalent Amount of Nalbuphine Free Base.

27. The method of claim 22, wherein the daily administered dose is about 324 mg of an Equivalent Amount of Nalbuphine Free Base.

28. The method of claim 22, wherein the nalbuphine is administered to the patient twice daily.

29. The method of claim 22, wherein the nalbuphine is administered to the patient once daily.

30. The method of claim 22, further comprising titrating the dose for about 7 to 14 days.

* * * * *